(12) United States Patent
Crafton et al.

(10) Patent No.: US 7,141,388 B2
(45) Date of Patent: Nov. 28, 2006

(54) NUCLEOTIDE SEQUENCES FOR TRANSCRIPTIONAL REGULATION IN CORYNEBACTERIUM GLUTAMICUM

(75) Inventors: Corey M. Crafton, Decatur, IL (US); P. John Rayapati, Monticello, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 343 days.

(21) Appl. No.: 09/987,763

(22) Filed: Nov. 15, 2001

(65) Prior Publication Data

US 2003/0017553 A1 Jan. 23, 2003

Related U.S. Application Data

(60) Provisional application No. 60/248,219, filed on Nov. 15, 2000.

(51) Int. Cl.
C12P 21/06 (2006.01)
C12N 15/00 (2006.01)
C12N 1/20 (2006.01)
C12N 15/74 (2006.01)
C07H 21/04 (2006.01)

(52) U.S. Cl. ............... 435/69.1; 435/320.1; 435/252.3; 435/252.32; 435/471; 536/23.1; 536/23.2

(58) Field of Classification Search ............... 435/69.1, 435/320.1, 252.3; 536/23.1, 23.2
See application file for complete search history.

(56) References Cited

U.S. PATENT DOCUMENTS

| 5,693,781 | A | 12/1997 | Zupancic et al. | ........... 536/24.1 |
| 5,700,661 | A | 12/1997 | Katsumata et al. | ......... 435/69.1 |
| 5,726,299 | A | 3/1998 | Zupancic et al. | ........... 536/24.1 |
| 5,965,391 | A | 10/1999 | Reinscheid et al. | ......... 435/69.1 |

FOREIGN PATENT DOCUMENTS

| EP | 1 108 790 A2 | 6/2001 |
| WO | WO 88/09819 | 12/1988 |
| WO | WO 96/15246 | 5/1996 |
| WO | WO 01/00844 A2 | 1/2001 |

OTHER PUBLICATIONS

Ngo, in The Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Vyostskaia et al. Acc. No.:AC000132, 1997.*
International Search Report, Sep. 16, 2002 for the corresponding international application PCT/US01/43096.
Vašicová et al., "Integrative and autonomously replicating vectors for analysis of promoters in *Corynebacterium glutamicum*", *Biol. Tech.*, 12:743-746, Chapman & Hall, Ltd. (1998).

Amann, E. et al., "Tightly regulated *tac* promoter vectors useful for the expression of unfused and fused proteins in *Escherichia coli*," *Gene* 69:301-315, Elsevier Science Publishers B.V. (1988).
Archer, J.A.C. and Sinskey, A.J., "The DNA sequence and minimal replicon of the *Corynebacterium glutamicum* plasmid pSR1: evidence of a common ancestry with plasmids from *C. diphtheriae*," *J. Gen. Microbiol.* 139:1753-1759, Society for General Microbiology (1993).
Ben-Samoun, K. et al., "Positively regulated expression of the *Escherichia coli araBAD* promoter in *Corynebacterium glutamicum*," *FEMS Microbiol. Lett.* 174:125-130, Elsevier Science B.V. on behalf of the Federation of European Microbiological Societies (May 1999).
Brosius, J. et al., "Spacing of the -10 and -35 Regions in the *tac* Promoter. Effect on its *in vivo* activity," *J. Biol. Chem.* 260:3539-3541, The American Society of Biological Chemists, Inc. (1985).
Cremer, J. et al., "Regulation of Enzymes of Lysine Biosynthesis in *Corynebacterium glutamicum*," *J. Gen. Microbiol.* 134:3221-3229, Society for General Microbiology (1988).
Jobling, M.G. et al., "Construction of vectors with the p15a replicon, kanamycin resistance, inducible *lacZa* and pUC18 or pUC19 multiple cloning sites," *Nucl. Acids Res.* 18:5315-5316, IRL Press (1990).
Keilhauer, C. et al., "Isoleucine Synthesis in *Corynebacterium glutamicum*: Molecular Analysis of the *ilvB-ilvN-ilvC* Operon," *J. Bacteriol.* 175:5595-5603, American Society for Microbiology (1993).

(Continued)

Primary Examiner—Sumesh Kaushal
(74) Attorney, Agent, or Firm—Buchanan Ingersoll & Rooney PC; Craig G. Cochenour; Duane A. Stewart, III

(57) ABSTRACT

The invention relates to isolated polynucleotides from *Corynebacterium glutamicum* which are useful in the regulation of gene expression. In particular, the invention relates to isolated polynucleotides comprising *C.glutamicum* promoters which may be used to regulate, i.e., either increase or decrease, gene expression. In certain embodiments, isolated promoter sequences of the present invention regulate gene expression through the use of exogenous or endogenous induction. The invention further provides recombinant vectors and recombinant cells comprising isolated polynucleotides of the present invention, preferably in operable association with heterologous genes. Also provided are methods of regulating bacterial gene expression comprising growth of a recombinant cell of the present invention. In particular, the present invention provides methods to regulate genes involved in amino acid production comprising growth of a recombinant cell of the present invention. In certain embodiments, the present invention provides methods of regulating gene expression in bacteria, particularly *Corynebacterium* species, especially of the genus *Corynebacterium*, comprising fermentation growth of a recombinant cell of the present invention, where metabolite concentrations, temperature, or oxygen levels are manipulated to regulate gene expression.

30 Claims, No Drawings

OTHER PUBLICATIONS

Lonsdale, D.M. et al., "pFC1 to pFC7: A Novel Family of Combinatorial Cloning Vectors," *Plant Molec. Biol. Rep. 13*:343-345, International Society for Molecular Plant Biology (1995).

Möckel, B. et al., "Functional and Structural Analyses of Threonine Dehydratase from *Corynebacterium glutamicum*," *J. Bacteriol. 174*:8065-8072, American Society for Microbiology (1992).

Morinaga, Y. et al., "Expression of *Escherichia coli* promoters in *Brevibacterium lactofermentum* using the shuttle vector pEB003," *J. Biotechnol. 5*:305-312, Elsevier Science B.V. (1987).

Oguiza, J.A. et al., "A Gene Encoding Arginyl-tRNA Synthetase Is Located in the Upstream Region of the *lysA* Gene in *Brevibacterium lactofermentum*: Regulation of *argS-lysA* Cluster Expression by Arginine," *J. Bacteriol. 175*:7356-7362, American Society for Microbiology (1993).

Pátek, M. et al., "Leucine Synthesis in *Corynebacterium glutamicum*: Enzyme Activities, Structure of *leuA*, and Effect of *leuA* Inactivation on Lysine Synthesis," *Appl. Environ. Microbiol. 60*:133-140, American Society for Microbiology (1994).

Pátek, M. et al., "Promoters from *Corynebacterium glutamicum*: cloning, molecular analysis and search for a consensus motif," *Microbiol. 142*:1297-1309, Society for General Microbiology (1996).

Reinscheid, D.J. et al., "Cloning, sequence analysis, expression and inactivation of the *Corynebacterium glutamicum pta-ack* operon encoding phosphotransacetylase and acetate kinase," Microbiol. 145:503-513, Society for General Microbiology (Feb. 1999).

Rossi, J.J. et al., "Biological expression of an *Escherichia coli* consensus sequence promoter and some mutant derivatives," *Proc. Natl. Acad. Sci. USA 80*:3203-3207, The National Academy of Sciences (1983).

Sahm, H. et al., "Construction of L-Lysine, L-Threonine-, or L-Isoleucine- Overproducing Strains of *Corynebacterium glutamicum*," *Annals New York Acad. Sci. 782*:25-39, The New York Academy of Sciences (1996).

Vašicová, P. et al., "Analysis of the *Corynebacterium glutamicum dapA* Promoter," *J. Bacteriol. 181*:6188-6191, American Society for Microbiology (Oct. 1999).

Wendisch, V.F. et al., "Regulation of acetate metabolism in *Corynebacterium glutamicum*: transcriptional control of the isocitrate lyase and malate synthase genes," *Arch. Microbiol. 168*:262-269, Springer-Verlag (1997).

\* cited by examiner

NUCLEOTIDE SEQUENCES FOR TRANSCRIPTIONAL REGULATION IN CORYNEBACTERIUM GLUTAMICUM

CROSS REFERENCE TO RELATED APPLICATIONS

This application claims priority to U.S. Provisional Application 60/248,219, filed Nov. 15, 2000, which is incorporated herein by reference in its entirety.

STATEMENT REGARDING FEDERALLY-SPONSORED RESEARCH AND DEVELOPMENT

Not applicable.

BACKGROUND OF THE INVENTION

1. Field of the Invention

The invention relates to the areas of microbial genetics and recombinant DNA technology. The invention provides DNA sequences, vectors, microorganisms, and methods useful for inducing and regulating the expression of genes, including those that are involved in amino acid biosynthesis, in bacterial cells.

2. Background Art

Coryneform bacteria are Gram-positive bacteria frequently used for industrial-scale production of amino acids, purines, and proteins. Although coryneform bacteria, particular *Corynebacterium* species, have been widely used for industrial purposes for many years, the techniques of molecular biology have only recently been employed to augment the usefulness of these organisms in the production of amino acids and other products.

One way to improve the productivity of a microbial strain is to increase the expression of genes that control the production of a metabolite. Increasing expression of a gene can increase the activity of an enzyme that is encoded by that gene. Increasing enzyme activity can increase the rate of synthesis of the metabolic products made by the pathway to which that enzyme belongs. In some instances, increasing the rate of production of a metabolite can unbalance other cellular processes and inhibit growth of a microbial culture. The modified culture will make more product per cell, but will not be able to generate enough cells per volume to show an improvement over the parent strain in a fermentor.

Transcription is the process by which an RNA molecule is synthesized from a DNA template and occurs by the interaction of a multisubunit enzyme complex, known as RNA polymerase, with a DNA molecule. The RNA that is synthesized by this process ultimately directs the production of protein products within the cell. In general, the rate at which RNA is synthesized from DNA, i. e., the transcription rate, directly influences the level of synthesis of the corresponding protein product.

Promoters are DNA sequence elements that regulate the rate at which genes are transcribed. Promoters can influence transcription in a variety of ways. For example, some promoters direct the transcription of their associated genes at a constant rate regardless of the internal external cellular conditions. Such promoters are known as constitutive promoters. In many cases, however, a promoter will direct transcription of its associated gene only under very specific cellular conditions. For example, promoters that turn off gene expression during the growth phase of a microbial culture, but turn on gene expression after optimal growth has been achieved can be used to regulate genes that control production of a metabolite. The new strain will have the same growth pattern as the parent but produce more product per cell. This kind of modification can also improve titer (g product/liter) and yield (g product/g glucose). Nucleotide sequences have been identified that can be used to increase or decrease gene expression in *Corynebacterium* species. These regulatable promoters can increase or decrease the rate at which a gene is transcribed depending on the internal and/or the external cellular conditions. Frequently, the presence of a factor, known as an inducer, can stimulate the rate of transcription from a promoter. Inducers can interact directly with molecules that, themselves, physically interact with the promoter or with DNA sequences in the vicinity of the promoter. Alternatively, the action of an inducer in stimulating transcription from a promoter may be indirect. Whereas inducers function to amplify the level of transcription from a promoter, there is a class of factors, known as suppressors, that reduce or inhibit transcription from a promoter. Like inducers, suppressors can exert their effects either directly or indirectly.

Besides regulation through inducers and suppressors, certain promoters are regulated by temperature. For instance, the level of transcription from a promoter may be increased when cells harboring that promoter are grown at a temperature that is greater than the optimum or normal growth temperature for that cell type. Similarly, there are promoters that will enhance gene expression in cells grown at temperatures below the normal growth temperature.

Promoters are found naturally in wild-type cells where they regulate the expression of specific genes. Promoters, however, are also useful as tools of molecular biology in that they can be isolated from their normal cellular contexts and engineered to regulate the expression of virtually any gene.

The use of regulatory sequences from *Escherichia coli* to control the expression of reporter genes in *Corynebacterium* have been documented. The lacI$^q$ repressor and the tac promoter/reporter genes from *E. coli* were on plasmids that replicate in *Corynebacterium*. See, e.g., Morinaga, Y. et al., *J. Biotechnol.* 5:305–312 (1987). In addition, Ben-Samoun et al., *FEMS Microbiology Letters* 174:125 (1999), which is incorporated herein by reference in its entirety, disclose the use of the *E. coli* araBAD promoter and the araC activator on a plasmid which replicates in *Corynebacterium glutamicum* cells to stimulate the expression of the GFPuv reporter gene only when L-arabinose is present in the growth medium. The authors acknowledge, however, that the level of expression from the araBAD promoter in *C. glutamicum* is 6.5 fold lower than that which was observed in *E. coli*, the native species for the promoter.

U.S. Pat. Nos. 5,693,781 and 5,762,299, each of which are incorporated herein by reference in their entireties, disclose the isolation of promoter sequences from the coryneform bacteria, *Brevibacterium flavum*. Sequences described in these patents were isolated on the basis of their ability to direct expression of a reporter gene in *B. flavum* at a level that was greater than the expression level observed in *B. flavum* with the synthetic tac promoter. Also disclosed in U.S. Pat. Nos. 5,693,781 and 5,762,299, each of which are incorporated herein by reference in their entireties, are *B. flavum* promoters capable of expressing a reporter gene in *B. flavum* cells when grown in medium containing: (a) ethanol but not glucose, and vice versa; (b) glucose but not fructose; and (c) glucose but not casein hydrolysates/yeast extract/ glucose, and vice versa. The novel promoter sequences disclosed in the present application are different from those described in U.S. Pat. Nos. 5,693,781 and 5,762,299.

A limited number of *C. glutamicum* promoters have been described to date. For example, the *C. glutamicum* aceA promoter is disclosed in Wendisch et al., *Arch Microbiol.* 168:262 (1997) and in U.S. Pat. No. 5,700,661 (where it is termed the isocitrate lyase promoter), each of which are incorporated herein by reference in their entireties. In both of these references, the aceA promoter was linked to a reporter gene in transformed *C. glutamicum* cells, and produced an extracellular protein, not a product of metabolic engineering. Expression of the reporter gene was found to be greater in *C. glutamicum* transformants that were grown in the presence of acetate than it was for transformants grown in the presence of glucose (Wendisch et al., *Arch Microbiol.* 168:262 (1997)) or sucrose (U.S. Pat. No. 5,700,661).

Similarly, the aceB promoter from *C. glutamicum* is disclosed in Wendisch et al., *Arch Microbiol.* 168:262 (1997) and in U.S. Pat. No. 5,965,391, which is incorporated herein by reference in its entirety. Both of these references describe transcriptional fusions consisting of the aceB promoter region linked to a reporter gene in *C. glutamicum* transformed cells. Expression of the reporter gene was found to be greater in *C. glutamicum* transformants grown in acetate-containing medium than it was for transformants grown in glucose-containing medium (Wendisch et al., *Arch Microbiol.* 168:262 (1997)) or other carbon sources (U.S. Pat. No. 5,965,391).

Reinscheid et al., *Microbiology* 145:503 (1999), which is incorporated herein by reference in its entirey, discloses a transcriptional fusion between the *C. glutamicum* pta-ack promoter and a reporter gene (chloramphenicol acetyltransferase). *C. glutamicum* cells harboring the transcriptional fusion demonstrated enhanced reporter gene expression when grown in acetate-containing medium as compared to transformed cells that were grown in glucose-containing medium.

In Pátek et al., *Microbiology* 142:1297 (1996), which is incorporated herein by reference in its entirety, several DNA sequences from *C. glutamicum*, identified on the basis of their ability to promote the expression of a chloramphenicol resistance reporter gene in *C. glutamicum* cells, are disclosed and compared to one another in an attempt to define a consensus sequence for *C. glutamicum* promoters.

There is clearly a need for a broader assortment of well-defined *Corynebacterium* species promoters than has been heretofore described. Such promoters would be useful in the constitutive and/or regulated expression of genes in coryneform cells. For example, a collection of *C. glutamicum* promoters, regulated by inexpensive carbon sources, would facilitate the industrial-scale production of amino acids and purines in *C. glutamicum* cells by enhancing the expression of genes that encode components of the biosynthetic pathways for the desired amino acids or purines. Likewise, a versatile array of coryneform promoters would be useful for the industrial scale production of heterologous polypeptides in *C. glutamicum* cells by stimulating the enhanced expression of genes encoding such heterologous polypeptides.

BRIEF SUMMARY OF THE INVENTION

The present invention relates to isolated polynucleotides that function as transcriptional regulators, in particular, promoters, in *Corynebacterium* species host cells, preferably *Corynebacterium glutamicum, Brevibacterium flavum*, or *Brevibacterium lactofermentum* host cells, even more preferably *C. glutamicum*. host cells. These promoters are useful for regulating and enhancing the production of a variety of products in such host cells. Examples of products, the production of which may be enhanced in *Corynebacterium* species host cells as a result of the present invention, are amino acids, such as lysine; purine nucleotides, such as inosinic acid; and heterologous polypeptides. Since *Corynebacterium* species are especially useful for the industrial-scale production of amino acids, purines, and polypeptides, use of the promoters of the present invention may greatly improve the yields of these products from *Corynebacterium* species host cells.

In one embodiment of the present invention, an isolated polynucleotide is provided, comprising a first nucleic acid, the sequence of which is selected from the group consisting of SEQ ID NO:4 through 22.

Further embodiments of the invention include and isolated polynucleotide comprising a first nucleic acid, the sequence of which is at least 90% identical, and more preferably at least 91%, 92%, 93%, 94%, 95%, 96%, 97%, 98% or 99% identical, to a sequence selected from the group consisting of SEQ ID NOs: 4 through 22.

Additional embodiments of the invention include an isolated polynucleotide comprising a first nucleic acid, the sequence of which comprises about 6 contiguous nucleotides, preferably about 10 contiguous nucleotides, even more preferably about 12, 15, 20, 30, 40, 50, 100, 150, 200, or 500 contiguous nucleotides, of a sequence selected from the group consisting of SEQ ID NOs: 4 through 22, wherein the first nucleic acid is capable of regulating transcription of a second nucleic acid, preferably as part of a promoter.

In one aspect of this embodiment, the promoter comprises any one or more of the following genetic elements: a minus 10 ("−10") sequence; a minus 35 ("−35") sequence; a transcription initiation site; an enhancer region; and an operator region. Preferably the genetic elements are specific for *Corynebacterium* species, more preferably are specific for *Corynebacterium glutamicum, Brevibacterium flavum*, and *Brevibacterium lactofermentum*, and even more preferably are specific for *Corynebacterium glutamicum*.

Additional embodiments of the invention include an isolated polynucleotide comprising a first nucleic acid at least 10 nucleotides in length, preferably at least 12, 15, 30, 50 or 150 nucleotides in length, which hybridizes under stringent conditions to a reference nucleic acid, or the complement thereof wherein the sequence of said reference nucleic acid is selected from the group consisting of SEQ ID NOs: 4 through 22. The meaning of the phrase "stringent conditions" as used herein is described infra.

In further embodiments of the present invention, an isolated polynucleotide is provided, comprising a first nucleic acid as described above; and a second nucleic acid. According to this embodiment, the first nucleic acid comprises a transcriptional regulatory region, preferably, a promoter.

In one aspect of this embodiment, said second nucleic acid encodes one or more polypeptides. Preferably, the physical location of the first nucleic acid relative to the second nucleic acid is such that, under the appropriate conditions, the first nucleic acid regulates transcription of the second nucleic acid, thereby facilitating production of the polypeptide.

In another aspect of this embodiment, the second nucleic acid encodes one or more components of a purine biosynthesis pathway. One example of a purine biosynthesis pathway included in this aspect of the invention is the enzymatic pathway that results in the synthesis of inosinic acid.

In another aspect of this embodiment, the second nucleic acid encodes one or more heterologous polypeptides. The heterologous polypeptide may be one that is from a *Corynebacterium* species or one that is from a non-*Corynebacterium* species.

In one particularly preferred aspect of this embodiment, an isolated polynucleotide is provided, comprising a first nucleic acid as described above; and a second nucleic acid, which encodes a component of an amino acid biosynthesis pathway. Examples of amino acid biosynthesis pathways included in this aspect of the invention are the enzymatic pathways that result in the synthesis of L-glycine, L-alanine, L-leucine, L-methionine, L-phenylalanine, L-tryptophan, L-lysine, L-glutamine, L-glutamic acid, L-serine, L-proline, L-valine, L-isoleucine, L-cysteine, L-tyrosine, L-histidine, L-arginine, L-asparagine, L-aspartic acid, and L-threonine.

In a preferred aspect of this embodiment, the second nucleic acid encodes one of the following components of the L-lysine biosynthesis pathway: aspartokinase, aspartate beta-semialdehyde dehydrogenase, diaminopimelate dehydrogenase, diaminopimelate decarboxylase, dihydrodipicolinate synthetase, dihydrodipicolinate reductase, or pyruvate carboxylate.

Another embodiment of the invention provides an isolated polynucleotide comprising a first nucleic acid, the sequence of which is at least 90%, 91%, 92%, 93%, 94%, 95%, 96%, 97%, 98%, or 99% identical to SEQ ID NO: 2, and a second nucleic acid which encodes a polypeptide which functions as a component of the lysine biosynthesis pathway. In this embodiment, the first nucleic acid regulates transcription of the second nucleic acid.

Yet another embodiment of the invention provides an isolated polynucleotide comprising a first nucleic acid, the sequence of which is at least 90%, 91%, 92%, 93%, 94%, 95%, 96%, 97%, 98%, or 99% identical to SEQ ID NO: 3; and a second nucleic acid which encodes polypeptide which functions as a component of an amino acid biosynthesis pathway, preferably a lysine biosynthesis pathway. In this embodiment, the first nucleic acid regulates transcription of the second nucleic acid.

Further embodiments of the invention provide isolated *Corynebacterium* chromosomes with a first nucleic acid integrated into the chromosome, the sequence of which is one of the following: a sequence which is at least 90%, 91%, 92%, 93%, 94%, 95%, 96%, 97%, 98%, or 99% identical to SEQ ID NO:1; a sequence of which is at least 90%, 91%, 92%, 93%, 94%, 95%, 96%, 97%, 98%, or 99% identical to SEQ ID NO:23, a sequence of which is at least 90%, 91%, 92%, 93%, 94%, 95%, 96%, 97%, 98%, or 99% identical to SEQ ID NO:30, or a sequence which is identical to either SEQ ID NO:26 or SEQ ID NO:27. In the embodiments where the integrated first nucleic acid has a sequence identical to either SEQ ID NO:26 or SEQ ID NO:27, the isolated chromosome also has a third nucleic acid integrated therein, the sequence of which is at least 90%, 91%, 92%, 93%, 94%, 95%, 96%, 97%, 98%, or 99% identical to SEQ ID NO:28, operably linked to a transcription control region, wherein the nucleic acid encodes a polypeptide at least 90%, 91%, 92%, 93%, 94%, 95%, 96%, 97%, 98%, or 99% identical to SEQ ID NO:29. In these embodiments, the isolated *Corynebacterium* species chromosome also has a second nucleic acid integrated therein, wherein said second nucleic acid encodes polypeptide which functions as a component of an amino acid biosynthesis pathway, preferably, a lysine biosynthesis pathway. Additionally in these embodiments, the first nucleic acid regulates transcription of the second nucleic acid.

In another aspect of the above embodiments, a *Corynebacterium* species host cell comprising a *Corynebacterium* species chromosome as described above is provided, preferably a host cell derived from *Corynebacterium glutamicum, Brevibacterium flavum*, and *Brevibacterium lactofermentum*. In a related aspect, a method of producing such a *Corynebacterium* species host cell is provided, which comprises transforming *Corynebacterium* species cells with a vector comprising a first nucleic acid as described above, wherein said vector facilitates integration of the first nucleic acid into the chromosome of said *Corynebacterium* species cells, and selecting the host cell in certain preferred embodiments, the vector also comprises the second nucleic acid described above, and/or the third nucleic acid described above, with the first nucleic acid being physically situated to regulate transcription of the second nucleic acid. These vectors are also provided.

Examples of amino acid biosynthesis pathways which may be included in the above embodiments of the invention are the enzymatic pathways that result in the synthesis of L-glycine, L-alanine, L-leucine, L-methionine, L-phenylalanine, L-tryptophan, L-lysine, L-glutamine, L-glutamic acid, L-serine, L-proline, L-valine, L-isoleucine, L-cysteine, L-tyrosine, L-histidine, L-arginine, L-asparagine, L-aspartic acid, and L-threonine.

In those embodiments where the second nucleic acid encodes a component of the L-lysine biosynthesis pathway, the second nucleic acid may encode one or more of the following enzymes: aspartokinase, aspartate beta-semialdehyde dehydrogenase, diaminopimelate dehydrogenase, diaminopimelate decarboxylase, dihydrodipicolinate synthetase, dihydrodipicolinate reductase, or pyruvate carboxylate.

In another embodiment of the present invention, a method is provided for producing a vector. More specifically, the method comprises inserting into a vector any of the isolated polynucleotides described herein.

In another embodiment of the present invention, a vector is provided comprising any of the isolated polynucleotides described herein.

In one aspect of this embodiment, the vector further comprises a multiple cloning region into which a heterologous second nucleic acid can be inserted, thereby allowing for the regulated and/or elevated expression of a variety of second nucleic acids therein.

In another aspect of this embodiment, said vector is a shuttle vector. As used herein, the term "shuttle vector" refers to a vector that can replicate and be maintained in more than one host cell species. In a preferred aspect of this embodiment, said shuttle vector can replicate and be maintained in a *Corynebacterium* species host cell, preferably a host cell derived from *Corynebacterium glutamicum, Brevibacterium flavum*, and *Brevibacterium lactofermentum*, and in an *E. coli* host cell.

In another embodiment of the present invention, a method of producing a transformed *Corynebacterium* species host cell is provided. The method of this embodiment comprises introducing into *Corynebacterium* species cells, preferably *Corynebacterium glutamicum, Brevibacterium flavum*, or *Brevibacterium lactofermentum* cells, a vector comprising any of the isolated polynucleotides described herein.

In one aspect of this embodiment, the polynucleotide, after being introduced into the host cell, is integrated into the chromosome of the host cell. In another aspect of this embodiment, the polynucleotide, after being introduced into the host cell, is maintained as an extrachromosomal element; i.e., it does not integrate into the chromosome of the host cell.

In another embodiment of the invention, a method is provided for the production of a biosynthetic product such as an amino acid, a purine nucleotide, or a heterologous polypeptide. According to this embodiment, a transformed *Corynebacterium* species host cell harboring a vector of the invention is used. More specifically, the vector comprises any isolated polynucleotide described herein.

In a preferred aspect of this embodiment, the polynucleotide comprises a first nucleic acid which regulates transcription of a second nucleic acid, where the second nucleic acid encodes a polypeptide which functions in an amino acid biosynthesis pathway, as described above. In this aspect, the first nucleic acid regulates transcription of the second nucleic acid, thereby resulting in elevated production of the amino acid by the transformed host cell.

In another aspect of this embodiment, the polynucleotide comprises a first nucleic acid which regulates transcription of a second nucleic acid, where the second nucleic acid encodes a component of a purine biosynthesis pathway. In this aspect, the first nucleic acid regulates transcription of the second nucleic acid, thereby resulting in elevated production of the purine by said transformed host cell.

In yet another aspect of this embodiment, the polynucleotide comprises a first nucleic acid which regulates transcription of a second nucleic acid, where the second nucleic acid encodes a heterologous polypeptide. In this aspect, the first nucleic acid regulates transcription of the second nucleic acid, thereby resulting in elevated production of the heterologous polypeptide by said transformed host cell.

In certain preferred aspects of this embodiment, the first nucleic acid comprises a promoter. Preferred promoters include, but are not limited to the following types of promoters: a constitutive promoter, an inducible promoter, a derepressable promoter, a heat sensitive promoter, and a cold sensitive promoter.

Where the promoter is an inducible promoter, the method for the production of a biosynthetic product as above may further comprise adding an inducer to the culture medium. The inducer may be present throughout the growth of the host cell, or alternatively, may be added to the culture medium after the host cell has grown to an optimal density. In a preferred aspect, the host cell is self-induced, i.e., the inducer is produced by said host cell at some point during its growth cycle. When the inducer is present in the culture medium, the first polynucleotide facilitates enhanced production of the biosynthetic product. Inducers which may be used in the invention include, but are not limited to acetic acid, pyruvate, ethanol, starch subunits, sugars, cellulose subunits, fatty acids, and triglycerides. Sugars that may be used as inducers in the present invention include, but are not limited to fructose, maltose, lactose, and arabinose.

Where the promoter is a derepressable promoter, the method for the production of a biosynthetic product as above may further comprise use of a culture medium which lacks a suppressor. In this aspect, the suppressor may be absent from the culture medium throughout the growth of said host cell, or the host cell may be initially cultured in a culture medium containing the suppressor, and be transferred to a culture medium lacking said suppressor when the host cell culture has reached an optimal density. In certain preferred aspects, the host cell may be self-regulating, i.e., the suppressor may be removed from said culture medium through metabolic depletion by the host cell. When the suppressor is removed or depleted from the culture medium, the first polynucleotide facilitates enhanced production of the biosynthetic product. Suppressors which may be used in the invention include, but are not limited to purines, pyrimidines, amino acids such as histidine, and oxygen.

Where the promoter is a heat sensitive promoter or a cold sensitive promoter, the method for the production of a biosynthetic product as above may comprise adjustment of the temperature of the growth medium to a temperature which is greater than or less than the optimal growth temperature for an untransformed *Corynebacterium* species cell. For example, the yield of the biosynthetic product may be increased when said host cell is grown at a temperature adjusted to be greater than the optimal growth temperature for an untransformed *Corynebacterium* species cell, or the yield of the biosynthetic product may be increased when the host cell is grown at a temperature adjusted to be less than the optimal growth temperature for an untransformed *Corynebacterium* species cell.

DETAILED DESCRIPTION OF THE INVENTION

The present invention relates to isolated polynucleotides that function as transcriptional regulators, in particular, promoters, in *Corynebacterium* species host cells, preferably *Corynebacterium glutamicum*, *Brevibacterium flavum*, or *Brevibacterium lactofermentum* host cells, even more preferably *C. glutamicum*. host cells. These promoters are useful for regulating and enhancing the production of a variety of products in such host cells. Sources of promoters include nucleotide sequences from the 5' end of native chromosomal genes from *Corynebacterium* species, from sequences on plasmids that replicate in *Corynebacterium* species, from sequences in the genome of phage that infect *Corynebacterium* species, from sequences derived from other microorganisms, e.g., *Escherichia coli*, or from sequences assembled by humans (tac, trc) which are not found in nature. Genes of ribosomal proteins, ribosomal RNAs and elongation factors show high levels of expression. The promoters of these genes are candidates for increasing expression of amino acid biosynthetic pathway genes.

Another reason for changing promoters of genes in biosynthetic pathways is to make the pathway independent of factors that control the pathway in the wild type organism. For example the native promoter of the operon that contains diaminopimelate decarboxylase of the lysine biosynthetic pathway of *C. glutamicum* can respond to arginine or lysine in the growth medium. Arginine increased transcription three-fold and lysine decreased transcription by one third (Oguiza, et al., *J Bact.* 175:7356–7362 (1993)). Diaminopimelate decarboxylase activity decreased 60% in cells grown in minimal medium supplemented with 10 mmM lysine (Cremer, et al, *J Gen Microbiol.* 134:3221–3229 (1988)). Replacing the promoter of lysA which encodes the diaminopimelate decarboxylase is one way to make lysine biosynthesis independent of arginine and lysine levels in media.

Gene expression from many of the transcriptional regulators of the present invention can be easily and inexpensively regulated by manipulating the composition and/or temperature of the medium in which cells containing these promoters are cultured. Regulated expression from a promoter is especially useful for controlling the production of a gene product that is toxic to cells at high levels. To allow for maximum production of a gene product, a culture of cells possessing the gene of interest under the control of an inducible promoter can be first grown to a sufficient cell density under conditions in which expression from the promoter is suppressed. Then, by manipulating the culture medium, expression from the promoter is induced. This strategy assures not only a high level of gene expression in the individual cells, but also a sufficiently high number of cells in the culture, so that maximum production of the gene product by the entire cell population is achieved.

A. Definitions

In order to provide a clear and consistent understanding of the specification and claims, including the scope to be given such terms, the following definitions are provided. It is also to be noted that the term "a" or "an" entity, refers to one or more of that entity; for example, "a polynucleotide," is understood to represent one or more polynucleotides. As such, the terms "a" (or "an"), "one or more," and "at least one" can be used interchangeably herein.

Auxotroph. As used herein, the term refers to a strain of microorganism requiring for growth an external source of a specific metabolite that cannot be synthesized because of an acquired genetic defect.

Amino Acid Supplement. As used herein, the term refers to an amino acid required for growth and added to minimal media to support auxotroph growth.

Chromosomal Integration. As used herein, the term refers to the insertion of an exogenous DNA fragment into the chromosome of a host organism; more particularly, the term is used to refer to homologous recombination between an exogenous DNA fragment and the appropriate region of the host cell chromosome.

*Corynebacterium* species. As will be understood by those skilled in the art, the terms "*Corynebacterium*" or "*Corynebacterium* species" includes those organisms previously identified in the literature as "*Brevibacterium* species," for example *Brevibacterium flavum* and *Brevibacterium lactofermentum* which have now been reclassified into the genus *Corynebacterium*. (*Int. J. Syst. Bacteriol.* 41: 255 (1981)). Accordingly, the term "*Corynebacterium* species" is used herein interchangably with "*Corynebacterium* species and *Brevibacterium* species."

Enhancers. As used herein, the term refers to a DNA sequence which can stimulate promoter activity and may be an endogenous element or a heterologous element inserted to enhance the level, i.e., strength of a promoter.

Inducer. As used herein, the term "inducer" refers to molecule which acts to stimulate transcription from an inducible promoter. The inducer may be produced by a host cell, or added to a culture medium in which the host cell is being grown.

Isolated Polynucleotide. As used herein, the term is intended to mean a polynucleotide, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate, is not "isolated" for the purposes of this invention. Isolated RNA molecules include in vivo or in vitro RNA transcripts of the DNA molecules of the present invention. Isolated nucleic acid molecules according to the present invention further include such molecules produced synthetically.

Lysine Biosynthetic Pathway Protein. As used herein, the term "lysine biosynthetic pathway protein" is meant to include those peptides, polypeptides or proteins, and enzymes, which are directly involved in the synthesis of lysine from aspartate. These proteins may be identical to those which naturally occur within a host cell and are involved in the synthesis of lysine within that host cell. Alternatively, there may be modifications or mutations of such proteins, for example, the proteins may contain modifications or mutations which do not significantly affect the biological activity of the protein. For example, the natural protein may be modified by mutagenesis or by introducing or substituting one or more amino acids, preferably by conservative amino acid substitution, or by removing non-essential regions of the protein. Such modifications are readily performed by standard techniques. Alternatively, lysine biosynthetic proteins may be heterologous to the particular host cell. Such proteins may be from any organism having genes encoding proteins having the same, or similar, biosynthetic roles.

Mutagenesis. As used herein, the term refers to a process whereby a mutation is generated in DNA. With "random" mutagenesis, the exact site of mutation is not predictable, occurring anywhere in the genome of the microorganism, and the mutation is brought about as a result of physical damage caused by agents such as radiation or chemical treatment. rDNA mutagenesis is directed to a cloned DNA of interest, and it may be random or site-directed.

Mutation. As used herein, the term refers to a one or more base pair changes, insertion or deletion in the nucleotide sequence of interest.

Operably Associated. As used herein, the term "operably associated" refers to a association of nucleic acid elements in a functional relationship. A nucleic acid is "operably associated" when it is placed into a functional relationship with another nucleic acid sequence. For instance, a promoter or enhancer is operably associated with a polypeptide coding region if it affects the transcription of the polypeptide coding region. Operably associated means that the nucleic acids being associated are typically close together or contiguous and, where necessary, join two polypeptide coding regions, contiguous and in reading frame. However, since enhancers generally function when separated from the promoter by several kilobases, some polynucleotide elements may be operably associated but not close together or contiguous.

Operon. As used herein, the term refers to a contiguous portion of a transcriptional complex in which two or more open reading frames encoding polypeptides are transcribed as a multi-cistronic messenger RNA, controlled by a cis-acting promoter and other cis-acting sequences necessary for efficient transcription, as well as additional cis acting sequences important for efficient transcription and translation (e.g., mRNA stability controlling regions and transcription termination regions).

Parental Strain. As used herein, the term refers to a strain of host cell subjected to some form of treatment to yield the host cell of the invention.

Phenotype. As used herein, the term refers to observable physical characteristics dependent upon the genetic constitution of a host cell.

Promoter. As used herein, the term "promoter" has its art-recognized meaning, denoting a portion of a gene containing DNA sequences that provide for the binding of RNA polymerase and initiation of transcription and thus refers to a DNA sequence capable of controlling the expression of a coding sequence or fictional RNA. Promoter sequences are commonly, but not always, found in the 5' non-coding regions of genes, upstream of one or more open reading frames encoding polypeptides. Sequence elements within promoters that function in the initiation of transcription are often characterized by consensus nucleotide sequences. The promoter sequence includes proximal and more distal upstream elements. Examples of proximal elements in bacterial promoters include a −10 region and a −35 region, which are discussed in more detail, infra. Examples of more distal elements include operator regions and enhancer regions. As used herein, the term "endogenous promoter" refers to a promoter sequence which is a naturally occurring promoter sequence in that host microorganism. The term "heterologous promoter" refers to a promoter sequence which is a non-naturally occurring promoter sequence in that host microorganism. The non-naturally occurring promoter sequence may be from any prokaryotic or eukaryotic organism. A synthetic promoter is a nucleotide sequence, having promoter activity, and not found naturally occurring in nature.

Promoters may be derived in their entirety from a native gene, or be hybrid promoters. Hybrid promoters are composed of different elements derived from different promoters found in nature, or even comprise synthetic DNA segments. Hybrid promoters may be constitutive, inducible or environmentally responsive.

Useful promoters include constitutive and inducible promoters. Many such promoter sequences are known in the art. See, for example, U.S. Pat. Nos. 4,980,285; 5,631,150; 5,707,828; 5,759,828; 5,888,783; 5,919,670, and, Sambrook, et al., Molecular Cloning: A Laboratory Manual, 2nd Ed., Cold Spring Harbor Press (1989). Other useful promoters include promoters which are neither constitutive nor responsive to a specific (or known) inducer molecule. Such promoters may include those that respond to developmental cues (such as growth phase of the culture), or environmental cues (such as pH, osmoticum, heat, dissolved gases, or cell density).

Examples of environmental conditions that may effect transcription by inducible promoters include anaerobic conditions, elevated temperature, reduced temperature, or the presence of light. It is understood by those skilled in the art that different promoters may direct the expression of a gene in different cell types, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical or similar promoter activity.

Relative Growth. As used herein, the term refers to a measurement providing an assessment of growth by directly comparing growth of a parental strain with that of a progeny strain over a defined time period and with a defined medium.

Stringent Hybridization Conditions. As used herein, the term "stringent hybridization conditions" is intended to mean overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

Suppressor or Repressor. As used herein, the terms "suppressor" or "repressor" refer to molecules which act to block or reduce transcription from an derepressable promoter. The suppressor or repressor may be produced by a host cell, or added to a culture medium in which the host cell is being grown. Furthermore, during the growth of a host cell, the suppressor substance can be metabolized by the host cell, thereby removing it from the culture medium, thereby increasing transcription from the derepressable promoter.

Transcription factor. As used herein, the term "transcription factor" refers to RNA polymerases, and other proteins that interact with DNA in a sequence-specific manner and exert transcriptional regulatory effects. Transcriptional factors may be transcription inhibitory proteins or transcription activator proteins. In the context of the present invention, binding sites for transcription factors (or transcription complexes) are often included in the transcriptional regulatory element(s).

Transcription factor recognition site. As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Transcription factor recognitions sites which bind transcription inhibitory proteins or transcription activator proteins are also referred to as "operator regions." Typically, transcription factor binding sites can be identified by DNA footprinting, gel mobility shift assays, and the like, and/or can be predicted on the basis of known consensus sequence motifs, or by other methods known to those of skill in the art.

Transcriptional Complex. As used herein, the term "transcriptional unit" or "transcriptional complex" refers to a polynucleotide that comprises one or more coding regions for polypeptides, a cis-acting linked promoter and other cis-acting sequences necessary for efficient transcription of the structural sequences, distal regulatory elements necessary for appropriate transcription of the structural sequences, and additional cis sequences important for efficient transcription and translation (e.g., mRNA stability controlling regions and transcription termination regions). In bacteria, a transcriptional complex may comprise a single coding region, or one or more coding regions, e.g., as part of an operon.

Transcriptional Regulatory Element. As used herein, the term "transcriptional regulatory element" refers to a DNA region which activates transcription alone or in combination with one or more other DNA regions. A transcriptional regulatory element can, for example, comprise a promoter, response element, negative regulatory element, silencer element, gene suppressor, transcription terminator, and/or enhancer.

B. Microbiological and Recombinant DNA Methodologies

The invention as provided herein utilizes some methods and techniques that are known to those skilled in the arts of microbiology and recombinant DNA technologies. Methods and techniques for the growth of bacterial cells, the introduction of isolated DNA molecules into host cells, and the isolation, cloning and sequencing of isolated nucleic acid molecules, etc., are a few examples of such methods and techniques. These methods and techniques are described in many standard laboratory manuals, such as Davis et al., *Basic Methods In Molecular Biology* (1986), J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E.

F. Fritsch and T. Maniatis, *Molecular Cloning: A Laboratory Manual*, 2d ed., Cold Spring Harbor Laboratory Press, Cold Spring Harbor, N.Y. (1 989); P. B. Kaufman et al., *Handbook of molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989), all of which are incorporated herein by reference in their entireties.

Unless otherwise indicated, all nucleotide sequences newly described herein were determined using an automated DNA sequencer (such as the Model 373 from Applied Biosystems, Inc.). Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

C. Polynucleotides

Certain embodiments of the present invention are directed to an isolated polynucleotide comprising a first nucleic acid, the sequence of which is related to, or identical to, a nucleotide sequence, or fragment thereof, selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:26, SEQ ID NO:27, SEQ ID NO:28, and SEQ ID NO:30. SEQ ID NOs 1–3 have been previously described. See, e.g., Reinscheid et al., *Microbiology* 145:503 (1999); U.S. Pat. No. 5,700,661; and U.S. Pat. No. 5,965,391. SEQ ID NOs 23, 24, 26, 27, 28, and 30 have been previously described. See, e.g., Ben-Samoun et al., *FEMS Microbiology Letters* 174:125–130 (1999), Brosius, J. et al., *J. Biol. Chem.* 260,3539–3541 (1985), Amann, E., et al., *Gene* 69: 301–315 (1988), Moeckel, et al., *J. Bacteriol.* 174:8065–8072 (1992), Keilhauer, et al *J. Bacteriol* 175:5595–5603 (1993) and Patek et al., *Appl. Env. Microbiol.*, 60:133–140 (1994). Isolation of polynucleotides comprising nucleic acids the sequence of which are identical to SEQ ID NOs4–22 are described herein. While not being bound by theory, it is believed that polynucleotides having these sequences can be used to regulate gene expression in *Corynebacterium* species. The genes regulated by SEQ ID NOs 4–22, determined by similarity of the genes to genes identified in other organisms, are listed in Table 1A, along with putative exogenous regulatory molecules. SEQ ID NOs 1–22 are listed in Table 1B.

TABLE 1A

Nucleotide sequences that can be used to regulate gene expression

| Seq. I.D. NO: | Gene* | Regulatory Molecule‡ |
|---|---|---|
| 1 | pta | acetate |
| 2 | aceA | acetate |
| 3 | aceB | acetate |
| 4 | adh | ethanol |
| 5 | aldB | ethanol |
| 6 | poxB | pyruvate |
| 7 | ldh | pyruvate |
| 8 | amyE | carbon |
| 9 | malZ | carbon |
| 10 | bglX | carbon |
| 11 | gam | carbon |
| 12 | glgX | carbon |
| 13 | hisD | histidine |
| 14 | pyrR | pyrimidine |
| 15 | purD | purine |
| 16 | hrcA | temperature |
| 17 | htpX | temperature |
| 18 | dnaK | temperature |
| 19 | ctc | temperature |
| 20 | grpE | temperature |
| 21 | clpB | temperature |
| 22 | narA | oxygen |

Sequence I.D. NOs 1, 2, and 3 have been previously described. The remaining sequences were discovered in ADM's *Corynebacterium glutamicum* genome sequencing project.
*Putative genes regulated by sequence I.D. NOs 4–22 were determined by homology to genes identified in other organisms, e.g., *Escherichia coil* or *Bacillus subtilis*.
‡Putative regulatory molecules associated with the regulatory regions of SEQ I.D. NOs 4–22 were determined by analogy to regulatory regions identified in other organisms.

TABLE 1B

Nucleotide sequences that can be used to regulate gene expression

CACCGACAACGGCAACACGCAAAGGGCGAGACATATA SEQ ID NO:1

AAGTTCGATTCCTTAAAGGGGTTCTAAAAAATGTGGA

GTATGTGAGCGGGGTTCCACTAGTAGATTCGACTCCT

ATCGGGGTGCGACTGCTAATGGTGCCCTGCTATCAAC

CCTCCATGATACGTGGTAAGTGCAGACTAATAAAGGC

CAGTCGGGGAGGATTGGGGGCTTTGCTGGGGGCAGAT

TTGTCACGCTGCGCGCTTTCATAGACCCCATTAATGT

GGGGTGAAGAGCTGTAAAGTACCGCTAAAAACTTTGC

AAAGGGTGCTTCGCAACTTGTAACCGCTCCGTATTGT

TTTCTACGGCAATAAGCATTTGTGCTGCTCAAAGCGT

GGAATTGAGATCGGTTTGAAAATTACAAAATAAAACT

TTGCAAACCGGCTGTACGCAAGGCGGACGAACGCTA

AACTATGTAAGAAATCACAACTTCCCCTCAGTAGTGC

CAGGAGGCACAAGCCTGAA

ACTCTTTTAAGAAAAGCACTCTGACTACCTCTGGAAT SEQ ID NO:2

CTAGGTGCCACTCTTCTTTCGATTTCAACCCTTATCG

TGTTTGGCGATGTGATCAGACTAAGTGATCACCGTCA

CCAGCAAAAGGGGTTTGCGAACTTTACTAAGTCATTA

CCCCCGCCTAACCCCGACTTTTATCTAGGTCACACCT

TABLE 1B-continued

Nucleotide sequences
that can be used to regulate gene expression

TCAAAACCTACGGAACGTTGCGGTGCCTGCATTTTCC

CATTTCAGAGCATTTGCCCAGTACATCTGTACTAGCA

ACTCCCCCGCCCACTTTTTCTGCGAAGCCAGAACTTT

GCAAACTTCACAACAGGGGTGACCACCCCCGCACAAA

ACTTAAAAACCCAAACCGATTGACGCACCAATGCCCG

ATGGAGCAATGTGTGAACCACGCCACCACGCAAACCG

ATGCACATCACGTCGAAACAGTGACAGTGCATTAGCT

CATACTTTGTGGTTGGCACCGCCCATTGCGAATCAGC

ACTTAAGGAAGTGACTTTG

TTGCGTGGTGGCGTGGTTCACACATTGCTCCATCGGG SEQ ID NO:3

CATTGGTGCGTCAATCGGTTTGGGTTTTTAAGTTTTG

TGCGGGGTGGTCACCCCTGTTGTGAAGTTTGCAAAG

TTCTGGCTTCGCAGAAAAAGTGGGCGGGGGAGTTGCT

AGTACAGATGTACTGGGCAAATGCTCTGAAATGGGAA

AATGCAGGCACCGCAACGTTCCGTAGGTTTTGAAGGT

GTGACCTAGATAAAAGTCGGGGTTAGGCGGGGGTAAT

GACTTAGTAAAGTTCGCAAACCCCTTTTGCTGGTGAC

GGTGATCACTTAGTCTGATCACATCGCCAAACACGAT

AAGGGTTGAAATCGAAAGAAGAGTGGCACCTAGATTC

CAGAGGTAGTCAGAGTGCTTTTCTTAAAAGAGTTTTC

ACAACCGTTAACGGCGTAGCCAAACAAGAAGGATTCG

CATTCTTCTGGTTTAGGCACAGGTCATCTAAACCCAT

GCTTTAAAAGGAGCCTTCA

ATTGGAAAATGGAGATTAGAAGAATCCTGGGAATGTT SEQ ID NO:4

GGTGTGTGTTGCATGTCTGTTGAGACTATCTAGTAGA

TGCGGCTGCGCTCCTTAATTGCATGCTGGGGTGGTGG

GGAATGGGTGGTTGGGGCGTCGAAAAGCATTTTTGG

TGCTTCTAAGCGAATTGTGTGAATCTTGGAAACCTAA

TTGAAAAACATTCCCATTAGTGGGTGATTTGCTGGAG

TTTTGTGAATCTATTTTTCGAAATTTCAGCGTGCGGG

GGTGGTTTGTTTTTTTACAATTGCCAGTTCATTCACG

GTTGTTGAAATGTTCGGGGTAATAACTCAACTTTCT

ATTTTCACCTTGTTGGGATTTCGCTAGGGTGGACGAT

GGCAGCAATTGAATGTTGTAAATCACACAATTGCAAG

GATTGTAATTTAAGGCACATCTATGTCGGTGTGAAAT

TACATGTGCCAGAAGAGCAATTTGCCAAGTAATCCAA

GCGAGAAGGAGTGAGTTTT

CGATCATCGAACTCGGCGAAGAAAACCGAAACCTCAA SEQ ID NO:5

TABLE 1B-continued

Nucleotide sequences
that can be used to regulate gene expression

AGAATCCCTGCGTAAGGTCACAGCTGAGAATGAGCAG

CTCAAAGATCAATTACGCAGCGGGCGTCCGCGTGGCG

AGCTGGTGCACGTGCCCCGCTCCACCGCGGTGGTCAT

GTGGGAACGCCGCAAGGGGCGTTCCAAGTAAAAACAT

GCTTGTCGACGCCGCTTTCTAGCAAATTAAGCGGGCA

CCTCCATTTATCTTTTGGAGGTGCCCGTTTCGTGCTT

TCGCCAATTAGATACATGCATAACCACCCGAACAGGG

GTAATAACTTTTGAAAGGCTTTCGGCGTTGAGCTGCG

AGAATTTTGAGAAAAGGGGGTGAATTTAACAGGGGTT

CTAGCGCGGATTGATTTTCGTGAATATGGTGGCTGCT

AAGCGTGCGAATGTGCGCGTTATCACAATCGTTGACC

AAGTGTCACCTGACGCACAGGTAGTGCTCAGGTGGAG

GTGGCCCAAAGGAGACCCA

TTTTAGACCACGGCGCTGTGTGGGGATTTAAGACGTC SEQ ID NO:6

GGAAATTGTAGGGGACTGTCAGTGTGAGTCGGGTTCT

TTGAGGCGCTTAGAGGCGATTCTGTGAGGTCACTTTT

TGTGGGGTCGGGGTCTAAATTTGGCCAGTTTTCGAGG

CGACCAGACAGGCGTGACAAGATTGACTAAAAAACCG

AAGTTTTGGCACGTGTGTTTGGTTTCTCGGGGTCTAA

ACCGGACAGGCGTGACAAGATCTGGCGAAATCGCAGG

TTTTTGTCACGCGTGTCTGGTTTTACCTTTTGGGGGC

CCGAACTGCCCTGAACTACTCGGATCGACCAAGCAGT

TTGGCCTCCAGCGCTCTGATCAAGCACCCAACCGCCT

CTAAATCACACCAAGGCACTCGTAAAACCCGTGGCAG

ATAGAGAAAGTGTGGCAGCAACTCGAATTGAAGAGCA

CAATTGAAGTCGCACCAAGTTAGGCAACACAATAGCC

ATAACGTTGAGGAGTTCAG

AAAACAGCCAGGTTAGCGGCTGTAACCCACCACGGTT SEQ ID NO:7

TCGGCAACAATGACGGCGAGAGAGCCCACCACATTGC

GATTTCCGCTCCGATAAAGCCAGCGCCCATATTTGCA

GGGAGGATTCGCCTGCGGTTTGGCGACATTCGGATCC

CCGGAACCAGCTCTGCAATGACCTGCGCGCCGAGGGA

AGCGAGGTGGGTGGCAGGTTTTAGTGCGGGTTTAAGC

GTTGCCAGGCGAGTGGTGAGCAAAGACGCTAGTCTGG

GGAGCGAAACCATATTGAGTCATCTTGGCAGAGCATG

CACAATTCTGCAGGGCATAGATTGGTTTTGCTCGATT

TACAATGTGATTTTTTCAACAAAAATAACACTTGGTC

TGACCACATTTTCGGACATAATCGGGCATAATTAAAG

TABLE 1B-continued

Nucleotide sequences
that can be used to regulate gene expression

GTGTAACAAAGGAATCCGGGCACAAGCTCTTGCTGAT

TTTCTGAGCTGCTTTGTGGGTTGTCCGGTTAGGGAAA

TCAGGAAGTGGGATCGAAA

CCAGATCTCGGGATGCTTCGTAGATCAGCATGGCGCC SEQ ID NO:8

GAGGTCGTTGGCTGCTGCACGGAAAGCTGCGTTGTCG

CTGCGCTCGTCGCGCAACAGGGGTAGGCGGCTAGCAA

CGAGTCGGTGGTTGACGATGGTGATGTCCATAGCTTC

ACATGTTAAATCATTGCCGCCCAGAAGAAGACCGCGC

GGGCGAATTTGGGCTTGGAGGGAACCAAACGGCCACT

TTTCCAGTCCAACAAAGTATGAGGATTAATTTGCCCC

ACTCCAAAGAGCTCGCCCACGAGCTGTGTTTGTTGCC

CACCCCTGCTGTGCCCGCCCTTCCCACTGATTCTGGC

GCGCAGTTTGATATCCACCAGGCACTGTCCGCCTCTC

TTGCCACCTATGCCCGCAACCTCACCTTGCTGTCCCA

CACCGCCGAGAATTTAGGAAACCGCGCTCTGACCGCC

CTCGCTGAAATCGAAGACACCGACGACCAACTCGCAC

ACGCATTGGAGCGCCTGAC

GGGCATCATGGGCATTGTTGGTGGATTCACCATGCCT SEQ ID NO:9

GTCGCAATCGCTAGGACCAGGGATAAGAACCTCGTGT

GGTTCCCCGTGGTCTTTGGTGCATCGATGTTCCTCGG

TTATGTGGGAACGTGGCTGTGGCCGTCCCAAGGCTGG

TACCTGTGGTCATTCCTTCTTGGTTTAGGTGGACTCT

GCTTCCCGATGGCTATCGCCCTGATTCCAGCGCGTAC

GAAAGATCCGAGAATTACCGCAAGCTTGTCTGGATTT

GTGCAGCCGGTGGGTTACATTCTTGCAGCCCTTGGGC

CATTGGCAGTGGGAGCGATCTACCAGGCGATTGGCTC

CTGGTCAGAGATCCTCGTTGGTTTGGCCTTGGGCACA

ATAGTGTTGTCGATTGTGGGATTCAGAGCAGCACGCA

ATGTGACGGTTGATGATGAATTGAGGAGATCAAAGTA

GCCTCAACTAAGCGTCGCGATAAGAACGAGGGCAAG

GCTGATGTACTCTGTCAACCATGGATAAACCGGTCGT

GAGGGATGCAGCTCTGCTGATTTTTCGCGCTGTGCTC

GGAGTGATCTTTGTGGCACACGGGTGGAAAAGCTGT

TCATCTCCGGAGTTACCAAGACAACAGGACAATTTTC

AGCCTGGGGAGTGCCTCAACCCAAGCTCTCGGTGTGG

ATCACATCGATCTCTGAGCTGCTCGGTGGTGCCTTCC

TAGTGGTTGGTTTGCTCACCACCTTTGTTGCTGGTGC

ATTAGCGCTGTTGATCGCCGCTGCTATTTACTTTGTG

TABLE 1B-continued

Nucleotide sequences
that can be used to regulate gene expression

CACTTGAGTTCGGGCTTTTTCACAGTTGATAACGGCA

TCGAATTCCCCTTGCTCATCATTGTTTCTTTGCTCGT

GATCGTTGTGTTTGGTTCTGGTAGAGCCAGCGTTGAT

GGGGTGCTCACGCGTGGTTGACTGTAGTGCCATTCAA

GCCGCGCTGTCCGCCAAATTAGATGGTGAGCCGACAG

GCTTGGATGATGCAGTAATTGAAGCGCACCTCGCTAA

TTGTGAAGAGTGCAGAAATTACTACAACCGTGCTGCT

GAGTTGAATCGGATGCTCAATTTTTGCGCCGCGGAAC

CTCGCACCCTGACCCCGCCTGATCTATCAGAGATCAT

TCTGGCAGAGGTGGAACCAGAATGGCGCAGGCATGCC

AACGCCAAGGTTGTGGGATCCCTGCTATCGCGAGTGT

TGTTGGTGATCCTGGGTGTGGTTTACCTCGCCTGGGG

TATCACAATGTTGGGGGATTCGGCGTCGATAAGCGTC

CAAGAAGACCCGCTCACCTCGCGCCTGCTCGCGGAGG

CCGTTGCCTACCGCATTGCTCTTTCTGTGGGGCTGTT

ATTTGCGGCGTGGAAGCCGCGGATTATCGCGGGCATG

CTCCCGATTTTTGGAACGTTGTGGACATTTAGTGCTG

GTTTTGCTGCGCGCGATCTCGTGTTTGGCGTCGCCGA

TTCACAGACGGGACTGTCCATTGGTCTGCTGTTGATT

TCTACGATTGTGCTGTCGTTTGCGTTGGTGAATAGTT

CTGGACCGGGTATTTTGCGGCGCACATGGAACTCATT

GAACGCCGCGCCCGGCTAAGGTGGGAGGC

TAATACGGCATCCGGCCTGAAAGGACAGTGTGGAACC SEQ ID NO:10

CAAAAATCATGCCCTCGCAGAATCGTGTTTAAGGGGT

TAAAACGCCTCGACCCACACTCTGACCCATCCGTGAA

ACTAGACCTCTTAAAACGACTTCTGGTTGGTGAGGTG

TGAAAACCGCACTGCGGGCCCAATTCACAAAAATCC

ATACGAGTGTGCACACCCGATTTTCACATCGCTTCGA

GACCTCCCTTTTTGACACCTTAATTGTCTAACCCCGT

ATAGGTGAGAAATGTTGGACAAGTGTCTGTTTTTGTG

GGGGGAATCTGACTACGATGGTAAGAAACAGGGAAAG

GGGTTACCATTATGTCTCAAGAGTAGCCTCAAATCGG

CTCCCGCCTCTCTCGTGTCATTGAACAAGACGGCCTA

CAATTCCGCGATCTCGACGGCGACGGCGTACTTGCAC

CTTATGAAGATTGGCGTCTAACCCCAGCAGAGCGTGC

CGCTGACCTGGTGAAACGA

CACCGCGTCGCCGATCTCTCCCTTCCAGACTCAGAAG SEQ ID NO:11

TTGCTTCGGCAATTGCACTTGAGTGGAAACCAGGCGT

TABLE 1B-continued

Nucleotide sequences
that can be used to regulate gene expression

CGGATTCACTACTTGAGCTGCTGATTTGTAGGTTTTA

AGACCTTGAAGATATAGTTAATTCTCGTTGCAAGGAA

CCAGATTCCAAGCAATGCGTATTCCTCCATAGCTCAG

TTGGCAGAGCATTCGACTGTTAATCGAAGGGTCACTG

GTTCGAGCCCAGTTGGAGGAGCAAATTGAAACCCACT

GTTTTTTAACAGTGGGTTTTTTTGCATGTTTCATACA

GTTAACGAACCCCAATTTTGTAACTTCCACTCTCCTA

GCTATGATGAATACTCGTTGCAAGGAAGTAATTCCTT

TCCAATACTTATTCCTCCATAGCTCAGTTGGCAGAGC

ATTCGACTGTTAATCGAAGGGTCACTGGTTCGAGCCC

AGTTGGAGGAGCAATACACACAGCCCGCCGTTTTTCT

TAAAACGGCGGGTTTTGTT

GGTGTCAGTGTATCCGCGAACCAGAGCCTCGATGGCA SEQ ID NO:12

GCTGTGTCTTCTGGGGAAGCGGTCTGGCCGTTTTCAA

CTGGCGCAGCTTCAGCGAAGGTAATTGGGTTCTCAGA

CAGCTCTTGTGACAGTACATCAAGCTGTGCTTGCTGC

TCTTCGTTGATGGTTGTTGCTTCGGAAGATTCAGATT

CAGATTCAGATTCGGACGAGGTGGTTTCTGCTGCTTC

CGCCGAGGTCGTTGCGCTGGAAGAGGAAGAATTTGTC

GTCGTCGCTGCGCTGGATGAGGCTGCTTCTGTATCAG

ATGACTCACTGCTACATGCGGTTAAGAGAAGTGGGGT

GACCATGAGTGCTGCGAAAGCAGCCTTCTTTGAGGAA

AGGCGAATAGACAAAGTTCTGCTCCTGATAAATCATC

GACATGCTCCGGAAAACTTAAAAATTCCCGGACGGTT

CACGCAGATTACCCTAGCAAAGCAATCTAGCTGACGA

CCCAATTTAGTCCTGTCATTATGCTGGCAATTGTGCA

GCTATCTAAAGAATCTATTATTGGGGCAGCCGTTTCG

ATCCTGAGCGAGTTCGGTTTGTCGGATATGACCATGC

GTCGCGTCGCAAAGCAATTAAATGTCGCGCCGGGCGC

GCTGTATTGGCATTTTAAAAATAAGCAGGAGCTTATC

GACGCCACCTCACGCCATCTCCTGGCGCCTATCTTGG

GGCGCAACGACGAGCAGCGAGCAAGCATTTCCGCGCA

GGAAACGTGCGCAGAAATGCGTTCACTGATGATGCAA

ACCAAAGACGGTGCGGAAGTCATCAGTGCCGCACTGA

GTAATCAGCAACTGCGCCAAGAATTGGAATCTCTCAT

TTCCGACTCTTTAAAAGAACCTAATGAGGTCGGTGCT

TTTACGCTGCTGCATTTTGTGGTGGGTGCAGTATTAA

CAGAACAAACTCAGCTGCAGATGCACGAGTTCACGGC

TGGCGCGGAAGATGACACACAAGAAAACCCTGCCGAT

GCGAACTTTGAGGAGAGATTCAATCAAGGATTAGAAA

TCATTCTGGCGGGTCTAGACGCGCTTGGGCATATAAG

ATAGCGTTCT

AGTGACAGCTCGCGCCGCATCGTTGATGGCAAACATG SEQ ID NO:13

TCCAAATTAAGGCGCATGCGACCAAGGATGGTGAGCA

TTTGCCCTGATTCGTGGCTGAAGTACATCGAAATGCG

GTGATCTTGCCACGGCACGATGATGCGATCTTCTGAG

CTCAAATAGTGGTAGCCCAAGGAATCAACAGCCTCCG

TCACTCGATTCAGGTCAACTGGGAAAGGAATGGAGGT

GTTGGGTGCAGGGACGTTTCGATCATTCACAGAGGTG

AAATCCATTCCTTCCAGTATCTCAAAGGTGAAAGCGG

GTTTAATTCAGGTAAATCTGGGGTGGTCATTTTAAGT

TTTAAGTCTAATTCAAATGAACTCTGATGTACCCAAA

TCAGAAACTTGTTACGTGGGGAATACAATAGGTAAAT

ATGCGGGCTTAAGAACTTGTGTTGAGGCCGCTTGGAT

TCGGGCACCGAGCTCGAAGAATTTCGATTCAACCTTT

TAAGGGAGAACTTTTCGCC

CGTGGCGTGCCACCCATTTAAGTCCCGCGGGGAGACT SEQ ID NO:14

GAAGATGGTGGTGCCGTCGGCGAGGCGTTCTGCCTGC

GTAATGGGGTTAAGTGGGATGAACGGGGGAGTCAGAC

GTGCGACAGCGCCCTTGCGGGTATGCCAATCCCAGAC

CATTTCTCGGGAAAAGGAATAAAATGGCTTGTGGTC

AGACTCACAGGGGCTTCTCCAAGTCAGTGGATTTATG

AGGTCCCAGTGGGTACACACCGGGTGTCCTACAACGA

TCAATTGTCACAGATTCGACTGGCATGCTGTACCATC

TGCTTTAAGCATTTTGGTGTTTCACTGTTGTTAACAG

TGTTTCACCGTGGAGCACTACCTTAGATCATAGTCAG

CATCTTGGGGTGAATGTGACACGGTACGCTATAGTGT

CAGACAACAACCAGGAAACTGGTCGTTGCAGAGTTTT

TGCAAAATTGGACATCCTTTAACGGACCGCACAGAGA

GGCGGGGAAGGAGGTCACG

GCCATGGCGTTGCGGAAATCGTAATCGGCCATTTTGT SEQ ID NO:15

CGGTGGGAAGAGGTGGATGTGAGTGTGGGGAACATC

GAATCCTGCGATGATGTAACCACATCGAGGGGCGTCG

AATGCTGTGCGGATTGCATTTCCGATGAGCTGGGAGG

CCTCGTTTACTTCGCTCCAGATGTTCTGAGGAAGGTC

GGTCCAGCGGTCAACTTCTGCAACGGGTACGACTAGG

TABLE 1B-continued

Nucleotide sequences that can be used to regulate gene expression

GTGTGGCCGTAGGTGAGGGGTTCGATGGATAGAAAAG

CCACGACATTCTCGGAACGATACACAAATCGGCCGGG

GAGCTCGCCATTAATAATTTTCGTGAATACAGAAGCC

ATATGCACAGACTACTACTTGGCGTGCAACCAAATTG

AGGTTGCATAAAATAATGCAGGTGAGCCGGTCATTTT

AAGGCGCTTTTCGACGCCACTTTCAACCATTTCCGAA

CCGCCAAGAATACTGGAATAGCTTGGATCAAGTTTTG

CAGGATAAACTGTGCAACC

ACGCTGATCGTTTTGAGCTTATCGACGCTCGCCTGCG  SEQ ID NO:16

CTCAGCTGGTTTCGATTGGTACGAGGTATCCAACTGG

GCGAAACCCGGCGGAGAATGCAAGCACAACATGGGCT

ATTGGGTCGACGGCGACTGGTGGGGTGCTGGCCCGGG

CGCGCACTCGCACATCGGCGACCGCCGCTTCTACAAC

ATCAAGCACCCAGCGCGTTACTCCGCGCAGATTGCGG

CCGGCGAGCTGCCCATTAAGGAAACAGAGCGGCTGAC

GGCGGAAGATCACCACACCGAGCGCGTCATGCTTGGT

TTGCGCCTGAAACAAGGCGTGCCGCTGAACCTTTTCG

CACCCGCAGCGCGCCCGGTCATCGACCGTCATATCGC

AGGAGGCCTGCTGCACGTCAATGCGCTGGGCAACCTG

GCGGTGACCGATGCGGGACGTTTGCTTGCCGACGGCA

TCATCGCCGACATTTTGCTTAGTGAAGAAGACTAAAT

ATTTAGTAGGGTTACAGAC

TGGCGACTATGCCACATAGTCGACTACCTTGCATAGT  SEQ ID NO:17

TGACTATTTGATTGAGTTGAACTGTGTCAGTGTATGA

AGAGAAAAATGAAGAGAAAAACAGCTGCACATGGTTT

CAAAAGATAAGGAAGTGAAGCATGAGCATCGAGCCAG

GAATCCCCACGCTTGGACCGCTTGAAGAACAAGTCAT

GCACATTCTGTGGGATCACGGAAAATTGACAGTCCGT

GAAGTCATCGAATTCCTTCCAGGTGATCCTGCGTACA

CAACGATCGCAACCGTCCTGCGTCACTTGGGCAGAAA

AGGCATGGTCACCATTGTGAAAGATGGTCGGACTGCT

CGACACAGCGCGTTGATGAACAGGGAAGAATACACCG

CTGGCGTCATGGATCAGGTGCTGTCGACCAGTCGGGA

TCGCACCGCATCAATTCTGCATTTCGTGGATACGATC

ACGGCGACTGATCGCGAGCTGCTTCTGGAGTATCTGC

AACAGCAGGAGGGCAGGAA

AGACTTGGCGTCAAAGTTGAGTGGGACCTGTTGAAAA  SEQ ID NO:18

CAGCTCGTATCTTCCCTGATTGGGTGGTTGAAATTAG

GGGTAAACCCGGATTTTTTCTCAAGTGAAGCGCTTTG

ACCTGTGTAAATTAAGAAAGTTGAGTCTAGTGGGAAC

AACTTTGTGGCATTTACCGTTGCCATATATGTAAGCT

TGAGTCAGGCAGGCTCAATGAGGAGTTTTTCTTACCG

GCGAAAGTCGGTGGAAGCAAGTCAAAGCTCAAGCCGT

GGACAATACTAAAATCACCTAAAACAGGAGGCACCAT

T

CGGGAGCCGTTCTTCTCCACGATGGGCGCTCGGTGA  SEQ ID NO:19

AATCACTGAAACGCGCGGTTTCCAGAAGCATCACCAC

GATGGCGTCACTGACCTCAAAAGATGCAGTGTGCTCA

TCACTGAAGACGGTGTTTTCTTTGAAGCCAAGACCTG

CATAAAAAACGCTTAGATGCTGCAAGGTCAGATACTG

GTAGGTTGATGAAAATCATGTCGTGCTGAAGTCGTGC

CATGGGAGTTCCACTTCCTCAAAGTGCCTTTTGGCTA

ATGTGACCCCAACCAGTATGCTGCCGGTTTTTGGATT

AGGTTTGGCCATCGTGCTAGCATATTTAGGTCTCGGC

GAGGGTCAAGTACTTTTAGTGCTCAACCGTTATCGAC

GCGATCTAGACTTCTAAAGTGCACTTTTGTGCGCTGC

CTGCGAAGACTCGACCAAGACATTCGAGTCGGTCGCG

GGCATTTTTTATTTTCGCGGCCGAGTGTCCACCTTCA

TCCATGAGGAGAAATCACT

TGGATTGTCTGGCGGACAAAGTTCGCACCGATAAACC  SEQ ID NO:20

CGGCACCACCGGTCACAAGCAAAGAAGTCATGGTCGT

CATAGTAGTTGCGGCTCCTGCAGTTGCGCGTGTTATC

GCTGACGGGCATGTCAATTCAGCCGTGACCCAGCTTC

GGTGCGGTGTGAAAACGTATGGGAAAAGCCACGGAT

AGTGCATGCCCACTTCTCCACATGGGCTGTGCTCAGC

TGTCGTAGGGGCCACGGCTTGCGGACTTTCTGAACAC

CCGGACGAAAGCCTCCATTATTGATGGCACCCACCCG

GGGGTGGTATCGGTTGCTAAGTTCACAGTGGTCGGAG

AGAATAAGTCAGCACTTCTGATTACATGTACGAAATC

AGGGCGGTCAAATGCCAGTTCCCACCCGGCTTCACTA

AGGCGGGACGACCATAGAAACGCAGCTTCTGACATTG

AATGCGCCGGTTTGCTATGGACTACACCGCATATGAG

GAAAGGGCTTGAAACGCAC

CTTAATGAGTACGGCGTGGCTTATATCGGTTTCGCTC  SEQ ID NO:21

CGTTTGAAATCGGCATGACCATCATCGCGCCGATCGC

GGTGCTCGCAGGCTTTACTATGGGGTTGGGTTGGGCG

TABLE 1B-continued

Nucleotide sequences
that can be used to regulate gene expression

TCGTTGATTGTTGCCATCGTGATTTTTGGCCTCGCGT

GGGGTCTGAAGTGGTTGCCGGAGCGCGGACATGTCCG

CGGCGAGGGTAAGCCGCAATAAAGGTTGGAAGCGCCG

GGTCTAGGTCCGGCGCTTCTTTCGTACGCTTTTCGAC

GCCTCCCTCCACGTAATATTAAAGTTACGGGTTTTCC

CTGATGCTTAAGTGGTAGTCAGTGCTTAAACTTGACT

GCGGTCCACTCAATTTATTTTCAAATTTTTTGAACTT

GAGTGGAACATACTCAACTCTTTGTGCGTTATAGATA

TTAGAGAGTTAAATAATGGCGCTTGACCTGCAGGAAA

TTGAGATCAACACTGATTGTGTAGGTTGGCGCCCAAC

AAAGAAAGGGCGTTGAAAG

TGGCCATTCCTGTGGTCCATGCTCGCCCTGTTCTTCT   SEQ ID NO:22

TCACTGGACTGGGCAACGCCGGCACATTCAAACAAAT

GCCCATGATTTTGCCCAAACGCCAAGCAGGTGGCGTG

ATCGGCTGGACCGGTGCCATTGGTGCCTTCGGCCCCT

TCATTGTCGGTGTCTTGCTCTCCTTCACTCCAACTGT

CGCGTTCTTCTGGGGCTGCGTGGTGTTCTTCATCATC

GCCACCGCTTTGACCTGGATCTACTACGCCCGCCCGA

ACGCTCCATTCCCGGGATAAACCGAAAGGCCAATCCA

TGACTACAACTACTTCTTCTGGGAAGTCTTCTGAACA

GTCTTCTGAAAAGATCAACCCCCTCTTCAAGCTCGGC

AGTTTCCTAAGAAAAGGCACCGTCGGTTCTGAAGGCC

AGCAGATTTTCCTTCAGGGCGGACGCCAAGCCGATGT

GTTTTTATCGCAACCCGATGGGCGTTCGATAAAAGTC

GTGCGCTCCCACACATGGC

In certain embodiments, polynucleotides of the invention comprise a first nucleic acid, the sequence of which is at least 90%, 91%, 92%, 93%, 94%, 95%, 96%, 97%, 98% or 99% identical to a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or a complementary sequence thereof. Of course, this embodiment also encompasses a first nucleic acid, the sequence of which is identical to any of the recited nucleic acid sequences.

By a polynucleotide comprising a first nucleic acid, the sequence of which is at least, for example, 95% "identical" to a reference nucleotide sequence is intended that the first nucleic acid sequence is identical to the reference sequence except that the first nucleic acid sequence may include up to five mismatches per each 100 nucleotides of the reference nucleic acid sequence. In other words, to obtain a first nucleic acid, the sequence of which is at least 95% identical to a reference nucleic acid sequence, up to 5% of the nucleotides in the reference sequence may be deleted or substituted with another nucleotide, or a number of nucleotides up to 5% of the total nucleotides in the reference sequence may be inserted into the reference sequence. The reference (query) sequence may be any one of the entire nucleotide sequences shown in SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:22, or any fragment of any of these sequences, as described infra.

As a practical matter, whether any particular nucleic acid sequence is at least 90%, 91%, 92%, 93%, 94%, 95%, 96%, 97%, 98% or 99% identical to, for instance, a nucleotide sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or a complementary sequence thereof, can be determined conventionally using sequence analysis computer programs such as a OMIGA® Version 2.0 for Windows, available from Oxford Molecular, Ltd. (Oxford, U.K.). OMIGA uses the CLUSTAL W alignment algorithm using the slow full dynamic programming alignment method with default parameters of an open gap penalty of 10 and an extend gap penalty of 5.0, to find the best alignment between two nucleotide sequences. When using CLUSTAL W or any other sequence alignment program to determine whether a particular sequence is, for instance, 95% identical to a reference sequence according to the present invention, the parameters are set, of course, such that the percentage of identity is calculated over the full length of the reference nucleotide sequence such that gaps, mismatches, or insertions of up to 5% of the total number of nucleotides in the reference sequence are allowed.

This embodiment of the present invention is directed to polynucleotides comprising a first nucleic acid, the sequence of which is at least 90%, 91%, 92%, 93%, 94%, 95%, 96%, 97%, 98% or 99% identical to a nucleic acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or a complementary sequence thereof, irrespective of whether they have functional activity. This is because even where a particular polynucleotide does not have functional activity, one of skill in the art would still know how to use the nucleic acid molecule, for instance, as a hybridization probe, an S1 nuclease mapping probe, or a polymerase chain reaction (PCR) primer.

Preferred, however, are polynucleotides comprising a nucleic acid, the sequence of which is at least 90%, 91%, 92%, 93%, 94%, 95%, 96%, 97%, 98% or 99% identical to a nucleic acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or a complementary sequence thereof, which do, in fact, have functional activity, in particular, polynucleotides which are capable of regulating transcription in *Corynebacterium* species. Examples of polynucleotides which regulate transcription include promoters, operators, transcription factor recognitions sites, transcriptional complexes, and transcriptional regulatory elements, as described herein. Preferably, polynucleotides of the present invention comprise a promoter which functions in *Corynebacterium* species, preferably in *Corynebacterium glutamicum, Brevibacterium flavum*, or *Brevibacterium lactofermentum*, even more preferably in *C. glutamicum*. Assays to determine whether a polynucleotide is capable of regulating transcription in *Corynebacterium* species can be routinely performed using techniques described herein and otherwise known in the art.

Accordingly, the present invention also encompasses the above polynucleotide, further comprising a second nucleic acid. Preferably, the second nucleic acid encodes one or more polypeptides, and the physical location of the first nucleic acid relative to the second nucleic acid is such that, under the appropriate conditions, the first nucleic acid will operably regulate transcription of the second nucleic acid, thereby facilitating production of the one or more polypeptides. "Facilitation of production" includes increasing production constitutively, decreasing or blocking production except under specific conditions, and/or increasing production except under specific conditions. Among the "conditions" contemplated by the present invention are: (1) adding a component to a culture medium, (2) removing a component from a culture medium, (3) replacing one component of a culture medium with a second component, (4) increasing the temperature of the culture medium, (5) decreasing the temperature of the culture medium, and (6) regulating the atmospheric conditions (e.g., oxygen or nitrogen concentrations) in which the culture medium is maintained. Examples of such conditions are described in more detail, infra.

One particularly preferred aspect of this embodiment is a polynucleotide comprising a nucleic acid, the sequence of which is at least 90%, 91%, 92%, 93%, 94%, 95%, 96%, 97%, 98% or 99% identical to a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22; and a second nucleic acid, which encodes a component of an amino acid biosynthesis pathway. Examples of amino acid biosynthesis pathways included in this aspect of the invention are the enzymatic pathways that result in the synthesis of L-glycine, L-alanine, L-leucine, L-methionine, L-phenylalanine, L-tryptophan, L-lysine, L-glutamine, L-glutamic acid, L-serine, L-proline, L-valine, L-isoleucine, L-cysteine, L-tyrosine, L-histidine, L-arginine, L-asparagine, L-aspartic acid, and L-threonine.

A preferred amino acid biosynthesis pathway results in the synthesis of L-lysine. In this preferred aspect of this embodiment, the second nucleic acid encodes one of the following components of the L-lysine biosynthesis pathway: aspartokinase, aspartate beta-semialdehyde dehydrogenase, diaminopimelate dehydrogenase, diaminopimelate decarboxylase, dihydrodipicolinate synthetase, dihydrodipicolinate reductase, or pyruvate carboxylate.

The present invention is further directed to a polynucleotide comprising a first nucleic acid, the sequence of which comprises about 6 contiguous nucleotides, preferably about 10 contiguous nucleotides, even more preferably about 12, 15, 20, 30, 40, 50, 100, 150, 200, or in some cases up to about 500, 1000, or 1500 contiguous nucleotides, of a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or the complement of any of these sequences. By a first nucleic acid the sequence of which comprises about 10 contiguous nucleotides of any of said nucleic acid sequences, for example, is intended a nucleic acid which includes about 10 contiguous bases from any of said nucleotide sequences. Of course, the polynucleotide includes at least 10 contiguous nucleotides of any of said nucleic acid sequences, and may include about 12, 15, 20, 30, 40, 50, 100, 150, 200, or in some cases up to about 500, 1000, or 1500 contiguous nucleotides, or the entire sequence, of any of said nucleic acid sequences. In this context "about" includes the particularly recited size, larger or smaller by several (5, 4, 3, 2, or 1) nucleotides, at either terminus or at both termini.

Representative examples of polynucleotides of the invention include a first nucleic acid the sequence of which comprises, for example, a sequence from about nucleotide 1–50, 51–100, 101–150, 151–200, 201–250, 251–300, 301–350, 351–400, 401–450, or 450–500 of SEQ ID NO:4, SEQ ID NO:5, SEQ ID NO:6, SEQ ID NO:7, SEQ ID NO:8, SEQ ID NO:10, SEQ ID NO:11, SEQ ID NO:13, SEQ ID NO:14, SEQ ID NO:15, SEQ ID NO:16, SEQ ID NO:17, SEQ ID NO:19, SEQ ID NO:20, SEQ ID NO:21, or SEQ ID NO:22, or the complementary DNA strand thereto; a sequence from about nucleotide 1–50, 51–100, 101–150, 151–200, 201–250, 251–300, 301–350, 351–400, 401–450, 450–500, 501–550, 551–600, 601–650, 651–700, 701–750, 751–800, 801–850, 851–900, 901–950, 951–1000, 1001–1050, 1051–1100, 1101–1150, 1151–1200, 1201–1250, 1251–1300, 1301–1350, 1351–1400, 1401–1450, 1451–1500 or 1501–1583 of SEQ ID NO:9, or the complementary DNA strand thereto; a sequence from about nucleotide 1–50, 51–100, 101–150, 151–200, 201–250, 251–300, 301–350, 351–400, 401–450, 450–500, 501–550, 551–600, 601–650, 651–700, 701–750, 751–800, 801–850, 851–900, 901–950, 951–1000, or 1001–1083 of SEQ ID NO:12, or the complementary DNA strand thereto; or a sequence from about nucleotide 1–50, 51–100, 101–150, 151–200, 201–250, or 251–297 of SEQ ID NO:18, or the complementary DNA strand thereto. In this context "about" includes the particularly recited ranges, larger or smaller by several (5, 4, 3, 2, or 1) nucleotides, at either terminus or at both termini. Additional examples of polynucleotides of the invention include a first nucleic acid the sequence of which comprises a consensus –10 or –35 region as listed in Table 2, infra.

This embodiment of the present invention is directed to a polynucleotide comprising a first nucleic acid, the sequence of which comprises about 6 contiguous nucleotides, preferably about 10 contiguous nucleotides, even more preferably about 12, 15, 20, 30, 40, 50, 100, 150, 200, or in some cases up to about 500, 1000, or 1500 contiguous nucleotides, of a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or the complement of any of these sequences, irrespective of whether they have functional activity. This is because even where a particular polynucleotide does not have functional activity, one of skill in the art would still know how to use the nucleic acid molecule, for instance, as a hybridization probe, an S1 nuclease mapping probe, or a polymerase chain reaction (PCR) primer.

Preferred, however, a polynucleotide comprising a first nucleic acid, the sequence of which comprises about 6 contiguous nucleotides, preferably about 10 contiguous nucleotides, even more preferably about 12, 15, 20, 30, 40, 50, 100, 150, 200, or in some cases up to about 500, 1000, or 1500 contiguous nucleotides, of a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or the complement of any of these sequences, which do, in fact, have functional activity, in particular, polynucleotides which regulate transcription in *Corynebacterium* species. Examples of polynucleotides which regulate transcription in *Corynebacterium* species include promoters, operators, transcription factor recognitions sites, transcriptional complexes, and transcriptional regulatory elements, as described herein.

Preferably, polynucleotides of the present invention comprise a promoter which functions in *Corynebacterium* species, preferably in *Corynebacterium glutamicum*, *Brevibacterium flavum*, or *Brevibacterium lactofermentum*, even more preferably in *C. glutamicum*. Assays to determine whether a polynucleotide is capable of regulating transcription in *Corynebacterium* species can be routinely performed using techniques described herein and otherwise known in the art.

Accordingly, the present invention also encompasses the above polynucleotide, further comprising a second nucleic acid. Preferably, the second nucleic acid encodes one or more polypeptides, and the physical location of the first nucleic acid relative to the second nucleic acid is such that, under the appropriate conditions, the first nucleic acid will operably regulate transcription of the second nucleic acid, thereby facilitating production of the one or more polypeptides, as described herein.

One particularly preferred aspect of this embodiment is a polynucleotide comprising a first nucleic acid, the sequence of which comprises about 6 contiguous nucleotides, preferably about 10 contiguous nucleotides, even more preferably about 12, 15, 20, 30, 40, 50, 100, 150, 200, or in some cases up to about 500, 1000, or 1500 contiguous nucleotides, of a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22; and a second nucleic acid, which encodes a component of an amino acid biosynthesis pathway. A preferred amino acid biosynthesis pathway results in the synthesis of L-lysine. Examples of amino acid biosynthesis pathways, and specific components of the L-lysine biosynthesis pathway are described herein.

The nucleotide sequences of functional bacterial promoters exhibit a limited but significant degree of variability depending on the gene that is regulated by the particular promoters in question, and the bacterial species in which the promoter is found. See, e.g., Pátek et al., *Microbiology* 142:1297 (1996), which is incorporated herein by reference in its entirety. Despite this variability, investigators have identified promoter consensus sequences by comparing the nucleotide sequences of multiple bacterial promoters to one another. A consensus sequence is a sequence that reflects the most common nucleotides that are found in particular positions for a multitude of promoters. Frequently, the functionality of a promoter consensus sequence is confirmed by mutational analysis in an experimental system; i.e., the expression of a reporter gene that is under the control of a mutated promoter is assessed.

Early experiments and analyses of *E. coli* promoters identified a consensus sequence that comprises two nucleotide hexamers (six contiguous nucleotides) separated by about 17 nucleotides, and located about 35 and 10 nucleotides, respectively, upstream of the transcriptional start site for the corresponding gene. Pátek et al., *Microbiology* 142:1297 (1996). These two hexamers are known individually as the −35 and −10 regions, and their respective consensus sequences are TTGaca, and TAtaaT. Within a consensus sequence, capital letters denote particular nucleotides that are found in analogous positions in at least 70% of the promoter sequences analyzed. Lower case letters denote nucleotides that are found in analogous positions in between 42% to 70% of the promoter sequences analyzed.

Recently, Pátek et al. analyzed the sequences of 18 promoters from *C. glutamicum*, and four promoters from the temperate corynephage φGA1, to identify a promoter consensus sequence specific to *C. glutamicum*. From their analysis, Pátek et al. identified a −35 consensus sequence of ttGcca, and a −10 consensus sequence of TA.aaT. The period (".") at the third position of the −10 consensus sequence indicates that the nucleotide at this position does not establish a consensus among the *C. glutamicum* promoters that were compared by Pátek et al.

Accordingly, in one aspect of this embodiment of the present invention, a polynucleotide is provided which comprises a −10 promoter consensus sequence, and/or a −35 consensus sequence derived from a sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. While not being bound by theory, such sequence motifs may function as part of a promoter capable of regulating transcription in *Corynebacterium* species, preferably in *Corynebacterium glutamicum*, *Brevibacterium flavum*, or *Brevibacterium lactofermentum*, even more preferably in *C. glutamicum*.

To identify −10 promoter and/or −35 promoter consensus sequences, computer analyses of SEQ ID NOs: 1 through 22 were conducted using the prokaryotic nucleic acid motif search functionality provided by the OMIGA 2.0 computer software package. In addition, SEQ ID NOs: 1 through 22 were analyzed visually to identify any sequences that agree with the consensus sequences identified by Pátek et al. A summary of predicted −10 and −35 consensus sequences identified for SEQ ID NO:1 through 22 is listed in Table 2. It is to be noted that in the numbering convention of SEQ ID NOs 1 through 22, all nucleotides have a positive number and the numbers increase. This is in contrast to the normal convention for promoter regions, wherein the nucleotides are assigned negative numbers which increase up to nucleotide number 1 at the putative transcription start site.

TABLE 2

| SEQ ID NO: | -10 sequence(s) | Position | -35 sequence(s) | Position |
|---|---|---|---|---|
| 1 | | | TTGAGA* | 375 |
| 1 | | | TTGAAA* | 386 |
| 3 | | | TTGAAA* | 339 |
| 4 | TACAAT‡ | 275 | | |
| 4 | | | TTGAGA* | 57 |
| 4 | | | TTGAAA* | 186 |
| 4 | | | TTGAAA* | 301 |
| 4 | | | TTGCCA‡ | 466 |
| 5 | | | TTGAAA* | 307 |
| 5 | | | TTGAGA* | 340 |
| 7 | TACAAT‡ | 334 | | |
| 7 | | | TTGCCA‡ | 224 |
| 8 | | | TTGATA* | 341 |
| 8 | | | TTGCCA‡ | 371 |
| 9 | | | TTGATA* | 803 |
| 10 | TACAAT‡ | 406 | | |
| 10 | | | TTGACA* | 234 |
| 11 | | | TTGAAA* | 248 |
| 13 | TACAAT‡ | 394 | | |
| 13 | | | TTGCCA‡ | 118 |
| 14 | TAAAAT‡ | 169 | | |
| 15 | TAAAAT‡ | 379 | | |
| 17 | | | TTGACA* | 211 |
| 18 | | | TTGAAA* | 31 |
| 18 | | | TTGAAA* | 65 |
| 18 | TAAAAT‡ | 269 | | |
| 18 | | | TTGCCA‡ | 168 |
| 20 | | | TTGAAA* | 490 |
| 21 | | | TTGAAA* | 41 |
| 21 | | | TTGAGA* | 445 |
| 21 | | | TTGAAA* | 494 |

*consensus sequences identified by the OMIGA 2.0 program
‡consensus sequences identified visually by comparison to consensus sequences set forth in Pátek et al.

In another embodiment, the invention provides an isolated polynucleotide comprising a first nucleic acid at least 10 nucleotides in length, preferably at least 12, 15, 30, 50 or 150 nucleotides in length, which hybridizes under stringent conditions to a reference nucleic acid, or the complement thereof, wherein the sequence of said reference nucleic acid is selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a first nucleic acid "at least 10 nucleotides in length," which hybridizes to a reference nucleic acid is intended a first nucleic acid (either DNA or RNA) which hybridizes to 10 or more contiguous nucleotides from the nucleotide sequence of the reference nucleic acid (e.g., SEQ ID NOs 4–22).

This embodiment of the present invention is directed to an isolated polynucleotide comprising a first nucleic acid at least 10 nucleotides in length, preferably at least 12, 15, 30, 50 or 150 nucleotides in length, which hybridizes under stringent conditions to a reference nucleic acid, or the complement thereof, wherein the sequence of said reference nucleic acid is selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or the complement of any of these sequences, irrespective of whether they have functional activity. This is because even where a particular polynucleotide does not have functional activity, one of skill in the art would still know how to use the nucleic acid molecule, for instance, as a hybridization probe, an S1 nuclease mapping probe, or a polymerase chain reaction (PCR) primer.

Preferred, however, an isolated polynucleotide comprising a first nucleic acid at least 10 nucleotides in length, preferably at least 12, 15, 30, 50 or 150 nucleotides in length, which hybridizes under stringent conditions to a reference nucleic acid, or the complement thereof, wherein the sequence of said reference nucleic acid is selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22, or the complement of any of these sequences, which do, in fact, have functional activity, in particular, polynucleotides which regulate transcription in Corynebacterium species. Examples of polynucleotides which regulate transcription in Corynebacterium species include promoters, operators, transcription factor recognitions sites, transcriptional complexes, and transcriptional regulatory elements, as described herein. Preferably, polynucleotides of the present invention comprise a promoter which functions in Corynebacterium species, preferably in Corynebacterium glutamicum, Brevibac-

*terium flavum*, or *Brevibacterium lactofermentum*, even more preferably in *C. glutamicum*. Assays to determine whether a polynucleotide is capable of regulating transcription in *Corynebacterium* species can be routinely performed using techniques described herein and otherwise known in the art.

Accordingly, the present invention also encompasses the above polynucleotide, further comprising a second nucleic acid. Preferably, the second nucleic acid encodes one or more polypeptides, and the physical location of the first nucleic acid relative to the second nucleic acid is such that, under the appropriate conditions, the first nucleic acid will operably regulate transcription of the second nucleic acid, thereby facilitating production of the one or more polypeptides, as described herein.

One particularly preferred aspect of this embodiment is an isolated polynucleotide comprising a first nucleic acid at least 10 nucleotides in length, preferably at least 12, 15, 30, 50 or 150 nucleotides in length, which hybridizes under stringent conditions to a reference nucleic acid, or the complement thereof, wherein the sequence of said reference nucleic acid is selected from the group consisting of selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22; and a second nucleic acid, which encodes a component of an amino acid biosynthesis pathway. A preferred amino acid biosynthesis pathway results in the synthesis of L-lysine. Examples of amino acid biosynthesis pathways, and specific components of the L-lysine biosynthesis pathway are disclosed herein.

Another embodiment of the invention provides an isolated polynucleotide comprising a first nucleic acid, the sequence of which is at least 90%, 91%, 92%, 93%, 94%, 95%, 96%, 97%, 98%, or 99% identical to SEQ ID NO: 2, and a second nucleic acid which encodes a polypeptide which functions as a component of the lysine biosynthesis pathway. Alternatively in this embodiment, the sequence of the first nucleic acid comprises about 6 contiguous nucleotides, preferably about 10 contiguous nucleotides, even more preferably about 12, 15, 20, 30, 40, 50, 100, 150, 200, or 500, contiguous nucleotides, of SEQ ID NO:2, or the first nucleic acid is at least 10 nucleotides in length, preferably at least 12, 15, 30, 50 or 150 nucleotides in length, and hybridizes under stringent conditions to a reference nucleic acid, or the complement thereof, wherein the sequence of said reference nucleic acid is SEQ ID NO:2. A preferred amino acid biosynthesis pathway results in the synthesis of L-lysine. Examples of components of the L-lysine biosynthesis pathway are disclosed herein. In this embodiment, the first nucleic acid, which comprises the *C. glutamicum* aceA promoter, regulates transcription of the second nucleic acid.

Yet another embodiment of the invention provides an isolated polynucleotide comprising a first nucleic acid, the sequence of which is at least 90%, 91%, 92%, 93%, 94%, 95%, 96%, 97%, 98%, or 99% identical to SEQ ID NO: 3; and a second nucleic acid which encodes polypeptide which functions as a component of an amino acid biosynthesis pathway. Alternatively in this embodiment, the sequence of the first nucleic acid comprises about 6 contiguous nucleotides, preferably about 10 contiguous nucleotides, even more preferably about 12, 15, 20, 30, 40, 50, 100, 150, 200, or 500, contiguous nucleotides, of SEQ ID NO:3, or the first nucleic acid is at least 10 nucleotides in length, preferably at least 12, 15, 30, 50 or 150 nucleotides in length, and hybridizes under stringent conditions to a reference nucleic acid, or the complement thereof, wherein the sequence of said reference nucleic acid is SEQ ID NO:3. A preferred amino acid biosynthesis pathway results in the synthesis of L-lysine. Examples of amino acid biosynthesis pathways, and specific components of the L-lysine biosynthesis pathway are disclosed herein. In this embodiment, the first nucleic acid, which comprises the *C. glutamicum* aceB promoter, regulates transcription of the second nucleic acid.

A further embodiment of the invention provides an isolated *Corynebacterium* chromosome with a first nucleic acid integrated into the chromosome, the sequence of which is at least 90%, 91%, 92%, 93%, 94%, 95%, 96%, 97%, 98%, or 99% identical to SEQ ID NO:1. By "an isolated *Corynebacterium* species chromosome" is meant a bacterial chromosome which has been altered in some way to affect gene expression, either of naturally-occurring genes or heterologous genes, and then isolated from other non-altered chromosomes, e.g., by selection and isolation of a host cell harboring the chromosome. In this embodiment, the isolated *Corynebacterium* species chromosome also has a second nucleic acid integrated therein, wherein said second nucleic acid encodes polypeptide which functions as a component of an amino acid biosynthesis pathway. A preferred amino acid biosynthesis pathway results in the synthesis of L-lysine. Examples of amino acid biosynthesis pathways, and specific components of the L-lysine biosynthesis pathway are disclosed herein. In this embodiment, the first nucleic acid, which comprises the *C. glutamicum* pta promoter, regulates transcription of the second nucleic acid.

Another embodiment of the invention provides an isolated *Corynebacterium* chromosome with a first nucleic acid integrated into the chromosome, the sequence of which is at least 90%, 91%, 92%, 93%, 94%, 95%, 96%, 97%, 98%, or 99% identical to SEQ ID NO:23. In this embodiment, the isolated *Corynebacterium* species chromosome also has a second nucleic acid integrated therein, wherein said second nucleic acid encodes polypeptide which functions as a component of an amino acid biosynthesis pathway, preferably an L-lysine biosynthesis pathway. In this embodiment, the first nucleic acid, which comprises the *E. coli* araBAD promoter and the araC regulator molecule, regulates transcription of the second nucleic acid. The araC/araBAD transcriptional complex is a tightly regulated system responsive to the regulator molecule arabinose.

Yet another embodiment of the invention provides an isolated *Corynebacterium* chromosome with a first nucleic acid integrated into the chromosome, the sequence of which is identical to either SEQ ID NO:26 or SEQ ID NO:27. As with the embodiments described above, the isolated *Corynebacterium* species chromosome also has a second nucleic acid integrated therein, wherein said second nucleic acid encodes polypeptide which functions as a component of an amino acid biosynthesis pathway, preferably an L-lysine biosynthesis pathway, and the first nucleic acid, which is a trc or tac synthetic promoter, regulates transcription of the second nucleic acid. These synthetic promoters combine the −35 region from the trp promoter with the −10 region from the lacUV5 promoter. See Brosius, J. et al., *J. Biol. Chem.* 260, 3539 (1985). In the embodiment, the isolated chromosome further has a third nucleic acid integrated therein, the sequence of which is at least 90%, 91%, 92%, 93%, 94%, 95%, 96%, 97%, 98%, or 99% identical to SEQ ID NO:28. This third nucleic acid is operably linked to a transcription control region, and the nucleic acid encodes a polypeptide at least 90%, 91%, 92%, 93%, 94%, 95%, 96%, 97%, 98%, or 99% identical to SEQ ID NO:29, the *E. coli* lac repressor gene. The lacI$^q$-trc (SEQ ID NO:30) or the lacI$^q$-tac transcriptional complex is responsive to the regulatory molecules isoproplythiogalactoside (IPTG) and lactose. This regulatory complex in *Corynebacterium glutamicum*, however, is leaky, i.e., transcription occurs in the absence of any added inducer.

In each of the isolated chromosomes described above, the second nucleic acid may be a naturally occurring *Corynebacterium* nucleic acid, situated in its normal position on the chromosome, it may be a naturally occurring *Corynebacterium* nucleic acid which has been moved to a different position on the chromosome, or it may be a non-native nucleic acid. The first nucleic acid is engineered to be in a physical location which allows it to regulate transcription of the second nucleic acid either through in vitro cloning of a vector having both the first and second nucleic acids followed by homologous or random recombination into the *Corynebacterium* species chromosome, or it is inserted in front of a selected second nucleic acid already situated in the chromosome through homologous recombination. Such manipulations are readily understood by those of ordinary skill in the art.

In another aspect of the above embodiments, a *Corynebacterium* species host cell comprising a *Corynebacterium* species chromosome as described above is provided, preferably a host cell derived from *Corynebacterium glutamicum*, *Brevibacterium flavum*, and *Brevibacterium lactofermentum*, and even more preferably derived from *Corynebacterium glutamicum*. In a related aspect, a method of producing such a *Corynebacterium* species host cell is provided, which comprises transforming *Corynebacterium* species cells with a vector comprising a first nucleic acid as described above, wherein said vector facilitates integration of the first nucleic acid into the chromosome of said *Corynebacterium* species cells, and selecting the host cell in certain preferred embodiments, the vector also comprises the second nucleic acid described above, and/or the third nucleic acid described above, with the first nucleic acid being physically situated to regulate transcription of the second nucleic acid. These vectors are also provided.

The present invention further relates to variants of the polynucleotides of the present invention. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. Particularly preferred are variants which alter the level of activity of the polynucleotide relative to a non-variant polynucleotide. For example, variants which increase or decrease the strength of a promoter, or variants which alter or eliminate the need for an inducer. Methods to construct variant promoters and screen them for their relative strengths utilizing reporter genes are well known in the art. See, e.g., Vašicová, et al., *J. Bacteriol.* 181:6188–6199 (1999), which is incorporated herein by reference in its entirety.

D. Vectors and Host Cells

The present invention also relates to vectors which include polynucleotides of the present invention, host cells which are engineered with vectors of the invention and methods to increase the production of metabolic products such as amino acids purines, pyrimidines, and heterologous polypeptides through utilization of host cells of the invention.

Host cells can be engineered to incorporate polynucleotides of the present invention. The polynucleotides may be introduced alone or with other polynucleotides. Such other polynucleotides may be introduced independently, co-introduced or introduced joined to the polynucleotides of the invention.

In accordance with this aspect of the invention the vector may be, for example, a plasmid vector or a bacteriophage vector. Such vectors may be introduced into *Corynebacterium* cells such that they are maintained and replication as an extrachromosomal element, or, alternatively, such that they integrate into the chromosome. Vectors are introduced into host cells by well known techniques for introducing DNA and RNA into prokaryotic cells, examples of which are described in the Examples, infra.

Preferred vectors comprise a first nucleic acid which is capable of regulating transcription of a second nucleic acid which is inserted in operable association, preferably immediately downstream, of the first nucleic acid. The second nucleic acid preferably encodes a polypeptide such as an enzyme in an amino acid biosynthesis pathway. Especially preferred among vectors are those which allow convenient insertion of the second nucleic acid into the vector into the proper position to be regulated by the first nucleic acid, for example, through the use of a multiple cloning region. Appropriate trans-acting factors such as inducers either are supplied by the host cell, supplied by a complementing vector or supplied by the vector itself upon introduction into the host cell.

A great variety of vectors can be used in the invention. Such vectors include chromosomal, episomal and virus-derived vectors e.g., vectors derived from bacterial plasmids and from bacteriophage, as well as vectors derived from combinations thereof, such as those derived from plasmid and bacteriophage genetic elements, such as cosmids and phagemids, all may be used in accordance with this aspect of the present invention. Generally, any vector suitable to maintain and propagate a polynucleotide in a bacterial host may be used in this regard.

A large numbers of suitable vectors for use in bacteria are known, many of which are commercially available. Preferred prokaryotic vectors include plasmids such as those capable of replication in *E. coli* (such as, for example, pBR322, ColEl, pSC101, pACYC 184, πVX. Such plasmids are, for example, disclosed by Maniatis, T., et al., In: *Molecular Cloning*, A Laboratory Manual, Cold Spring Harbor Press, Cold Spring Harbor, N.Y. (1982)). The following vectors are provided by way of example: pET (Novagen), pQE70, pQE60, pQE-9 (Qiagen), pBs, phagescript, psiX174, pBlueScript SK, pBsKS, pNH8a, pNH16a, pNH18a, pNH46a (Stratagene); pTrc99A, pKK223-3, pKK233-3, pDR540, pRIT5 (Pharmacia).

Preferred vectors for the isolated polynucleotides of the invention include the pFC1 to pFC7 novel family of combinatorial cloning vectors (Lonsdale, D. M., et al., *Plant Molecular Biology Reporter* 13: 343–345 (1995)), the pK184 vector (Jobling, M. G. and Homes, R. K., *Nucleic Acid Research* 18: 5315–5316 (1990)).

Another group of preferred vectors are those that are capable of autonomous replication in *Corynebacterium* species. Such vectors are well known to those skilled in the art of amino acid production by way of microbial fermentation, examples of which include pSR1, pMF1014α and vectors derived therefrom.

The second nucleic acid encoding a polypeptide is operatively associated with the first nucleic acid as described above, which provides the appropriate transcription control sequence(s)), in particular, a promoter. In addition, the vector may contain sites for transcription initiation and termination, and, in the transcribed region, a ribosome binding site for translation. The second nucleic acid, which provides the coding region of the polypeptide to be regulated will include a translation initiating AUG or GUG at the beginning and a termination codon (UAA, UGA or UAG) appropriately positioned at the end of the coding region.

In addition, and as described in more detail herein, the vector may contain control regions that regulate as well as engender expression. Generally, such regions will operate by controlling transcription, such as inducer or repressor binding sites and enhancers, among others.

Vectors of the present invention generally will include a selectable marker. Such markers also may be suitable for amplification or the vectors may contain additional markers for this purpose. In this regard, vectors preferably contain one or more selectable marker genes to provide a phenotypic trait for selection of transformed host cells. Such markers include, but are not limited to, an antibiotic resistance gene such as a chloramphenicol, ampicillin, or kanamycin resistance gene, or an autotrophic gene which allows the host cell to grow in the absence of a nutrient for which the host cell strain is normally autotrophic.

If the vector is intended to be maintained in the host cell extrachromosomally, it will contain, in addition and origin of replication which will allow it to replicate in the *Corynebacterium* species host cell. Alternatively, if it is desired that the vector integrate into the *Corynebacterium* species chromosome, the vector is constructed such that it cannot replicate in *Corynebacterium*. For example, such a vector might be capable of propagation in another organism, for example, *E. coli*, but lack the proper origin of replication to be propagated in *Corynebacterium*. In another aspect of this embodiment, the vector is a shuttle vector which can replicate and be maintained in more than one host cell species, for example, such a shuttle vector might be capable of replication in a *Corynebacterium* host cell such as a *C. glutamicum* host cell, and also in an *E. coli* host cell.

A vector comprising a polynucleotide as described elsewhere herein may be introduced into an appropriate *Corynebacterium* species host cell using a variety of well known techniques, for example, transformation or electroporation. Appropriate culture mediums and conditions for culturing *Corynebacterium* host cells are known in the art.

The invention provides methods for increasing amino acid production and processes for the production of an amino acid wherein increased biosynthetic pathway gene expression is accomplished through insertion of an isolated polynucleotide into the chromosome of a host cell. For example, insertion of isolated polynucleotides into the chromosome of *Corynebacterium* species may be done utilizing the pKl84 plasmid described by Jobling, M. et al., *Nucleic Acids Research* 18(17): 5315–5316 (1990). Because these vectors lack a *Corynebacterium* species origin of replication and contains a selectable marker such as kanamycin (kan), cells will only be capable of growing under selection if the vector has been inserted into the host cell chromosome by homologous recombination.

The invention also provides methods for increasing amino acid production and processes for the production of an amino acid wherein increased biosynthetic pathway gene expression is accomplished through the introduction into a host cell of a self-replicating, extra-chromosomal vector, e.g., a plasmid, comprising an isolated nucleic acid molecule encoding an amino acid biosynthetic pathway gene or genes. Suitable plasmids for these embodiments include pSR1 and other derivatives ofpSR1 (Archer, J. et al., *J. Gen. Microbiol.* 139: 1753–1759 (1993)).

These vectors are listed solely by way of illustration of the many vectors available to those of skill in the art. Other vectors are described in the Examples, infra. Selection of appropriate vectors to transform into a host cell is a well known procedure and the requisite techniques for vector construction, introduction of the vector into the host and maintenance in the host are routine skills in the art.

The present invention also relates to *Corynebacterium* species host cells comprising the above-described vector constructs described herein. The host cell can be any *Corynebacterium* species, preferably *Corynebacterium glutamicum, Brevibacterium flavum*, or *Brevibacterium lactofermentum*, even more preferably a strain of *C. glutamicum*. Preferred strains of *C. glutamicum* to use as host cells of the invention include: NRRL-B11474, ATCC 21799, ATCC 21529, ATCC 21543, and E12.

Introduction of a vector into the host cell can be effected by transformation, electroporation, transduction, infection or other methods. Such methods are described in many standard laboratory manuals, such as Davis et al., *Basic Methods in Molecular Biology* (1986).

E. Methods and Processes of the Invention

Various embodiments of the invention provide methods to increase the production of an amino acid and processes for the production of an amino acid from a *Corynebacterium* species host cell. Particularly preferred *Corynebacterium* species of the methods and processes of the invention include: *Corynebacterium glutamicum, Brevibacterium flavum, Brevibacterium lactofermentum* and other *Cornynebacteria* and *Brevibacteria* species known in the art.

Amino acid biosynthetic pathway genes embodied by the methods and processes described herein include those for L-glycine, L-alanine, L-methionine, L-phenylalanine, L-tryptophan, L-proline, L-serine, L-threonine, L-cysteine, L-tyrosine, L-asparagine, L-glutamine, L-aspartic acid, L-glutamic acid, L-lysine, L-arginine, L-histidine, L-isoleucine, L-leucine, and L-valine biosynthesis. Particularly preferred embodiments are drawn to biosynthetic pathway genes for L-lysine (Sahm et al., *Ann. N. Y Acad. Sci.* 782: 25–39 (1996)), L-threonine, L-isoleucine, L-tryptophan, and L-valine.

By way of example, the amino acid pathway for L-lysine biosynthesis is well known to skilled artisans of amino acid production in *Corynebacterium* species. Genes encoding the enzymes important for the conversion of L-aspartate to L-lysine include the ask, asd, dapA, dapB, ddh, and lysA genes, which encode, respectively, aspartokinase, aspartate beta-semialdehyde dehydrogenase, dihydrodipicolinate synthetase, dihydrodipicolinate reductase, diaminopimelate dehydrogenase, diaminopimelate decarboxylase, and pyruvate carboxylase. Thus, the invention provides herein for exemplary purposes only, specific embodiments utilizing L-lysine biosynthetic pathway genes. Other embodiments drawn to the use of biosynthetic pathway genes for the synthesis of other amino acids are also encompassed by the invention described herein.

The methods to increase the production of a biosynthetic product such as an amino acid and the processes for the production of the biosynthetic product of the invention involve increasing the expression of at least one biosynthetic pathway gene. Preferred methods of increasing expression comprise using promoters of the invention.

Accordingly, the present invention provides a first nucleic acid which preferably comprises a promoter. Preferred promoters include, but are not limited to the following types of promoters: a constitutive promoter, an inducible promoter, a derepressable promoter, a heat sensitive promoter, and a cold sensitive promoter. In this aspect of the invention, a constitutive promoter causes the second nucleic acid to be transcribed at a substantially constant rate; an inducible promoter will be non-functional or will function at a reduced level under certain standard culture conditions, but causes elevated transcription of the second nucleic acid when the transformed host cells are grown in the presence of an appropriate inducer substance; a derepressable promoter causes elevated transcription of the second nucleic acid when the transformed host cells are grown in the absence of an appropriate suppressor substance, but will be non-functional or will function at a reduced level when the suppressor substance is present; a heat sensitive promoter causes elevated transcription of the second nucleic acid when the transformed host cells are grown in medium the temperature of which is adjusted to a temperature that is greater than the optimum temperature for wild-type untransformed host cells; and a cold sensitive promoter causes elevated transcription of the second nucleic acid when said transformed host cells are grown in a medium the temperature of which is adjusted to a temperature that is less than the optimum temperature for a wild-type untransformed host cell.

Also included within this embodiment of the invention are methods wherein the transformed host cells are grown to a sufficient cell density according to methods well known in the art. Further included in this embodiment are methods for substantially purifying the biosynthetic product from said culture, wherein said purification methods are also well known in the art.

In certain embodiments of the present invention, an inducible promoter is used. When an inducible promoter is used, it is preferred that the transformed *Corynebacterium* species host cells are first allowed to proliferate to a sufficient cell density in the absence of the inducer, followed by addition of the inducer to the culture medium thereby stimulating production of said product. Examples of inducers include, but are not limited to one or more of the following substances: acetic acid, pyruvate, ethanol, fatty acids, cellulose subunits, starch subunits, triglycerides, or any of the following sugars: fructose, maltose, lactose, or arabinose.

In other embodiments, a derepressable promoter is used. When a derepressable promoter is used, it is preferred that the transformed *Corynebacterium* species host cells are first allowed to proliferate to a sufficient cell density in the presence of the suppressor, followed by either removal of the suppressor from the culture, or replacement of the medium containing the suppressor with medium lacking the suppressor, thereby stimulating production of said product. Under certain conditions, the suppressor is removed from the medium by being metabolized by the host cell. Examples of said suppressors include, but are not limited to any of the following substances: a purine, a pyrimidine, oxygen, or a suppressor amino acid including histidine.

In other embodiments, the promoter is self-inducing, i.e., the inducer molecule is produced by the host cell and builds up through the course of the growth, thereby changing gene expression as growth progresses. In this embodiment, the promoter is induced either gradually or at some point in the growth of the host cell culture, however this induction does not require the addition of exogenous compounds to the culture medium.

In yet another embodiment, a heat sensitive promoter is used. When a heat sensitive promoter is used, it is preferred that the transformed host cells are first allowed to proliferate to a sufficient cell density in culture medium, the temperature of which is adjusted to the optimum growth temperature for untransformed host cells, followed by adjusting the temperature of said culture medium to a temperature that is greater than the optimum growth temperature for untransformed host cells.

In yet another embodiment, a cold sensitive promoter is used. When a cold sensitive promoter is used, it is preferred that the transformed host cells are first allowed to proliferate to a sufficient cell density in culture medium, the temperature of which is adjusted to the optimum growth temperature for untransformed host cells, followed by adjusting the temperature of said culture medium to a temperature that is less than the optimum growth temperature for untransformed host cells.

In a related embodiment of the invention, a method is provided for the production of a product such as an amino acid, a purine nucleotide, or a heterologous polypeptide in a *Corynebacterium* species host cell utilizing a heterologous transcriptional complex. According to this embodiment, the host cell harbors the heterologous transcriptional complex integrated into the bacterial chromosome. Preferred heterologous transcriptional complexes include the *E. coli* araC-araBAD transcriptional complex (SEQ ID NO:23), and the lacI$^q$-trc or lacI$^q$-tac transcriptional complexes which combine the *E. coli* lacI$^q$ repressor gene (lacI$^q$, SEQ ID NO:28) with either the trc promoter (SEQ ID NO:26 or SEQ ID NO:30) or the tac promoter (SEQ ID NO:27). These synthetic promoters combine the −35 region from the trp promoter with the −10 region from the lacUV5 promoter. See Brosius, J. et al., *J. Biol. Chem.* 260, 3539 (1985).

The method utilizing the *E. coli* araC-araBAD transcriptional complex preferably further comprises culturing the host cell in or on a medium to which the inducer arabinose has been added, either throughout growth of the host cells, or at a point during growth where the host cell culture has reached an optimal density. The method utilizing either the lacI$^q$-trc or the lacI$^q$-tac transcriptional complex may further comprise culturing the host cell in or on a medium to which the inducer isoproplythiogalactoside (IPTG) or the inducer lactose has been added, either throughout growth of the host cells, or at a point during growth where the host cell culture has reached an optimal density. However, in *C. glutamicum*, the lacI$^q$/trc system is leaky, therefore an inducer is not required for optimal growth.

A preferred aspect of this embodiment provides a method for the production of an amino acid in a Corynebacterium host cell utilizing a heterologous transcriptional complex integrated into the host cell chromosome, where the heterologous transcriptional complex operably regulates production a polypeptide which functions in an amino acid biosynthesis pathway. In this aspect, the heterologous transcriptional complex, when integrated into the host cell chromosome, regulates transcription of one or more metabolic pathway enzymes, thereby resulting in elevated production of the amino acid by the transformed host cell.

One aspect of this embodiment involves addition of an inducer to the culture medium thereby upregulating the heterologous transcriptional complex. In the method utilizing the *E. coli* araC-araBAD transcriptional complex arabinose is added to the medium. In the method utilizing the lacI$^q$-trc or the lacI$^q$-tac transcriptional complex, IPTG and/or lactose is added to the culture medium. Preferably in this method, the host cells are grown to a sufficient cell density according to methods well known in the art prior to addition of the inducer molecule.

For those embodiments of the invention drawn to a method to increase production of an amino acid, screening for increased production of an amino acid, for example L-lysine, may be determined by directly comparing the amount of L-lysine produced in culture by a standard *Corynebacterium* species strain to that of a *Corynebacterium* species host cell which has been transformed to comprise an isolated polynucleotide of the present invention. The level of production of the amino acid of choice may conveniently determined by the following formula to calculate the percent yield from dextrose: [(g amino acid/L/(g dextrose consumed/L)]*100.

A variety of media known to those skilled in the art may be used to support cell growth for the production of an amino acid. Illustrative examples of suitable carbon sources include, but are not limited to: carbohydrates, such as glucose, fructose, sucrose, starch hydrolysate, cellulose hydrolysate and molasses; organic acids, such as acetic acid, propionic acid, formic acid, malic acid, citric acid, and fumaric acid; and alcohols, such as glycerol. Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing sources, including meat extract, peptone, corn steep liquor, casein hydrolysate, soybean cake hydrolysate, urea and yeast extract.

A variety of fermentation techniques are known in the art which may be employed in processes of the invention drawn to the production of amino acids. Generally, amino acids may be commercially produced from the invention in fermentation processes such as the batch type or of the fed-batch type. In batch type fermentations, all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time.

In a batch fermentation an organism grows until one of the essential nutrients in the medium becomes exhausted, or until fermentation conditions become unfavorable (e.g. the pH decreases to a value inhibitory for microbial growth). In fed-batch fermentations measures are normally taken to maintain favorable growth conditions, e.g. by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous.

The amino acid may be recovered by any method known in the art. Exemplary procedures are provided in the following: Van Walsem, H. J. & Thompson, M. C., *J. Biotechnol.* 59:127–132 (1997), and U.S. Pat. No.3,565,951, both of which are incorporated herein by reference.

EXAMPLES

Example 1

Production of Host Cells Utilizing Transcriptional Regulatory Regions of the Present Invention

*Corynebacterium* species host cells, in which to express metabolic polypeptides are constructed as follows. Polynucleotides of the present invention which comprise transcriptional regulatory regions related to SEQ ID NOs 1–23, 26–28, and 30 are inserted upstream of a multiple cloning region, thereby allowing convenient insertion coding regions to be regulated and expressed. Testing of the various transcriptional regulatory regions is conveniently carried by inserting the various regulatory regions in operable association to a known reporter gene, such as β-galactosidase (lacZ). Methods and techniques common to the art of recombinant DNA technology are used in making vectors of the invention, as may be found in the many laboratory manuals cited and incorporated herein, for example as found in J. Sambrook, E. F. Fritsch and T. Maniatis, *Molecular Cloning: A Laboratory Manual,* 2d ed., Cold Spring Harbor Laboratory Press, Cold Spring Harbor, N.Y. (1989). Construction of exemplary vectors is set forth in Example 2, infra.

For cell transformation experiments with the isolated nucleic acid molecules of the invention, the growth and preparation of competent cells may be done according to the following procedure: (1) picking a fresh, single colony of *Corynebacterium glutamicum* and growing a culture overnight in 10 mL CM (SM1) in a 250 mL shake flask at 30 degrees Celsius with agitation; (2) inoculating 200 mL of "Growth Media" with the overnight culture to an optical density (O.D.) of 660 nm of 0.1 in a 500 mL shake flask; (3) growing the culture at 30 degrees Celsius with agitation for 5–6 hours; (4) pouring the culture into a chilled, sealed, sterile 250 mL centrifuge bottle; Spin at 8–10 K for ten minutes in Refrigerated Sorvall at 4 degrees Celsius; (5) pouring off the supernatant thoroughly and resuspending the cell pellet in an equal volume of ice-cold, sterile, deionized water; (6) centrifuging the sample again under the same conditions; (7) repeating the water wash remembering to keep everything ice-cold; (8) pouring off the supernatant thoroughly and resuspending the cell pellet in 1 mL of ice-cold, sterile 10% glycerol and transferring the cells to a chilled, sterile, 1.5 mL microcentrifuge tube; (9) spin the sample for 10 minutes in a refrigerated centrifuge; (10)

pipetting off and discarding the supernatant, and resuspending the pellet in two to three times the pellet volume (200–400 μL) of 10% glycerol; and (11) aliquoting, if necessary, the cells into chilled tubes and freezing at −70 Celsius.

Plasmid DNAs are introduced into *Corynebacterium glutamicum* host cells by the following electroporation procedure: (1) pipetting 35 μL cell/glycerol solution onto the side wall of a chilled 0.1 cm electrocuvette; (2) pipetting about 2–4 μL of plasmid into the solution and mixing the sample by gentle pipetting up and down; (3) bringing the entire solution to the bottom of the electrocuvette by gentle tapping, avoiding the creation of bubbles; (4) keeping the sample on ice until ready for the electroshock step, wiping off any moisture on the outside of the electrocuvette prior to the electroshock administration, and shocking the cells one time at 1.5 kV, 200Ω, 25 μF.

Cells are allowed to recover from electroporation by: (1) immediately pipetting 1 mL of warm "Recovery Media" into the electrocuvette and thoroughly mixing the solution by pipetting; (2) incubating the solution (in the electrocuvette) at 30 degrees Celsius for at least three hours for antibiotic resistance expression and cell recovery and (3) plating on selection media and incubating at 30 degrees Celsius for 3 days.

Example 2

Preparation of L-Lysine Pathway Constructs Utilizing the Regulatory Regions of the Present Invention Isolated nucleic acid molecules encoding L-lysine amino acid biosynthesis pathway genes are isolated by methods known to those of ordinary skill in the art.

Constructs which facilitate expression and regulation of L-lysine amino acid biosynthesis pathway genes are introduced into *Corynebacterium* strains by methods such as those described in Example 1. Any strain of *Corynebacterium*, particularly that of *Corynebacterium glutamicum*, may be utilized for the isolation of nucleic acid molecules for use in the preparation of vectors to improve amino acid biosynthetic pathway gene expression. Particularly preferred strains include: NRRL-B11474, ATCC 21799, ATCC 21529, ATCC 21543, and E12. As one skilled in the art would know, the invention is not limited to these specific strain origins.

Methods and techniques common to the art of recombinant DNA technology are used in making vectors of the invention, as may be found in the many laboratory manuals cited and incorporated herein.

The polymerase chain reaction (PCR) technique may be used in the making of vectors of the invention. In a typical reaction, the standard 10× stock solution (100 mM Tris-HCL, pH 8.3, 500 mM KCL, 1.5 mM MgCl$_2$) is diluted to 1× for use. Typical reaction conditions were used for PCR amplication: 10 mM Tris, pH 8.3, 50 mM KCl, 1.5 mM MgC12, 0.01% gelatin, 200 uM deoxynucleotides, 0.2–1.0 uM primers and 2.0 U/100 ul pfu polymerase. Standard cycling parameters were also employed in PCR reactions: For 30 cycles, template denaturation was performed at 94° C. for 30 sec.; 65° C. annealing temperature was performed for 1 min (or annealing temperature appropriate for particular primer pair); product extension was performed at 72° C. for 1 min (if product is <500 bp), 3 min (if product is >500 bp); and at the end of cycling, a final extension at 72° C. for 7 min was performed.

(a) Construction of pTrcLacZ

A plasmid construct designed to replicate as a plasmid in *Corynebacterium*, which contains the β-galactosidase (lacZ) coding region operably associated with the lacI$^q$/trc regulatory region, was constructed as follows. Plasmid pZap2, a plasmid which is capable of replicating in *Corynebacterium*, was digested with XbaI and SmaI, which linearize the plasmid just upstream of the lacZ gene. A cassette containing lacI$^q$ and the trc promoter was excised from plasmid pTrc99A, available from Amersham Pharmacia Biotech, by digestion with SphI, filling in the overhang, and then digesting with XbaI. The 1517-bp cassette (SEQ ID NO:30) was isolated from an agarose gel, and ligated into the linearized pZap2 plasmid. The resulting ligation mix was used to transform *Escherichia coli*, and colonies were isolated from LB plates supplemented with ampicillin (100 μg/ml), Xgal, and IPTG (LBXIA medium). Blue colonies were selected and plasmid isolates were verified by restriction digestion and electrophoresis.

(b) Construction of pAraBADLacZ

A plasmid construct designed to replicate as a plasmid in *Corynebacterium*, which contains the lacZ coding region operably associated with the araC/araBAD regulatory region, was constructed as follows. Plasmid pZap2 was digested with XbaI and SmaI as in (a). A cassette containing the araC gene and the pBAD promoter was excised from plasmid pBAD18-Cm, available from the American Type Culture Collection, Catalog No. 87396, by digestion with ClaI followed by a fill-in reaction and then digestion with XbaI. The cassette (i.e., nucleotides 1 to 1338 of SEQ ID NO:23) was isolated from an agarose gel and was ligated into the linearized pZap2 plasmid. Transformed *E. coli* colonies were plated on LBXIA medium as in (a), blue colonies were selected, and plasmid isolates were verified by restriction digestion and electrophoresis.

(c) Construction of pAceB10Zap2

A plasmid construct designed to replicate as a plasmid in *Corynebacterium*, which contains the lacZ coding region operably associated with the *C. glutamicum* aceB regulatory region, was constructed as follows. A cassette containing the aceB promoter was PCR amplified from plasmid pSLD5 using forward primer 5' GTGCGGATCCTGGCTTTC-CAACGTTT 3' (SEQ ID NO:31, BamHI site underlined) and reverse primer 5' CATGGGCTCGAGATGACCTGT-GCCTA 3' (SEQ ID NO:32, SacI site underlined). The resulting PCR product was digested with BamHI and SacI and ligated into the polylinker region of cloning vector pD11 to produce pD11aceB. The resulting plasmid was screened for orientation, and then the aceB promoter cassette was released from the vector by digestion with KpnI and XbaI and cloned into the KpnI and XbaI sites of plasmid pZap2 as described in (a). Transformed *E. coli* colonies were plated on LBXIA medium as in (a), blue colonies were selected, and plasmid isolates were verified by restriction digestion and electrophoresis.

(d) Construction of 131aceB/ask

A plasmid construct designed to integrate into the *C. glutamicum* chromosome, which contains the *C. glutamicum* aspartokinase (ask) coding region operably associated with the *C. glutamicum* aceB regulatory region, was constructed as follows. Plasmid pBGS13 1 (described in Spratt, B. G. et al. *Gene* 41:337–342 (1986)) was digested with SmaI. The aceB cassette was released from plasmid pD11aceB, produced as in (c), by digestion with appropriate restriction enzymes and the cassette was subjected to a fill-in reaction to produce blunt ends. The cassette was then ligated into the digested pBGS131. Plasmid isolates were tested for the proper orientation of the aceB promoter by restriction digestion and electrophoresis, resulting in plasmid 131 aceB. The *C. glutamicum* ask coding region was released from pTrc99Aask (produced as in (f), infra) by digestion with SacI and KpnI and cloned into the SacI and KpnI sites of 131aceB, to produce 131aceBask.

(e) Construction of PD10aceBask

A plasmid construct designed to replicate as a plasmid in *C. glutamicum*, which contains the *C. glutamicum* aspartokinase (ask) coding region operably associated with the *C. glutamicum* aceB regulatory region, was constructed as follows. A cassette containing the ask coding region operably associated with the aceB regulatory region was released from 131aceBask, produced as in (d), by digestion with BamHI and KpnI. The resulting fragment was cloned into the BamHI and KpnI sites of plasmid pD10, which is capable of replicating in *C. glutamicum*, to produce pD10aceBask.

(f) Construction of 131 LacI$^q$/trc-ask

A plasmid construct designed to integrate into the *C. glutamicum* chromosome, which contains the *C. glutamicum* aspartokinase (ask) coding region operably associated with the lacI$^q$/trc regulatory region, was constructed as follows. The PCR-amplified ask coding region was digested with SacI and KpnI, and ligated into plasmid pTrc99A which had been digested with SacI and KpnI to produce pTrc99Aask. A cassette containing the ask coding region operably associated with the lacI$^q$/trc regulatory region was then released from pTrc99Aask by digestion with SphI, and was cloned into the SphI site of plasmid pBGS131 to produce 131LacI$^q$/trc-ask.

(g) Construction of Additional LacZ Plasmid Expression Constructs

Plasmid constructs designed to replicate as a plasmid in *Corynebacterium*, which contain the lacZ coding region operably associated with *C. glutamicum* regulatory regions contained in SEQ ID NOs 1, 2, and 4–22, are constructed as follows. Cassettes containing the regulatory regions present in SEQ ID NOs 1, 2, and 4–22 are PCR amplified from the *C. glutamicum* chromosome using primers engineered to introduce appropriate restriction enzyme recognition sites onto the ends of the cassettes. In designing the primers, care is taken to introduce sites for restriction enzymes which will not digest the cassette internally. The resulting PCR products are digested with the chosen restriction enzymes, and the fragments are ligated into a polylinker region of a standard cloning vector. The resulting plasmids are screened for orientation, and then the cassettes are released from the vector by digestion with appropriate restriction enzymes, filled in as necessary, and cloned into the polylinker region upstream of the lacZ gene in plasmid pZap2 as described in (a). Transformed *E. coli* colonies are plated on LBXIA medium as in (a), blue colonies are selected, and plasmid isolates are verified by restriction digestion and electrophoresis.

(h) Construction Additional Aspartokinase Expression Constructs Designed to Integrate Plasmid constructs designed to integrate into the *C. glutamicum* chromosome, which contain the *C. glutamicum* aspartokinase (ask) coding region operably associated with *C. glutamicum* regulatory regions contained in SEQ ID NOs 1, 2, and 4–22, are constructed as follows. Plasmid pBGS131 is digested with SmaI, or other appropriate restriction enzyme. The regulatory cassettes prepared as in (g) are released by digestion with appropriate restriction enzymes and the cassettes are subjected to fill-in reactions to produce blunt ends as needed. The cassettes are then ligated into the digested pBGS131. Plasmid isolates are tested for the proper orientation of the regulatory regions by restriction digestion and electrophoresis, to produce plasmids 131SEQ ID NO:1, 131 SEQ ID NO:2, and 131SEQ ID NO:4–131SEQ ID NO:22. The *C. glutamicum* ask coding region is released from pTrc99Aask (produced as in (f)) by digestion with SacI and KpnI (or other appropriate restriction enzymes), or is PCR amplified from a *C. glutamicum* chromosome, and is cloned into the corresponding sites of plasmids 131SEQ ID NO:1, 131 SEQ ID NO:2, and 131SEQ ID NO:4–131 SEQ ID NO:22, to produce the plasmids 131SEQ ID NO:1-ask, 131 SEQ ID NO:2-ask, and 131SEQ ID NO:4-ask through 131 SEQ ID NO:22-ask.

(i) Construction of Additional Aspartokinase Constructs Designed to Replicate as a Plasmid Plasmid constructs designed to replicate as a plasmid in *C. glutamicum*, which contain the *C. glutamicum* aspartokinase (ask) coding region operably associated with *C. glutamicum* regulatory regions contained in SEQ ID NO1,2, and 4–22, are constructed as follows. Cassettes containing the ask coding region operably associated with the regulatory regions contained in SEQ ID NO:1, SEQ ID NO:2, and SEQ ID NO:4-SEQ ID NO:22 are released from plasmids 131SEQ ID NO:1-ask, 131 SEQ ID NO:2-ask, and 131SEQ ID NO:4-ask through 131 SEQ ID NO:22-ask, produced as in (h), by digestion with appropriate restriction enzymes. The resulting fragments are cloned into corresponding sites of plasmid pD10, which is capable of replicating in *C. glutamicum*, to produce plasmids PD10/SEQ ID NO:1-ask, PD10/SEQ ID NO:2-ask, and PD10/SEQ ID NO:4-ask through PD10/SEQ ID NO:22-ask.

Example 3

Use of LacZ as a Reporter to Demonstrate Transcriptional Regulation by araBAD (SEQ ID NO:23) and the lacI$^q$/trc Transcriptional Complex (SEQ ID NO:30) in *Corynebacterium* (41-004002)

The ability of the heterologous transcriptional regulatory regions lacI$^q$/trc and araBAD (with the araC repressor) to control gene expression in *C. glutamicum* was tested by measuring expression of β-galactosidase. Plasmids pTrcLacZ and pAraBADLacZ, produced as in Examples 2(a) and 2(b), respectively, were transferred into *C. glutamicum* according to the methods described in Example 1. The lacZ reporter gene, regulated by either of the two regulatory regions, was expressed from a plasmid replicating in *C. glutamicum*, grown in the presence of an inducer, IPTG in the case of the lacI$^q$/trc regulatory region, or arabinose in the case of the araC/araBAD regulatory region. The level of β-galactosidase production was measured, and the results are shown in Table 3.

TABLE 3

| regulator/promoter | Inducer | nmol/min/mg | |
|---|---|---|---|
| | | Mean | S.D. |
| none | none | 0.40 | 0.14 |
| LacI$^q$/trc | none | 3.84 | 0.57 |
| LacI$^q$/trc | +IPTG (30 mg/L) | 77.23 | 0.32 |

TABLE 3-continued

| regulator/promoter | Inducer | nmol/min/mg | |
|---|---|---|---|
| | | Mean | S.D. |
| AraC/AraBAD | none | 0.47 | 0.49 |
| AraC/AraBAD | +arabinose (1 g/L) | 5.51 | 0.46 |

The trc regulated construct shows uninduced activity. The araBAD regulated construct showed no uninduced activity and responded to arabinose. The araBAD promoter resulted in a β-galactosidase expression level that was 14-fold lower than that observed with the trc promoter in this organism.

Example 4

Use of β-Galactosidase Activity to Demonstrate the Response of the *C. glutamicum* aceB Promoter to Acetate, Glucose and Ethanol (98-0040002)

The ability of the *C. glutamicum* aceB regulatory region (SEQ ID NO:3) to control gene expression of a heterologous reporter gene in *C. glutamicum* was tested by measuring expression of β-galactosidase from plasmid pAceB10Zap2, produced as in Example 2(c). In this construct, the lacZ reporter gene, regulated by aceB, is expressed from a plasmid replicating in *C. glutamicum*. Response of the regulatory region to various inducers was tested. The results are shown in Table 4.

TABLE 4

| Rich Medium | nmol/min/mg |
|---|---|
| Minus sucrose | 10 |
| +2% glucose | 3 |
| +0.2% ammonium acetate | 26 |
| +2% ammonium acetate | 50 |
| +2% glucose + 0.2% ammonium acetate | 7 |
| +2% glucose + 2% ammonium acetate | 15 |
| +2% ethanol | 28 |

Glucose repressed reporter activity. Ethanol induced activity but not as strongly as acetate. The uninduced control also showed activity implying that aceB is self-regulated in this medium.

Example 5

Use of the trc Promoter to Regulate Aspartokinase Activity when Integrated into the Chromosome of *C. glutamicum* (90-004002)

The ability of the lacI$^q$/trc (SEQ ID NO:30) regulatory region to control expression of aspartokinase, an enzyme in the *C. glutamicum* L-lysine biosynthesis pathway (encoded by the ask gene), was tested as follows. The 131-2 and 131-5 *C. glutamicum* strains have the lacI$^q$/trc transcriptional regulatory region, in operable association with the ask gene, integrated into the *C. glutamicum* chromosome. These strains were prepared by introducing plasmid 131LacI$^q$/trc-ask into *C. glutamicum* by the methods described in Example 1. The level of aspartokinase activity was measured both with and without the addition of the inducer IPTG. The results are shown in Table 5.

TABLE 5

| Strain | Regulator/promoter-gene | Inducer | nmol/min/mg |
|---|---|---|---|
| 131-2 | lacI$^q$/trc-ask | none | 59 |
| 131-2 | lacI$^q$/trc-ask | +IPTG (30 mg/L) | 117 |
| 131-5 | lacI$^q$/trc-ask | none | 59 |
| 131-5 | lacI$^q$/trc-ask | +IPTG (30 mg/L) | 123 |

The level of aspartokinase activity is doubled upon induction when the trc regulon is integrated into the chromosome.

Example 6

Lysine Production by Integrated, Uninduced lacI$^q$/trc-ask Constructs (84-004002)

This example shows the influence on lysine production of the uninduced lacI$^q$/trc-ask construct when integrated into the chromosome of *C. glutamicum*. The lacI$^q$/trc regulatory region was used to control expression of aspartokinase (encoded by the ask gene), an enzyme in the *C. glutamicum* L-lysine biosynthesis pathway. Bacterial cultures of 131-2 and 131-5, prepared as described in Example 5, were grown in shake flasks. BF100 is *C. glutamicum* strain which is a high level lysine producer. The level of aspartokinase activity was measured without the addition of an inducer. The results are shown in Table 6.

TABLE 6

| Strain | Induction | O.D. | Titre | Yield | S.P. |
|---|---|---|---|---|---|
| BF100 | none | 43 | 23 | 39 | 53 |
| 131-2 | none | 34 | 27 | 46 | 82 |
| 131-5 | none | 35 | 28 | 47 | 82 |

O.D. = optical density at 660 nm
Titre = grams Lysine/liter
Yield = grams lysine made/grams dextrose consumed
S.P. = grams lysine/O.D.

The leakiness of the trc promoter in this organism may be responsible for the improved productivity in the absence of an inducer.

Example 7

Improvement of Lysine Production in Shake Flasks by aceB-Aspartokinase Constructs with No Exogenous Induction (84-0040002)

This example shows the influence on lysine production of an aceB-Aspartokinase construct when integrated into the *C. glutamicum* chromosome. The *C. glutamicum* aceB regulatory region (SEQ ID NO:3) was used to control expression of aspartokinase (encoded by the ask gene), an enzyme in the *C. glutamicum* L-lysine biosynthesis pathway. Bacterial cultures were grown in shake flasks. Strain 131-6 is a *C. glutamicum* strain which has the aceB transcriptional regulatory region in operable association with the ask gene, integrated into the bacterial chromosome. Strain 131-6 was prepared by introducing plasmid 131aceB/ask, produced as described in Example 2(d), into *C. glutamicum* by the methods described in Example 1. BF100 is *C. glutamicum* strain which is a high level lysine producer. The level of aspartokinase activity was measured either with or without the addition of the inducer acetate. The results are shown in Table 7.

TABLE 7

| Strain | Induction | O.D. | Titre | Yield |
|---|---|---|---|---|
| BF100 | none | 43 | 25 | 37 |
|  | acetate | 42 | 24 | 36 |
| 131-6 | none | 50 | 27 | 41 |
|  | acetate | 47 | 27 | 40 |

Titer = g lysine/L medium
Yield = g lysine/g glucose consumed * 100%

Induction by ammonium acetate is not required to observe an improvement in lysine production by this construct.

Example 8

Improvement of Lysine Production in Fermentors by aceB-aspartokinase Constructs with No Exogenous Induction (Lys002 Lys006RLK)

This example shows the influence on lysine production of uninduced aceB-Aspartokinase constructs which are expressed from a plasmid (PD10aceBask) replicating in *C. glutamicum*, or which are integrated into the *C. glutamicum* chromosome as in strain 131-6, described in Example 7. The *C. glutamicum* aceB regulatory region (SEQ ID NO:3) was used to control expression of aspartokinase (encoded by the ask gene), an enzyme in the *C. glutamicum* L-lysine biosynthesis pathway. Bacterial cultures were grown in fermentors. The *C. glutamicum* 131-aceB-aspartokinase strain, 131-6, has the aceB transcriptional regulatory region in operable association with the ask gene, integrated into the *C. glutamicum* chromosome. The *C. glutamicum* PD10-aceB-aspartokinase strain has the aceB transcriptional regulatory region in operable association with the ask gene, expressed from a plasmid (PD10aceBask, produced as described in Example 2(e)) replicating in *C. glutamicum*. BF100 is *C. glutamicum* strain which is a high level lysine producer. Aspartokinase activity was measured in each of these three strains. The results are shown in Table 8.

TABLE 8

| Strain | Titer | Yield | Product |
|---|---|---|---|
| BF100 | 127 | 32.9 | 735 |
| 131-aceB-aspartokinase | 129 | 39.8 | 833 |
| BF100 | 138 | 40.7 | 769 |
| PD10-aceB-aspartokinase | 135 | 45.8 | 830 |

Titer = g lysine/L medium
Yield = g lysine/g glucose consumed * 100%
Product = g lysine made in that fermented The aceB-aspartokinase constructs contributed to productivity whether they were maintained on a plasmid or integrated into the chromosome. In neither case did the constructs need to be induced by an exogenous compound.

Example 9

Influence of Medium on Beta Galactosidase Activity Using Various Use of LacZ as a Reporter to Demonstrate Transcriptional Regulation by the Regulatory Regions Contained in SEQ ID NOs 1,2, and 4–22 in *Corynebacterium*

The ability of certain transcriptional regulatory regions disclosed herein to control gene expression in *C. glutamicum* was tested by measuring expression of β-galactosidase. The promoters used include (SEQ ID NO: 27) Tac, (SEQ ID NO: 1) Pta, (SEQ ID NO: 2) AceA, (SEQ ID NO: 3) AceB, (SEQ ID NO:4) Adh, (SEQ ID NO: 5) AldB, (SEQ ID NO: 6) PoxB, (SEQ ID NO: 7) Ldh, (SEQ ID NO: 9) MalZ, (SEQ ID NO: 10) BglX, (SEQ ID NO: 13) HisD, (SEQ ID NO: 14) PyrR, (SEQ ID NO: 15) PurD, (SEQ ID NO: 18) DnaK, (SEQ ID NO: 20) GrpE, (SEQ ID NO: 21) ClpB, (SEQ ID NO: 33) LeuA, (SEQ ID NO: 34) IlvA and (SEQ ID NO: 35) IlvB. The reporter gene was expressed from plasmids replicating in *C. glutamicum*, and was driven by the regulatory regions contained in SEQ ID NOs 1,2, and 4–22. The plasmids were prepared as described in Example 2(g). Increased expression of beta-galactosidase under the transcriptional control of these transcriptional regulatory regions is shown in Table 9. The "Seed" Medium is experimentally determined to support high growth. The "Main" Medium is formulated to induce higher expression of products, such as lysine, for example. Exemplary medias were described supra.

For certain regulatory regions, β-galactosidase levels are measured without the addition or any inducer or in the presence of various inducers, e.g., acetic acid, pyruvate, ethanol, a starch subunit, a sugar, e.g., fructose, maltose, lactose or arabinose, a cellulose subunit, a fatty acid, or a triglyceride. In addition, certain regulatory regions are tested by growth with a suppressor, e.g., a purine, a pyrimidine, and amino acid, or oxygen, followed by a shift to medium lacking the suppressor at which time β-galactosidase levels were measured. For certain of the transcriptional regulatory regions, β-galactosidase levels are measured at optimal growth temperatures, and at temperatures either greater than or less than the optimal growth temperature. The β-galactosidase levels were measured using certain transcriptional regulatory regions at varying temperatures as shown in Table 10.

TABLE 9

Influence of Medium on beta-galactosidase Reporter Activity
(units = nmol/min/mg protein)

| SEQ ID NO | Promoter | Medium | | |
|---|---|---|---|---|
| | | Seed(16 hr) | Main(48 hr) | Change |
| | Promoterless | 2 | 20 | 19 |
| 27 | Tac | 231 | 342 | 111 |
| 1 | Pta | 134 | 111 | −23 |
| 2 | AceA | 0 | 63 | 63 |
| 3 | AceB | 0 | 25 | 25 |
| 4 | Adh | 0 | 65 | 65 |
| 5 | AldB | 9 | 260 | 251 |
| 6 | PoxB | 150 | 276 | 126 |
| 7 | Ldh | 205 | 291 | 86 |
| 9 | MalZ | 62 | 234 | 172 |
| 10 | BglX | 57 | 208 | 151 |
| 13 | HisD | 119 | 241 | 122 |
| 14 | PyrR | 161 | 289 | 128 |
| 15 | PurD | 9 | 56 | 47 |
| 18 | DnaK | 61 | 223 | 162 |
| 20 | GrpE | 40 | 149 | 109 |
| 21 | ClpB | 104 | 233 | 129 |
| 33 | LeuA | 174 | 267 | 193 |
| 34 | IlvA | 120 | 229 | 109 |
| 35 | IlvB | 22 | 166 | 144 |

TABLE 10

Effect of Temperature Change on beta-galactosidase Reporter Activity
(units = nmol/min/mg protein; mean (standard deviation))
temperature shift in seed medium for 4 hrs

| SEQ ID NO | Promoter | 30° C. | 36° C. | 40° C. |
|---|---|---|---|---|
|  | Promoterless | 0(0.7) | 0(0.2) | 0(0.7) |
| 21 | clpB | 76(7.3) | 123(2.5) | 165(1.6) |
| 18 | dnaK | 70(0.8) | 119(3.1) | 169(4.5) |
| 20 | grpE | 47(1.6) | 107(1.6) | 97(2.6) |

All 3 promoters increased reporter activity at 36° C.
All 3 promoters increased reporter activity at 40° C.
The grpE promoter doubled the activity at both 36° C. and 40° C.

Example 10

Improvement of Lysine Production Through Transcriptional Regulation of Aspartokinase by Regulatory Regions Contained in SEQ ID NOs 1,2, and 4–22

This example shows the influence on lysine production of induced or uninduced constructs in which the transcriptional regulatory regions of SEQ ID NOs 1,2, and 4–22 are used to express aspartokinase, either from a plasmid replicating in C. glutamicum, or when integrated into the C. glutamicum chromosome. The various C. glutamicum regulatory regions are used to control expression of aspartokinase, an enzyme in the C. glutamicum L-lysine biosynthesis pathway. Bacterial cultures are grown either in shake flasks or fermentors. C. glutamicum strains are prepared in which the transcriptional regulatory regions of SEQ ID NOs 1,2, and 4–22, in operable association with the ask gene, are integrated into the C. glutamicum chromosome. These strains are prepared by introducing plasmids 131 SEQ ID NO:1-ask, 131 SEQ ID NO:2-ask, and 131 SEQ ID NO:4-ask through 131 SEQ ID NO:22-ask, prepared as described in Example 2(h), into C. glutamicum by methods described in Example 1. Additional strains, with self-replicating plasmids are prepared by introducing plasmids PD10/SEQ ID NO:1-ask, PD10/SEQ ID NO:2-ask, and PD10/SEQ ID NO:4-ask through PD10/SEQ ID NO:22-ask, produced as described in Example 2(i), into C. glutamicum by methods described in Example 1. BF100, a high level lysine producer, is used as a control. Aspartokinase activity is measured in each of the resulting strains. For certain regulatory regions, aspartokinase levels are measured without the addition or any inducer, or in the presence of various inducers, e.g., acetic acid, pyruvate, ethanol, a starch subunit, a sugar, e.g., fructose, maltose, lactose or arabinose, a cellulose subunit, a fatty acid, or a triglyceride. In addition, certain regulatory regions are tested by growth either without, or with a suppressor, e.g., a purine, a pyrimidine, and amino acid, or oxygen, followed by a shift to medium lacking the suppressor at which time aspartokinase levels are measured. Finally, for certain regulatory regions, aspartokinase levels are measured at optimal growth temperatures, and also at temperatures either greater than or less than the optimal growth temperature.

Having now fully described the present invention in some detail by way of illustration and example for purposes of clarity of understanding, it will be obvious to one of ordinary skill in the art that same can be performed by modifying or changing the invention with a wide and equivalent range of conditions, formulations and other parameters thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated polynucleotide comprising a first nucleic acid sequence operably associated with a second nucleic acid sequence, said first nucleic acid sequence consisting of a the nucleotide sequence that is:
   (a) at least 95% identical to the reference nucleotide sequence set forth in SEQ ID NO:7; or
   (b) identical to the reference nucleotide sequence set forth in SEQ ID NO:7;
   wherein said first nucleic acid sequence has the function of a promoter that regulates transcription of said second nucleic acid sequence in response to pyruvate.

2. The polynucleotide of claim 1, wherein said polynucleotide regulates transcription of β-galactosidase in a bacterial host cell.

3. The polynucleotide of claim 1, wherein said second nucleic acid encodes a polypeptide.

4. The polynucleotide of claim 3, wherein said polypeptide is selected from the group consisting of: (a) a polypeptide, which is a component of an amino acid biosynthesis pathway; (b) a polypeptide, which is a component of a purine nucleotide biosynthesis pathway; and (c) a heterologous polypeptide.

5. The polynucleotide of claim 4, wherein said polypeptide is a component of an amino acid biosynthesis pathway.

6. The polynucleotide of claim 5 wherein said amino acid biosynthesis pathway is a lysine biosynthesis pathway.

7. The polynucleotide of claim 5, wherein said polypeptide is selected from the group consisting of: (a) aspartokinase, (b) diaminopimelate dehydrogenase, (c) diaminopimelate decarboxylase, (d) dihydrodipicolinate synthetase, (e) dihydrodipicolinate reductase, (f) aspartate beta-semialdehyde dehydrogenase, and (g) pyruvate carboxylase.

8. A method of producing a vector which comprises inserting the polynucleotide of claim 1 into a vector.

9. A vector comprising the polynucleotide of claim 1.

10. A vector comprising the polynucleotide of claim 3.

11. A vector comprising the polynucleotide of claim 4.

12. An isolated host cell comprising the vector of claim 9.

13. The host cell of claim 12, wherein said host cell is a *Corynebacterium* species.

14. An isolated host cell comprising the vector of claim 10.

15. An isolated host cell comprising the vector of claim 11.

16. A method of producing an isolated transformed *Corynebacterium* species host cell comprising: (a) introducing into *Corynebacterium* species cells the vector of claim 15, and (b) selecting said host cell.

17. A method of production of a biosynthetic product, comprising culturing the host cell of claim 16 in or on a culture medium, and recovering said product.

18. An isolated polynucleotide comprising a first nucleic acid sequence operably associated with a second nucleic acid sequence, said first nucleic acid sequence consisting of the nucleotide sequence at least 90% identical to the sequence set forth in SEQ ID NO: 7, and wherein the −10 region of said nucleotide sequence consists of the sequence TACAAT and wherein the −35 region of said nucleotide sequence consists of the sequence TTGCCAA, wherein said first nucleic acid sequence has the function of a promoter that regulates transcription of said second nucleic acid sequence in response to pyruvate.

19. The polynucleotide of claim 18, wherein said polynucleotide regulates transcription of β-galactosidase in a bacterial host cell.

20. An isolated polynucleotide comprising a first nucleic acid sequence operably associated with a second nucleic acid sequence, wherein the sequence of said first nucleic acid consists of at least 50 contiguous nucleotides of SEQ ID NO:7.

21. The polynucleotide of claim 20, wherein said first nucleic acid sequence consists of at least 150 contiguous nucleotides of SEQ ID NO:7.

22. The polynucleotide of claim 20, wherein said second nucleic acid encodes a polypeptide.

23. The polynucleotide of claim 22, wherein said polypeptide is selected from the group consisting of: (a) a polypeptide which is a component of an amino acid biosynthesis pathway; (b) a polypeptide which is a component of a purine nucleotide biosynthesis pathway; and (c) a heterologous polypeptide.

24. The polynucleotide of claim 23, wherein said polypeptide is a component of an amino acid biosynthesis pathway.

25. A method of producing a vector which comprises inserting the polynucleotide of claim 20 into a vector.

26. A vector comprising the polynucleotide of claim 20.

27. An isolated host cell comprising the vector of claim 26.

28. The host cell of claim 27, wherein said host cell is a *Corynebacterium* species.

29. A method of producing a transformed *Corynebacterium* species host cell comprising: (a) introducing into *Corynebacterium* species cells the vector of claim 26, and (b) selecting said host cell.

30. A method of production of a biosynthetic product, comprising culturing the host cell of claim 27 in or on a culture medium, and recovering said product.

* * * * *

SEQUENCE LISTING

```
<160> NUMBER OF SEQ ID NOS: 35

<210> SEQ ID NO 1
<211> LENGTH: 500
<212> TYPE: DNA
<213> ORGANISM: Corynebacterium glutamicum

<400> SEQUENCE: 1
caccgacaac ggcaacacgc aaagggcgag acatataaag ttcgattcct taaagggtt       60 ctaaaaaatg tggagtatgt gagcggggtt ccactagtag attcgactcc tatcggggtg     120
cgactgctaa tggtgccctg ctatcaaccc tccatgatac gtggtaagtg cagactaata     180
aaggccagtc ggggaggatt gggggctttg ctggggcag atttgtcacg ctgcgcgctt      240
tcatagaccc cattaatgtg gggtgaagag ctgtaaagta ccgctaaaaa ctttgcaaag     300
ggtgcttcgc aacttgtaac cgctccgtat tgttttctac ggcaataagc atttgtgctg     360
ctcaaagcgt ggaattgaga tcggtttgaa aattacaaaa taaactttg caaaccgggc      420 tgtacgcaag gcgacgaac gctaaactat gtaagaaatc acaacttccc ctcagtagtg     480
ccaggaggca caagcctgaa                                                 500
```

<210> SEQ ID NO 2
<211> LENGTH: 500
<212> TYPE: DNA
<213> ORGANISM: Corynebacterium glutamicum

<400> SEQUENCE: 2

| | | | | | | |
|---|---|---|---|---|---|---|
| actcttttaa | gaaaagcact | ctgactacct | ctggaatcta | ggtgccactc | ttctttcgat | 60 |
| ttcaacccctt | atcgtgtttg | gcgatgtgat | cagactaagt | gatcaccgtc | accagcaaaa | 120 |
| ggggtttgcg | aactttacta | agtcattacc | cccgcctaac | cccgactttt | atctaggtca | 180 |
| caccttcaaa | acctacggaa | cgttgcggtg | cctgcatttt | cccatttcag | agcatttgcc | 240 |
| cagtacatct | gtactagcaa | ctcccccgcc | cactttttct | gcgaagccag | aactttgcaa | 300 |
| acttcacaac | agggtgacc | accccgcac | aaaacttaaa | aacccaaacc | gattgacgca | 360 |
| ccaatgcccg | atggagcaat | gtgtgaacca | cgccaccacg | caaaccgatg | cacatcacgt | 420 |
| cgaaacagtg | acagtgcatt | agctcatact | ttgtggttgg | caccgcccat | tgcgaatcag | 480 |
| cacttaagga | agtgactttg | | | | | 500 |

<210> SEQ ID NO 3
<211> LENGTH: 500
<212> TYPE: DNA
<213> ORGANISM: Corynebacterium glutamicum

<400> SEQUENCE: 3

| | | | | | | |
|---|---|---|---|---|---|---|
| ttgcgtggtg | gcgtggttca | cacattgctc | catcgggcat | tggtgcgtca | atcggtttgg | 60 |
| gttttttaagt | tttgtgcggg | ggtggtcacc | cctgttgtga | agtttgcaaa | gttctggctt | 120 |
| cgcagaaaaa | gtgggcgggg | gagttgctag | tacagatgta | ctgggcaaat | gctctgaaat | 180 |
| gggaaaatgc | aggcaccgca | acgttccgta | ggttttgaag | gtgtgaccta | gataaaagtc | 240 |
| ggggttaggc | gggggtaatg | acttagtaaa | gttcgcaaac | cccttttgct | ggtgacggtg | 300 |
| atcacttagt | ctgatcacat | cgccaaacac | gataagggtt | gaaatcgaaa | gaagagtggc | 360 |
| acctagattc | cagaggtagt | cagagtgctt | ttcttaaaag | agttttcaca | accgttaacg | 420 |
| gcgtagccaa | acaagaagga | ttcgcattct | tctggtttag | gcacaggtca | tctaaaccca | 480 |
| tgctttaaaa | ggagccttca | | | | | 500 |

<210> SEQ ID NO 4
<211> LENGTH: 500
<212> TYPE: DNA
<213> ORGANISM: Corynebacterium glutamicum

<400> SEQUENCE: 4

| | | | | | | |
|---|---|---|---|---|---|---|
| attggaaaat | ggagattaga | agaatcctgg | gaatgttggt | gtgtgttgca | tgtctgttga | 60 |
| gactatctag | tagatgcggc | tgcgctcctt | aattgcatgc | tggggtggtg | gggaatgggt | 120 |
| ggttgggggc | gtcgaaaagc | attttttggtg | cttctaaggg | aattgtgtga | atcttggaaa | 180 |
| gctaattgaa | aaacattccc | attagtgggt | gatttgctgg | agttttgtga | atctattttt | 240 |
| cgaaatttca | gcgtgcgggg | gtggtttgtt | tttttacaat | tgccagttca | ttcacgttg | 300 |
| ttgaaatgtt | cggggtaat | aactcaactt | tctattttca | ccttgttggg | atttcgctag | 360 |
| ggtggacgat | ggcagcaatt | gaatgttgta | aatcacacaa | ttgcaaggat | tgtaatttaa | 420 |
| ggcacatcta | tgtcggtgtg | aaattacatg | tgccagaaga | gcaatttgcc | aagtaatcca | 480 |
| agcgagaagg | agtgagtttt | | | | | 500 |

<210> SEQ ID NO 5
<211> LENGTH: 500
<212> TYPE: DNA
<213> ORGANISM: Corynebacterium glutamicum

<400> SEQUENCE: 5

| | | | | | | |
|---|---|---|---|---|---|---|
| cgatcatcga | actcggcgaa | gaaaaccgaa | acctcaaaga | atccctgcgt | aaggtcacag | 60 |
| ctgagaatga | gcagctcaaa | gatcaattac | gcagcgggcg | tccgcgtggc | gagctggtgc | 120 |
| acgtgccccg | ctccaccgcg | gtggtcatgt | gggaacgccg | caagggcgt | tccaagtaaa | 180 |
| aacatgcttg | tcgacgccgc | tttctagcaa | attaagcggg | cacctccatt | tatcttttgg | 240 |
| aggtgcccgt | ttcgtgcttt | cgccaattag | atacatgcat | aaccacccga | acaggggtaa | 300 |
| taacttttga | aaggctttcg | gcgttgagct | gcgagaattt | tgagaaaagg | gggtgaattt | 360 |
| aacaggggtt | ctagcgcgga | ttgattttcg | tgaatatggt | ggctgctaag | cgtgcgaatg | 420 |
| tgcgcgttat | cacaatcgtt | gaccaagtgt | cacctgacgc | acaggtagtg | ctcaggtgga | 480 |
| ggtggcccaa | aggagaccca | | | | | 500 |

<210> SEQ ID NO 6
<211> LENGTH: 500
<212> TYPE: DNA
<213> ORGANISM: Corynebacterium glutamicum

<400> SEQUENCE: 6

| | | | | | | |
|---|---|---|---|---|---|---|
| ttttagacca | cggcgctgtg | tgggattta | agacgtcgga | aattgtaggg | gactgtcagt | 60 |
| gtgagtcggg | ttctttgagg | cgcttagagg | cgattctgtg | aggtcacttt | ttgtggggtc | 120 |
| ggggtctaaa | tttggccagt | tttcgaggcg | accagacagg | cgtgacaaga | ttgactaaaa | 180 |
| aaccgaagtt | ttggcacgtg | tgtttggttt | ctcggggtct | aaaccggaca | ggcgtgacaa | 240 |
| gatctggcga | aatcgcaggt | ttttgtcacg | cctgtctggt | tttaccttt | gggggcccga | 300 |
| actgccctga | actactcgga | tcgaccaagc | agtttggcct | ccagcgctct | gatcaagcac | 360 |
| ccaaccgcct | ctaaatcaca | ccaaggcact | cgtaaaaccc | gtggcagata | gagaaagtgt | 420 |
| ggcagcaact | cgaattgaag | agcacaattg | aagtcgcacc | aagttaggca | acacaatagc | 480 |
| cataacgttg | aggagttcag | | | | | 500 |

<210> SEQ ID NO 7
<211> LENGTH: 500
<212> TYPE: DNA
<213> ORGANISM: Corynebacterium glutamicum

<400> SEQUENCE: 7

| | | | | | | |
|---|---|---|---|---|---|---|
| aaaacagcca | ggttagcggc | tgtaacccac | cacggtttcg | gcaacaatga | cggcgagaga | 60 |
| gcccaccaca | ttgcgatttc | cgctccgata | aagccagcgc | ccatatttgc | agggaggatt | 120 |
| cgcctgcggt | ttggcgacat | tcggatcccc | ggaaccagct | ctgcaatgac | ctgcgcgccg | 180 |
| agggaagcga | ggtgggtggc | aggttttagt | gcgggtttaa | gcgttgccag | gcgagtggtg | 240 |
| agcaaagacg | ctagtctggg | gagcgaaacc | atattgagtc | atcttggcag | agcatgcaca | 300 |
| attctgcagg | gcatagattg | gttttgctcg | atttacaatg | tgattttttc | aacaaaaata | 360 |
| acacttggtc | tgaccacatt | ttcgacata | atcgggcata | attaaggtg | taacaaagga | 420 |
| atccgggcac | aagctcttgc | tgattttctg | agctgctttg | tgggttgtcc | ggttagggaa | 480 |
| atcaggaagt | gggatcgaaa | | | | | 500 |

<210> SEQ ID NO 8

<211> LENGTH: 500
<212> TYPE: DNA
<213> ORGANISM: Corynebacterium glutamicum

<400> SEQUENCE: 8

| | | |
|---|---|---|
| ccagatctcg ggatgcttcg tagatcagca tggcgccgag gtcgttggct gctgcacgga | 60 |
| aagctgcgtt gtcgctgcgc tcgtcgcgca cagggggtag gcggctagca acgagtgggt | 120 |
| ggttgacgat ggtgatgtcc atagcttcac atgttaaatc attgccgccc agaagaagac | 180 |
| cgcgcgggcg aatttgggct tggagggaac caaacggcca cttttccagt ccaacaaagt | 240 |
| atgaggatta atttgcccca ctccaaagag ctcgcccacg agctgtgttt gttgcccacc | 300 |
| cctgctgtgc ccgcgcttcc cactgattct ggcgcgcagt ttgatatcca ccaggcactg | 360 |
| tccgcctctc ttgccaccta tgcccgcaac ctcaccttgc tgtcccacac cgccgagaat | 420 |
| ttaggaaacc gcgctctgac cggcctcgct gaaatcgaag acaccgacga ccaactcgca | 480 |
| cacgcattgg agcgcctgac | 500 |

<210> SEQ ID NO 9
<211> LENGTH: 1583
<212> TYPE: DNA
<213> ORGANISM: Corynebacterium glutamicum

<400> SEQUENCE: 9

| | | |
|---|---|---|
| gggcatcatg ggcattgttg gtggattcac catgcctgtc gcaatcgcta ggaccaggga | 60 |
| taagaacctc gtgtggttcc ccgtggtctt tggtgcatcg atgttcctcg gttatgtggg | 120 |
| aacgtggctg tggccgtccc aaggctggta cctgtggtca ttccttcttg gtttaggtgg | 180 |
| actctgcttc ccgatggcta tcgccctgat tccagcgcgt acgaaagatc cgagaattac | 240 |
| cgcaagcttg tctggatttg tgcagccggt gggttacatt cttgcagccc ttgggccatt | 300 |
| ggcagtggga gcgatctacc aggcgattgg ctccctggtca gagatcctcg ttggtttggc | 360 |
| cttgggcaca atagtgttgt cgattgtggg attcagagca gcacgcaatg tgacggttga | 420 |
| tgatgaattg aggagatcaa agtagcctca actaagcgtc gcgataagaa cgaggggcaa | 480 |
| ggctgatgta ctctgtcaac catggataaa ccggtcgtga gggatgcagc tctgctgatt | 540 |
| tttcgcgctg tgctcggagt gatctttgtg gcacacgggt gggaaaagct gttcatctcc | 600 |
| ggagttacca agacaacagg acaatttttca gcctggggag tgcctcaacc caagctctcg | 660 |
| gtgtggatca catcgatctc tgagctgctc ggtggtgcct tcctagtggt tggtttgctc | 720 |
| accaccttg ttgctggtgc attagcgctg ttgatcgccg ctgctatta ctttgtgcac | 780 |
| ttgagttcgg gcttttttcac agttgataac ggcatcgaat tccccttgct catcattgtt | 840 |
| tctttgctcg tgatcgttgt gtttggttct ggtagagcca gcgttgatgg ggtgctcacg | 900 |
| cgtggttgac tgtagtgcca ttcaagccgc gctgtccgcc aaattagatg gtgagccgac | 960 |
| aggcttggat gatgcagtaa ttgaagcgca cctcgctaat tgtgaagagt gcagaaatta | 1020 |
| ctacaaccgt gctgctgagt tgaatcggat gctcaatttt tgcgccgcgg aacctcgcac | 1080 |
| cctgaccccg cctgatctat cagagatcat tctggcagag gtggaaccag aatgcgcag | 1140 |
| gcatgccaac gccaaggttg tgggatccct gctatcgcga tgttgttgg tgatcctggg | 1200 |
| tgtggtttac ctcgcctggg gtatcacaat gttggggggat cggcgtcga taagcgtcca | 1260 |
| agaagacccg ctcacctcgc gcctgctcgc ggaggccgtt gcctaccgca ttgctctttc | 1320 |
| tgtggggctg ttatttgcgg cgtggaagcc gcggattatc gcgggcatgc tcccgatttt | 1380 |
| tggaacgttg tggacatttta gtgctggttt tgctgcgcgc gatctcgtgt ttggcgtcgc | 1440 |

```
cgattcacag acgggactgt ccattggtct gctgttgatt tctacgattg tgctgtcgtt    1500
tgcgttggtg aatagttctg gaccgggtat tttgcggcgc acatggaact cattgaacgc    1560
cgcgcccggc taaggtggga ggc                                            1583

<210> SEQ ID NO 10
<211> LENGTH: 500
<212> TYPE: DNA
<213> ORGANISM: Corynebacterium glutamicum

<400> SEQUENCE: 10
taatacggca tccggcctga aaggacagtg tggaacccaa aaatcatgcc ctcgcagaat     60
cgtgtttaag gggttaaaac gcctcgaccc acactctgac ccatccgtga aactagacct    120
cttaaaacga cttctggttg gtgaggtgtg aaaaccgcac tgcggggccc aattcacaaa    180
aatccatacg agtgtgcaca cccgattttc acatcgcttc gagacctccc tttttgacac    240
cttaattgtc taaccccgta taggtgagaa atgttggaca agtgtctgtt tttgtggggg    300
gaatctgact acgatggtaa gaaacaggga aaggggttac cattatgtct caagagtagc    360
ctcaaatcgg ctcccgcctc tctcgtgtca ttgaacaaga cggcctacaa ttccgcgatc    420
tcgacggcga cggcgtactt gcaccttatg aagattggcg tctaaccccca gcagagcgtg    480 ccgctgacct ggtgaaacga                                                500

<210> SEQ ID NO 11
<211> LENGTH: 500
<212> TYPE: DNA
<213> ORGANISM: Corynebacterium glutamicum

<400> SEQUENCE: 11
caccgcgtcg ccgatctctc ccttccagac tcagaagttg cttcggcaat tgcacttgag     60
tggaaaccag gcgtcggatt cactacttga gctgctgatt tgtaggtttt aagaccttga    120
agatatagtt aattctcgtt gcaaggaacc agattccaag caatgcgtat tcctccatag    180
ctcagttggc agagcattcg actgttaatc gaagggtcac tggttcgagc ccagttggag    240
gagcaaattg aaacccactg ttttttaaca gtgggttttt ttgcatgttt catacagtta    300
acgaacccca attttgtaac ttccactctc ctagctatga tgaatactcg ttgcaaggaa    360
gtaattcctt tccaatactt attcctccat agctcagttg gcagagcatt cgactgttaa    420
tcgaagggtc actggttcga gcccagttgg aggagcaata cacacagccc gccgtttttc    480
ttaaaacggc gggttttgtt                                                500

<210> SEQ ID NO 12
<211> LENGTH: 1083
<212> TYPE: DNA
<213> ORGANISM: Corynebacterium glutamicum

<400> SEQUENCE: 12
ggtgtcagtg tatccgcgaa ccagagcctc gatggcagct gtgtcttctg gggaagcggt     60
ctggccgttt tcaactggcg cagcttcagc gaaggtaatt gggttctcag acagctcttg    120
tgacagtaca tcaagctgtg cttgctgctc ttcgttgatg gttgttgctt cggaagattc    180
agattcagat tcagattcgg acgaggtggt ttctgctgct tccgccgagg tcgttgcgct    240
ggaagaggaa gaatttgtcg tcgtcgctgc gctggatgag gctgcttctg tatcagatga    300
ctcactgcta catgcggtta agagaagtgg ggtgaccatg agtgctgcga aagcagcctt    360
```

```
ctttgaggaa aggcgaatag acaaagttct gctcctgata aatcatcgac atgctccgga    420
aaacttaaaa attcccggac ggttcacgca gattacccta gcaaagcaat ctagctgacg    480 acccaatttta gtcctgtcat tatgctggca attgtgcagc tatctaaaga atctattatt    540
ggggcagccg tttcgatcct gagcgagttc ggtttgtcgg atatgaccat gcgtcgcgtc    600
gcaaagcaat taaatgtcgc gccgggcgcg ctgtattggc attttaaaaa taagcaggag    660
cttatcgacg ccacctcacg ccatctcctg gcgcctatct ggggcgcaa cgacgagcag    720 cgagcaagca tttccgcgca ggaaacgtgc gcagaaatgc gttcactgat gatgcaaacc    780
aaagacggtg cggaagtcat cagtgccgca ctgagtaatc agcaactgcg ccaagaattg    840
gaatctctca tttccgactc tttaaaagaa cctaatgagg tcggtgcttt tacgctgctg    900
cattttgtgg tgggtgcagt attaacagaa caaactcagc tgcagatgca cgagttcacg    960
gctggcgcgg aagatgacac acaagaaaac cctgccgatg cgaactttga ggagagattc   1020
aatcaaggat tagaaatcat tctggcgggt ctagacgcgc ttgggcatat aagatagcgt   1080
tct                                                                 1083

<210> SEQ ID NO 13
<211> LENGTH: 500
<212> TYPE: DNA
<213> ORGANISM: Corynebacterium glutamicum

<400> SEQUENCE: 13
agtgacagct cgcgccgcat cgttgatggc aaacatgtcc aaattaaggc gcatgcgacc     60
aaggatggtg agcatttgcc ctgattcgtg gctgaagtac atcgaaatgc ggtgatcttg    120
ccacggcacg atgatgcgat cttctgagct caaatagtgg tagcccaagg aatcaacagc    180
ctccgtcact cgattcaggt caactgggaa aggaatggag gtgttgggtg cagggacgtt    240
tcgatcattc acagaggtga aatccattcc ttccagtatc tcaaaggtga agcgggttt     300 aattcaggta aatctggggt ggtcatttta agttttaagt ctaattcaaa tgaactctga    360
tgtacccaaa tcagaaactt gttacgtggg gaatacaata ggtaaatatg cgggcttaag    420
aacttgtgtt gaggccgctt ggattcgggc accgagctcg aagaatttcg attcaacctt    480
ttaagggaga acttttcgcc                                                500

<210> SEQ ID NO 14
<211> LENGTH: 500
<212> TYPE: DNA
<213> ORGANISM: Corynebacterium glutamicum

<400> SEQUENCE: 14
cgtggcgtgc cacccattta agtcccgcgg ggagactgaa gatggtggtg ccgtcggcga     60
ggcgttctgc ctgcgtaatg gggttaagtg ggatgaacgg gggagtcaga cgtgcgacag    120
cgcccttgcg ggtatgccaa tcccagacca tttctcgggg aaaaggaata aaatggcttg    180
tggtcagact cacaggggct ctccaagtc agtggattta tgaggtccca gtgggtacac     240
accgggtgtc ctacaacgat caattgtcac agattcgact ggcatgctgt accatctgct    300
ttaagcattt tggtgtttca ctgttgttaa cagtgtttca ccgtggagca ctaccttaga    360
tcatagtcag catcttgggg tgaatgtgac acggtacgct atagtgtcag acaacaacca    420
ggaaactggt cgttgcagag ttttttgcaaa attggacatc ctttaacgga ccgcacagag    480
aggcggggaa ggaggtcacg                                                500
```

<210> SEQ ID NO 15
<211> LENGTH: 500
<212> TYPE: DNA
<213> ORGANISM: Corynebacterium glutamicum

<400> SEQUENCE: 15

```
gccatggcgt tgcggaaatc gtaatcggcc attttgtcgg tggggaagag gtggatgtga      60
gtgtggggaa catcgaatcc tgcgatgatg taaccacatc gagggcgtc gaatgctgtg     120
cggattgcat ttccgatgag ctgggaggcc tcgtttactt cgctccagat gttctgagga     180
aggtcggtcc agcggtcaac ttctgcaacg ggtacgacta gggtgtggcc gtaggtgagg     240
ggttcgatgg atagaaaagc cacgacattc tcggaacgat acacaaatcg gccggggagc     300
tcgccattaa taattttcgt gaatacagaa gccatatgca cagactacta cttggcgtgc     360
aaccaaattg aggttgcata aataatgca ggtgagccgg tcattttaag gcgcttttcg     420
acgccacttt caaccatttc cgaaccgcca agaatactgg aatagcttgg atcaagtttt     480
gcaggataaa ctgtgcaacc                                                 500
```

<210> SEQ ID NO 16
<211> LENGTH: 500
<212> TYPE: DNA
<213> ORGANISM: Corynebacterium glutamicum

<400> SEQUENCE: 16

```
acgctgatcg ttttgagctt atcgacgctc gcctgcgctc agctggtttc gattggtacg      60
aggtatccaa ctgggcgaaa cccggcggag aatgcaagca caacatgggc tattgggtcg     120
acggcgactg gtggggtgct ggcccgggcg cgcactcgca catcggcgac cgccgcttct     180
acaacatcaa gcacccagcg cgttactccg cgcagattgc ggccggcgag ctgcccatta     240
aggaaacaga gcggctgacg gcggaagatc accacaccga gcgcgtcatg cttggtttgc     300
gcctgaaaca aggcgtgccg ctgaaccttt tcgcacccgc agcgcgcccg gtcatcgacc     360
gtcatatcgc aggaggcctg ctgcacgtca atgcgctggg caacctggcg gtgaccgatg     420
cgggacgttt gcttgccgac ggcatcatcg ccgacatttt gcttagtgaa gaagactaaa     480
tatttagtag ggttacagac                                                 500
```

<210> SEQ ID NO 17
<211> LENGTH: 500
<212> TYPE: DNA
<213> ORGANISM: Corynebacterium glutamicum

<400> SEQUENCE: 17

```
tggcgactat gccacatagt cgactacctt gcatagttga ctatttgatt gagttgaact      60
gtgtcagtgt atgaagagaa aaatgaagag aaaaacagct gcacatggtt tcaaaagata     120
aggaagtgaa gcatgagcat cgagccagga atccccacgc ttggaccgct tgaagaacaa     180
gtcatgcaca ttctgtggga tcacggaaaa ttgacagtcc gtgaagtcat cgaattcctt     240
ccaggtgatc ctgcgtacac aacgatcgca accgtcctgc gtcacttggg cagaaaaggc     300
atggtcacca ttgtgaaaga tggtcggact gctcgacaca gcgcgttgat gaacagggaa     360
gaatacaccg ctggcgtcat ggatcaggtg ctgtcgacca gtcgggatcg caccgcatca     420
attctgcatt tcgtggatac gatcacggcg actgatcgcg agctgcttct ggagtatctg     480
caacagcagg agggcaggaa                                                 500
```

<210> SEQ ID NO 18

<211> LENGTH: 297
<212> TYPE: DNA
<213> ORGANISM: Corynebacterium glutamicum

<400> SEQUENCE: 18

```
agacttggcg tcaaagttga gtgggacctg ttgaaaacag ctcgtatctt ccctgattgg     60
gtggttgaaa ttaggggtaa acccggattt tttctcaagt gaagcgcttt gacctgtgta    120
aattaagaaa gttgagtcta gtgggaacaa ctttgtggca tttaccgttg ccatatatgt    180
aagcttgagt caggcaggct caatgaggag ttttcttac cggcgaaagt cggtggaagc     240
aagtcaaagc tcaagccgtg acaatacta aaatcaccta aacaggagg caccatt         297
```

<210> SEQ ID NO 19
<211> LENGTH: 500
<212> TYPE: DNA
<213> ORGANISM: Corynebacterium glutamicum

<400> SEQUENCE: 19

```
cgggagccgt tcttctccac gatggggcgc tcggtgaaat cactgaaacg cgcggtttcc     60
agaagcatca ccacgatggc gtcactgacc tcaaaagatg cagtgtgctc atcactgaag    120
acggtgtttt ctttgaagcc aagacctgca taaaaaacgc ttagatgctg caaggtcaga    180
tactggtagg ttgatgaaaa tcatgtcgtg ctgaagtcgt gccatgggag ttccacttcc    240
tcaaagtgcc ttttggctaa tgtgaccccca accagtatgc tgccggtttt tggattaggt    300
ttggccatcg tgctagcata tttaggtctc ggcgagggtc aagtactttt agtgctcaac    360
cgttatcgac gcgatctaga cttctaaagt gcacttttgt gcgctgcctg cgaagactcg    420
accaagacat tcgagtcggt cgcgggcatt ttttattttc gcggccgagt gtccaccttc    480
atccatgagg agaaatcact                                                 500
```

<210> SEQ ID NO 20
<211> LENGTH: 500
<212> TYPE: DNA
<213> ORGANISM: Corynebacterium glutamicum

<400> SEQUENCE: 20

```
tggattgtct ggcggacaaa gttcgcaccg ataaacccgg caccaccggt cacaagcaaa     60
gaagtcatgg tcgtcatagt agttgcggct cctgcagttg cgcgtgttat cgctgacggg    120
catgtcaatt cagccgtgac ccagcttcgg tgcggtgtga aaacgtatgg ggaaaagcca    180
cggatagtgc atgcccactt ctccacatgg gctgtgctca gctgtcgtag gggccacggc    240
ttgcggactt tctgaacacc cggacgaaag cctccattat tgatggcacc cacccggggg    300
tggtatcggt tgctaagttc acagtggtcg gagagaataa gtcagcactt ctgattacat    360
gtacgaaatc agggcggtca aatgccagtt cccacccggc ttcactaagg cgggacgacc    420
atagaaacgc agcttctgac attgaatgcg ccggtttgct atggactaca ccgcatatga    480
ggaaagggct tgaaacgcac                                                 500
```

<210> SEQ ID NO 21
<211> LENGTH: 500
<212> TYPE: DNA
<213> ORGANISM: Corynebacterium glutamicum

<400> SEQUENCE: 21

```
cttaatgagt acggcgtggc ttatatcggt ttcgctccgt ttgaaatcgg catgaccatc     60
atcgcgccga tcgcggtgct cgcaggcttt actatggggt tgggttgggc gtcgttgatt    120
```

-continued

```
gttgcgatcg tgattttggg cctcgcgtgg ggtctgaagt ggttgccgga gcgcggacat      180
gtccgcggcg agggtaagcc gcaataaagg ttggaagcgc cgggtctagg tccggcgctt      240 cttcgtacg cttttcgacg cctccctcca cgtaatatta aagttacggg ttttccctga       300
tgcttaagtg gtagtcagtg cttaaacttg actgcggtcc actcaattta ttttcaaatt     360
ttttgaactt gagtggaaca tactcaactc tttgtgcgtt atagatatta gagagttaaa     420
taatggcgct tgacctgcag gaaattgaga tcaacactga ttgtgtaggt tggcgcccaa     480
caaagaaagg gcgttgaaag                                                  500

<210> SEQ ID NO 22
<211> LENGTH: 500
<212> TYPE: DNA
<213> ORGANISM: Corynebacterium glutamicum

<400> SEQUENCE: 22
tggccattcc tgtggtccat gctcgccctg ttcttcttca ctggactggg caacgccggc      60
acattcaaac aaatgcccat gattttgccc aaacgccaag caggtggcgt gatcggctgg     120
accggtgcca ttggtgcctt cggcccttc attgtcggtg tcttgctctc cttcactcca      180
actgtcgcgt tcttctgggg ctgcgtggtg ttcttcatca tcgccaccgc tttgacctgg     240
atctactacg cccgcccgaa cgctccattc ccgggataaa ccgaaaggcc aatccatgac    300
tacaactact tcttctggga agtcttctga acagtcttct gaaaagatca acccctctt    360 caagctcggc agtttcctaa gaaaaggcac cgtcggttct gaaggccagc agattttcct    420
tcagggcgga cgccaagccg atgtgttttt atcgcaaccc gatgggcgtt cgataaaagt    480
cgtgcgctcc cacacatggc                                                  500

<210> SEQ ID NO 23
<211> LENGTH: 1285
<212> TYPE: DNA
<213> ORGANISM: Escherichia coli

<400> SEQUENCE: 23
tgcataatgt gcctgtcaaa tggacgaagc agggattctg caaaccctat gctactccgt      60
caagccgtca attgtctgat tcgttaccaa ttatgacaac ttgacggcta catcattcac     120 ttttcttca caaccggcac ggaactcgct cgggctggcc ccgtgcatt ttttaaatac       180 ccgcgagaaa tagagttgat cgtcaaaacc aacattgcga ccgacggtgg cgataggcat     240
ccgggtggtg ctcaaaagca gcttcgcctg gctgatacgt tggtcctcgc gccagcttaa     300
gacgctaatc cctaactgct ggcggaaaag atgtgacaga cgcgacggcg acaagcaaac    360
atgctgtgcg acgctggcga tatcaaaatt gctgtctgcc aggtgatcgc tgatgtactg    420
acaagcctcg cgtacccgat tatccatcgg tggatggagc gactcgttaa tcgcttccat    480
gcgccgcagt aacaattgct caagcagatt tatcgccagc agctccgaat agcgccttc     540 cccttgcccg cgttaatga tttgcccaaa caggtcgctg aaatgcggct ggtgcgcttc     600
atccgggcga agaacccccg tattggcaaa tattgacggc cagttaagcc attcatgcca    660
gtaggcgcgc ggacgaaagt aaacccactg gtgataccat cgcgagcct ccggatgacg    720 accgtagtga tgaatctctc ctggcgggaa cagcaaaata tcacccggtc ggcaaacaaa    780
ttctcgtccc tgatttttca ccaccccctg accgcgaatg gtgagattga aatataacc     840 tttcattccc agcggtcggt cgataaaaaa atcgagataa ccgttggcct caatcggcgt    900
```

-continued

```
taaacccgcc accagatggg cattaaacga gtatcccggc agcagggggat cattttgcgc    960 ttcagccata cttttcatac tcccgccatt cagagaagaa accaattgtc catattgcat   1020
cagacattgc cgtcactgcg tcttttactg gctcttctcg ctaaccaaac cggtaacccc   1080
gcttattaaa agcattctgt aacaaagcgg gaccaaagcc atgacaaaaa cgcgtaacaa   1140
aagtgtctat aatcacggca gaaaagtcca cattgattat ttgcacggcg tcacactttg   1200
ctatgccata gcattttat ccataagatt agcggatcct acctgacgct ttttatcgca   1260
actctctact gtttctccat acccg                                         1285
```

<210> SEQ ID NO 24
<211> LENGTH: 1285
<212> TYPE: DNA
<213> ORGANISM: Escherichia coli
<220> FEATURE:
<221> NAME/KEY: CDS
<222> LOCATION: (266)..(1192)

<400> SEQUENCE: 24

```
cgggtatgga gaaacagtag agagttgcga taaaaagcgt caggtaggat ccgctaatct     60
tatggataaa aatgctatgg catagcaaag tgtgacgccg tgcaaataat caatgtggac    120
ttttctgccg tgattataga cacttttgtt acgcgttttt gtcatggctt tggtcccgct    180
ttgttacaga atgcttttaa taagcggggt taccggtttg gttagcgaga gagccagta    240 aaagacgcag tgacggcaat gtctg atg caa tat gga caa ttg gtt tct tct    292
                               Met Gln Tyr Gly Gln Leu Val Ser Ser
                                1               5 ctg aat ggc ggg agt atg aaa agt atg gct gaa gcg caa aat gat ccc      340
Leu Asn Gly Gly Ser Met Lys Ser Met Ala Glu Ala Gln Asn Asp Pro
 10              15                  20                  25 ctg ctg ccg gga tac tcg ttt aat gcc cat ctg gtg gcg ggt tta acg      388
Leu Leu Pro Gly Tyr Ser Phe Asn Ala His Leu Val Ala Gly Leu Thr
             30                  35                  40 ccg att gag gcc aac ggt tat ctc gat ttt ttt atc gac cga ccg ctg      436
Pro Ile Glu Ala Asn Gly Tyr Leu Asp Phe Phe Ile Asp Arg Pro Leu
         45                  50                  55 gga atg aaa ggt tat att ctc aat ctc acc att cgc ggt cag ggg gtg      484
Gly Met Lys Gly Tyr Ile Leu Asn Leu Thr Ile Arg Gly Gln Gly Val
     60                  65                  70 gtg aaa aat cag gga cga gaa ttt gtt tgc cga ccg ggt gat att ttg      532
Val Lys Asn Gln Gly Arg Glu Phe Val Cys Arg Pro Gly Asp Ile Leu
 75                  80                  85 ctg ttc ccg cca gga gag att cat cac tac ggt cgt cat ccg gag gct      580
Leu Phe Pro Pro Gly Glu Ile His His Tyr Gly Arg His Pro Glu Ala
 90                  95                 100                 105 cgc gaa tgg tat cac cag tgg gtt tac ttt cgt ccg cgc gcc tac tgg      628
Arg Glu Trp Tyr His Gln Trp Val Tyr Phe Arg Pro Arg Ala Tyr Trp
                110                 115                 120 cat gaa tgg ctt aac tgg ccg tca ata ttt gcc aat acg ggg ttc ttt      676
His Glu Trp Leu Asn Trp Pro Ser Ile Phe Ala Asn Thr Gly Phe Phe
            125                 130                 135 cgc ccg gat gaa gcg cac cag ccg cat ttc agc gac ctg ttt ggg caa      724
Arg Pro Asp Glu Ala His Gln Pro His Phe Ser Asp Leu Phe Gly Gln
        140                 145                 150 atc att aac gcc ggg caa ggg gaa ggg cgc tat tcg gag ctg ctg gcg      772
Ile Ile Asn Ala Gly Gln Gly Glu Gly Arg Tyr Ser Glu Leu Leu Ala
    155                 160                 165 ata aat ctg ctt gag caa ttg tta ctg cgg cgc atg gaa gcg att aac      820
Ile Asn Leu Leu Glu Gln Leu Leu Leu Arg Arg Met Glu Ala Ile Asn
```

```
                170                 175                 180                185
gag tcg ctc cat cca ccg atg gat aat cgg gta cgc gag gct tgt cag         868
Glu Ser Leu His Pro Pro Met Asp Asn Arg Val Arg Glu Ala Cys Gln
                    190                 195                 200 tac atc agc gat cac ctg gca gac agc aat ttt gat atc gcc agc gtc         916
Tyr Ile Ser Asp His Leu Ala Asp Ser Asn Phe Asp Ile Ala Ser Val
                205                 210                 215 gca cag cat gtt tgc ttg tcg ccg tcg cgt ctg tca cat ctt ttc cgc         964
Ala Gln His Val Cys Leu Ser Pro Ser Arg Leu Ser His Leu Phe Arg
            220                 225                 230 cag cag tta ggg att agc gtc tta agc tgg cgc gag gac caa cgt atc        1012
Gln Gln Leu Gly Ile Ser Val Leu Ser Trp Arg Glu Asp Gln Arg Ile
        235                 240                 245 agc cag gcg aag ctg ctt ttg agc acc acc cgg atg cct atc gcc acc        1060
Ser Gln Ala Lys Leu Leu Leu Ser Thr Thr Arg Met Pro Ile Ala Thr
250                 255                 260                 265 gtc ggt cgc aat gtt ggt ttt gac gat caa ctc tat ttc tcg cgg gta        1108
Val Gly Arg Asn Val Gly Phe Asp Asp Gln Leu Tyr Phe Ser Arg Val
                270                 275                 280 ttt aaa aaa tgc acc ggg gcc agc ccg agc gag ttc cgt gcc ggt tgt        1156
Phe Lys Lys Cys Thr Gly Ala Ser Pro Ser Glu Phe Arg Ala Gly Cys
            285                 290                 295 gaa gaa aaa gtg aat gat gta gcc gtc aag ttg tca taattggtaa             1202
Glu Glu Lys Val Asn Asp Val Ala Val Lys Leu Ser
        300                 305 cgaatcagac aattgacggc ttgacggagt agcatagggt ttgcagaatc cctgcttcgt      1262
ccatttgaca ggcacattat gca                                              1285

<210> SEQ ID NO 25
<211> LENGTH: 309
<212> TYPE: PRT
<213> ORGANISM: Escherichia coli

<400> SEQUENCE: 25

Met Gln Tyr Gly Gln Leu Val Ser Ser Leu Asn Gly Gly Ser Met Lys
1               5                   10                  15

Ser Met Ala Glu Ala Gln Asn Asp Pro Leu Leu Pro Gly Tyr Ser Phe
            20                  25                  30

Asn Ala His Leu Val Ala Gly Leu Thr Pro Ile Glu Ala Asn Gly Tyr
        35                  40                  45

Leu Asp Phe Phe Ile Asp Arg Pro Leu Gly Met Lys Gly Tyr Ile Leu
    50                  55                  60

Asn Leu Thr Ile Arg Gly Gln Gly Val Val Lys Asn Gln Gly Arg Glu
65                  70                  75                  80

Phe Val Cys Arg Pro Gly Asp Ile Leu Leu Phe Pro Pro Gly Glu Ile
                85                  90                  95

His His Tyr Gly Arg His Pro Glu Ala Arg Glu Trp Tyr His Gln Trp
            100                 105                 110

Val Tyr Phe Arg Pro Arg Ala Tyr Trp His Glu Trp Leu Asn Trp Pro
        115                 120                 125

Ser Ile Phe Ala Asn Thr Gly Phe Phe Arg Pro Asp Glu Ala His Gln
    130                 135                 140

Pro His Phe Ser Asp Leu Phe Gly Gln Ile Ile Asn Ala Gly Gln Gly
145                 150                 155                 160

Glu Gly Arg Tyr Ser Glu Leu Leu Ala Ile Asn Leu Leu Glu Gln Leu
                165                 170                 175
```

-continued

```
Leu Leu Arg Arg Met Glu Ala Ile Asn Glu Ser Leu His Pro Pro Met
            180                 185                 190

Asp Asn Arg Val Arg Glu Ala Cys Gln Tyr Ile Ser Asp His Leu Ala
        195                 200                 205

Asp Ser Asn Phe Asp Ile Ala Ser Val Ala Gln His Val Cys Leu Ser
    210                 215                 220

Pro Ser Arg Leu Ser His Leu Phe Arg Gln Gln Leu Gly Ile Ser Val
225                 230                 235                 240

Leu Ser Trp Arg Glu Asp Gln Arg Ile Ser Gln Ala Lys Leu Leu Leu
                245                 250                 255

Ser Thr Thr Arg Met Pro Ile Ala Thr Val Gly Arg Asn Val Gly Phe
            260                 265                 270

Asp Asp Gln Leu Tyr Phe Ser Arg Val Phe Lys Lys Cys Thr Gly Ala
        275                 280                 285

Ser Pro Ser Glu Phe Arg Ala Gly Cys Glu Glu Lys Val Asn Asp Val
    290                 295                 300

Ala Val Lys Leu Ser
305
```

```
<210> SEQ ID NO 26
<211> LENGTH: 56
<212> TYPE: DNA
<213> ORGANISM: Synthetic
<220> FEATURE:
<223> OTHER INFORMATION: lacIq-trc promoter

<400> SEQUENCE: 26
ttgacaatta atcatccggc tcgtataatg tgtggaattg tgagcggata acaatt      56

<210> SEQ ID NO 27
<211> LENGTH: 55
<212> TYPE: DNA
<213> ORGANISM: Synthetic
<220> FEATURE:
<223> OTHER INFORMATION: lacIq-tac promoter

<400> SEQUENCE: 27
ttgacaatta atcatcggct cgtataatgt gtggaattgt gagcggataa caatt       55

<210> SEQ ID NO 28
<211> LENGTH: 1092
<212> TYPE: DNA
<213> ORGANISM: Escherichia coli
<220> FEATURE:
<221> NAME/KEY: CDS
<222> LOCATION: (1)..(1089)

<400> SEQUENCE: 28 gtg gtg aat gtg aaa cca gta acg tta tac gat gtc gca gag tat gcc    48
Val Val Asn Val Lys Pro Val Thr Leu Tyr Asp Val Ala Glu Tyr Ala
1               5                   10                  15 ggt gtc tct tat cag acc gtt tcc cgc gtg gtg aac cag gcc agc cac    96
Gly Val Ser Tyr Gln Thr Val Ser Arg Val Val Asn Gln Ala Ser His
            20                  25                  30 gtt tct gcg aaa acg cgg gaa aaa gtg gaa gcg gcg atg gcg gag ctg   144
Val Ser Ala Lys Thr Arg Glu Lys Val Glu Ala Ala Met Ala Glu Leu
        35                  40                  45 aat tac att ccc aac cgc gtg gca caa caa ctg gcg ggc aaa cag tcg   192
Asn Tyr Ile Pro Asn Arg Val Ala Gln Gln Leu Ala Gly Lys Gln Ser
    50                  55                  60 ttg ctg att ggc gtt gcc acc tcc agt ctg gcc ctg cac gcg ccg tcg   240
```

| | | |
|---|---|---|
| Leu Leu Ile Gly Val Ala Thr Ser Ser Leu Ala Leu His Ala Pro Ser<br>65                               70                       75                   80 | |
| caa att gtc gcg gcg att aaa tct cgc gcc gat caa ctg ggt gcc agc<br>Gln Ile Val Ala Ala Ile Lys Ser Arg Ala Asp Gln Leu Gly Ala Ser<br>                      85                      90                      95 | 288 |
| gtg gtg gtg tcg atg gta gaa cga agc ggc gtc gaa gcc tgt aaa gcg<br>Val Val Val Ser Met Val Glu Arg Ser Gly Val Glu Ala Cys Lys Ala<br>                100                     105                    110 | 336 |
| gcg gtg cac aat ctt ctc gcg caa cgc gtc agt ggg ctg atc att aac<br>Ala Val His Asn Leu Leu Ala Gln Arg Val Ser Gly Leu Ile Ile Asn<br>            115                     120                    125 | 384 |
| tat ccg ctg gat gac cag gat gcc att gct gtg gaa gct gcc tgc act<br>Tyr Pro Leu Asp Asp Gln Asp Ala Ile Ala Val Glu Ala Ala Cys Thr<br>      130                     135                    140 | 432 |
| aat gtt ccg gcg tta ttt ctt gat gtc tct gac cag aca ccc atc aac<br>Asn Val Pro Ala Leu Phe Leu Asp Val Ser Asp Gln Thr Pro Ile Asn<br>145                      150                     155                   160 | 480 |
| agt att att ttc tcc cat gaa gac ggt acg cga ctg ggc gtg gag cat<br>Ser Ile Ile Phe Ser His Glu Asp Gly Thr Arg Leu Gly Val Glu His<br>                165                     170                    175 | 528 |
| ctg gtc gca ttg ggt cac cag caa atc gcg ctg tta gcg ggc cca tta<br>Leu Val Ala Leu Gly His Gln Gln Ile Ala Leu Leu Ala Gly Pro Leu<br>            180                     185                    190 | 576 |
| agt tct gtc tcg gcg cgt ctg cgt ctg gct ggc tgg cat aaa tat ctc<br>Ser Ser Val Ser Ala Arg Leu Arg Leu Ala Gly Trp His Lys Tyr Leu<br>            195                     200                    205 | 624 |
| act cgc aat caa att cag ccg ata gcg gaa cgg gaa ggc gac tgg agt<br>Thr Arg Asn Gln Ile Gln Pro Ile Ala Glu Arg Glu Gly Asp Trp Ser<br>      210                     215                    220 | 672 |
| gcc atg tcc ggt ttt caa caa acc atg caa atg ctg aat gag ggc atc<br>Ala Met Ser Gly Phe Gln Gln Thr Met Gln Met Leu Asn Glu Gly Ile<br>225                      230                     235                   240 | 720 |
| gtt ccc act gcg atg ctg gtt gcc aac gat cag atg gcg ctg ggc gca<br>Val Pro Thr Ala Met Leu Val Ala Asn Asp Gln Met Ala Leu Gly Ala<br>                245                     250                    255 | 768 |
| atg cgc gcc att acc gag tcc ggg ctg cgc gtt ggt gcg gat atc tcg<br>Met Arg Ala Ile Thr Glu Ser Gly Leu Arg Val Gly Ala Asp Ile Ser<br>            260                     265                    270 | 816 |
| gta gtg gga tac gac gat acc gaa gac agc tca tgt tat atc ccg ccg<br>Val Val Gly Tyr Asp Asp Thr Glu Asp Ser Ser Cys Tyr Ile Pro Pro<br>            275                     280                    285 | 864 |
| tca acc acc atc aaa cag gat ttt cgc ctg ctg ggg caa acc agc gtg<br>Ser Thr Thr Ile Lys Gln Asp Phe Arg Leu Leu Gly Gln Thr Ser Val<br>      290                     295                    300 | 912 |
| gac cgt ttg ctg caa ctc tct cag ggc cag gcg gtg aag ggc aat cag<br>Asp Arg Leu Leu Gln Leu Ser Gln Gly Gln Ala Val Lys Gly Asn Gln<br>305                      310                     315                   320 | 960 |
| ctg ttg ccc gtc tca ctg gtg aaa aga aaa acc acc ctg gcg ccc aat<br>Leu Leu Pro Val Ser Leu Val Lys Arg Lys Thr Thr Leu Ala Pro Asn<br>                325                     330                    335 | 1008 |
| acg caa acc gcc tct ccc cgc gcg ttg gcc gat tca tta atg cag ctg<br>Thr Gln Thr Ala Ser Pro Arg Ala Leu Ala Asp Ser Leu Met Gln Leu<br>            340                     345                    350 | 1056 |
| gca cga cag gtt tcc cga ctg gaa agc ggg cag tga<br>Ala Arg Gln Val Ser Arg Leu Glu Ser Gly Gln<br>            355                     360 | 1092 |

<210> SEQ ID NO 29
<211> LENGTH: 363
<212> TYPE: PRT

<213> ORGANISM: Escherichia coli

<400> SEQUENCE: 29

| Val | Val | Asn | Val | Lys | Pro | Val | Thr | Leu | Tyr | Asp | Val | Ala | Glu | Tyr | Ala |
|---|---|---|---|---|---|---|---|---|---|---|---|---|---|---|---|
| 1 | | | | 5 | | | | | 10 | | | | | 15 | |

| Gly | Val | Ser | Tyr | Gln | Thr | Val | Ser | Arg | Val | Val | Asn | Gln | Ala | Ser | His |
|---|---|---|---|---|---|---|---|---|---|---|---|---|---|---|---|
| | | | 20 | | | | | 25 | | | | | 30 | | |

| Val | Ser | Ala | Lys | Thr | Arg | Glu | Lys | Val | Glu | Ala | Met | Ala | Glu | Leu |
|---|---|---|---|---|---|---|---|---|---|---|---|---|---|---|
| | | 35 | | | | | 40 | | | | | 45 | | |

| Asn | Tyr | Ile | Pro | Asn | Arg | Val | Ala | Gln | Gln | Leu | Ala | Gly | Lys | Gln | Ser |
|---|---|---|---|---|---|---|---|---|---|---|---|---|---|---|---|
| | 50 | | | | | 55 | | | | | 60 | | | | |

| Leu | Leu | Ile | Gly | Val | Ala | Thr | Ser | Ser | Leu | Ala | Leu | His | Ala | Pro | Ser |
|---|---|---|---|---|---|---|---|---|---|---|---|---|---|---|---|
| 65 | | | | | 70 | | | | | 75 | | | | | 80 |

| Gln | Ile | Val | Ala | Ala | Ile | Lys | Ser | Arg | Ala | Asp | Gln | Leu | Gly | Ala | Ser |
|---|---|---|---|---|---|---|---|---|---|---|---|---|---|---|---|
| | | | | 85 | | | | | 90 | | | | | 95 | |

| Val | Val | Val | Ser | Met | Val | Glu | Arg | Ser | Gly | Val | Glu | Ala | Cys | Lys | Ala |
|---|---|---|---|---|---|---|---|---|---|---|---|---|---|---|---|
| | | | 100 | | | | | 105 | | | | | 110 | | |

| Ala | Val | His | Asn | Leu | Leu | Ala | Gln | Arg | Val | Ser | Gly | Leu | Ile | Ile | Asn |
|---|---|---|---|---|---|---|---|---|---|---|---|---|---|---|---|
| | | 115 | | | | | 120 | | | | | 125 | | | |

| Tyr | Pro | Leu | Asp | Asp | Gln | Asp | Ala | Ile | Ala | Val | Glu | Ala | Ala | Cys | Thr |
|---|---|---|---|---|---|---|---|---|---|---|---|---|---|---|---|
| | 130 | | | | | 135 | | | | | 140 | | | | |

| Asn | Val | Pro | Ala | Leu | Phe | Leu | Asp | Val | Ser | Asp | Gln | Thr | Pro | Ile | Asn |
|---|---|---|---|---|---|---|---|---|---|---|---|---|---|---|---|
| 145 | | | | | 150 | | | | | 155 | | | | | 160 |

| Ser | Ile | Ile | Phe | Ser | His | Glu | Asp | Gly | Thr | Arg | Leu | Gly | Val | Glu | His |
|---|---|---|---|---|---|---|---|---|---|---|---|---|---|---|---|
| | | | | 165 | | | | | 170 | | | | | 175 | |

| Leu | Val | Ala | Leu | Gly | His | Gln | Gln | Ile | Ala | Leu | Leu | Ala | Gly | Pro | Leu |
|---|---|---|---|---|---|---|---|---|---|---|---|---|---|---|---|
| | | | 180 | | | | | 185 | | | | | 190 | | |

| Ser | Ser | Val | Ser | Ala | Arg | Leu | Arg | Leu | Ala | Gly | Trp | His | Lys | Tyr | Leu |
|---|---|---|---|---|---|---|---|---|---|---|---|---|---|---|---|
| | | 195 | | | | | 200 | | | | | 205 | | | |

| Thr | Arg | Asn | Gln | Ile | Gln | Pro | Ile | Ala | Glu | Arg | Glu | Gly | Asp | Trp | Ser |
|---|---|---|---|---|---|---|---|---|---|---|---|---|---|---|---|
| 210 | | | | | 215 | | | | | 220 | | | | | |

| Ala | Met | Ser | Gly | Phe | Gln | Gln | Thr | Met | Gln | Met | Leu | Asn | Glu | Gly | Ile |
|---|---|---|---|---|---|---|---|---|---|---|---|---|---|---|---|
| 225 | | | | | 230 | | | | | 235 | | | | | 240 |

| Val | Pro | Thr | Ala | Met | Leu | Val | Ala | Asn | Asp | Gln | Met | Ala | Leu | Gly | Ala |
|---|---|---|---|---|---|---|---|---|---|---|---|---|---|---|---|
| | | | | 245 | | | | | 250 | | | | | 255 | |

| Met | Arg | Ala | Ile | Thr | Glu | Ser | Gly | Leu | Arg | Val | Gly | Ala | Asp | Ile | Ser |
|---|---|---|---|---|---|---|---|---|---|---|---|---|---|---|---|
| | | | 260 | | | | | 265 | | | | | 270 | | |

| Val | Val | Gly | Tyr | Asp | Asp | Thr | Glu | Asp | Ser | Ser | Cys | Tyr | Ile | Pro | Pro |
|---|---|---|---|---|---|---|---|---|---|---|---|---|---|---|---|
| | | 275 | | | | | 280 | | | | | 285 | | | |

| Ser | Thr | Thr | Ile | Lys | Gln | Asp | Phe | Arg | Leu | Leu | Gly | Gln | Thr | Ser | Val |
|---|---|---|---|---|---|---|---|---|---|---|---|---|---|---|---|
| | 290 | | | | | 295 | | | | | 300 | | | | |

| Asp | Arg | Leu | Leu | Gln | Leu | Ser | Gln | Gly | Gln | Ala | Val | Lys | Gly | Asn | Gln |
|---|---|---|---|---|---|---|---|---|---|---|---|---|---|---|---|
| 305 | | | | | 310 | | | | | 315 | | | | | 320 |

| Leu | Leu | Pro | Val | Ser | Leu | Val | Lys | Arg | Lys | Thr | Thr | Leu | Ala | Pro | Asn |
|---|---|---|---|---|---|---|---|---|---|---|---|---|---|---|---|
| | | | | 325 | | | | | 330 | | | | | 335 | |

| Thr | Gln | Thr | Ala | Ser | Pro | Arg | Ala | Leu | Ala | Asp | Ser | Leu | Met | Gln | Leu |
|---|---|---|---|---|---|---|---|---|---|---|---|---|---|---|---|
| | | | 340 | | | | | 345 | | | | | 350 | | |

| Ala | Arg | Gln | Val | Ser | Arg | Leu | Glu | Ser | Gly | Gln |
|---|---|---|---|---|---|---|---|---|---|---|
| | | 355 | | | | | 360 | | | |

<210> SEQ ID NO 30
<211> LENGTH: 1511
<212> TYPE: DNA
<213> ORGANISM: Escherichia coli

```
<400> SEQUENCE: 30
catgcattta cgttgacacc atcgaatggt gcaaaacctt tcgcggtatg gcatgatagc    60
gcccggaaga gagtcaattc agggtggtga atgtgaaacc agtaacgtta tacgatgtcg   120
cagagtatgc cggtgtctct tatcagaccg tttcccgcgt ggtgaaccag gccagccacg   180
tttctgcgaa aacgcgggaa aaagtggaag cggcgatggc ggagctgaat tacattccca   240
accgcgtggc acaacaactg gcgggcaaac agtcgttgct gattggcgtt gccacctcca   300
gtctggccct gcacgcgccg tcgcaaattg tcgcggcgat taaatctcgc gccgatcaac   360
tgggtgccag cgtggtggtg tcgatggtag aacgaagcgg cgtcgaagcc tgtaaagcgg   420
cggtgcacaa tcttctcgcg caacgcgtca gtgggctgat cattaactat ccgctggatg   480
accaggatgc cattgctgtg gaagctgcct gcactaatgt tccggcgtta tttcttgatg   540
tctctgacca gacacccatc aacagtatta ttttctccca tgaagacggt acgcgactgg   600
gcgtggagca tctggtcgca ttgggtcacc agcaaatcgc gctgttagcg ggcccattaa   660
gttctgtctc ggcgcgtctg cgtctggctg gctggcataa atatctcact cgcaatcaaa   720
ttcagccgat agcggaacgg gaaggcgact ggagtgccat gtccggtttt caacaaacca   780
tgcaaatgct gaatgagggc atcgttccca ctgcgatgct ggttgccaac gatcagatgg   840
cgctgggcgc aatgcgcgcc attaccgagt ccgggctgcg cgttggtgcg gatatctcgg   900
tagtgggata cgacgatacc gaagacagct catgttatat cccgccgtca accaccatca   960
aacaggattt tcgcctgctg gggcaaacca gcgtggaccg cttgctgcaa ctctctcagg  1020
gccaggcggt gaagggcaat cagctgtttg ccgtctcact ggtgaaaaga aaaaccaccc  1080
tggcgcccaa tacgcaaacc gcctctcccc gcgcgttggc cgattcatta atgcagctgg  1140
cacgacaggt ttcccgactg gaaagcgggc agtgagcgca acgcaattaa tgtgagttag  1200
cgcgaattga tctggtttga cagcttatca tcgactgcac ggtgcaccaa tgcttctggc  1260
gtcaggcagc catcggaagc tgtggtatgg ctgtgcaggt cgtaaatcac tgcataattc  1320
gtgtcgctca aggcgcactc ccgttctgga taatgttttt tgcgccgaca tcataacggt  1380
tctggcaaat attctgaaat gagctgttga caattaatca tccggctcgt ataatgtgtg  1440
gaattgtgag cggataacaa tttcacacag gaaacagacc atggaattcg agctcggtac  1500
ccggggatcc t                                                       1511

<210> SEQ ID NO 31
<211> LENGTH: 26
<212> TYPE: DNA
<213> ORGANISM: Artificial Sequence
<220> FEATURE:
<223> OTHER INFORMATION: Oligonucleotide forward primer

<400> SEQUENCE: 31
gtgcggatcc tggctttcca acgttt                                        26

<210> SEQ ID NO 32
<211> LENGTH: 26
<212> TYPE: DNA
<213> ORGANISM: Artificial Sequence
<220> FEATURE:
<223> OTHER INFORMATION: Oligonucleotide reverse primer

<400> SEQUENCE: 32
catgggctcg agatgacctg tgccta                                        26
```

-continued

<210> SEQ ID NO 33
<211> LENGTH: 544
<212> TYPE: DNA
<213> ORGANISM: Corynebacterium glutamicum

<400> SEQUENCE: 33

| | | |
|---|---|---|
| ctgggaaggg taccgcctaa tcctcaccgc attacttgga caatcgtgc agcagtattc | 60 |
| ctttaacgct ggcgaactac aaaaatcgct acccgccatg accattgccg aaccaattgt | 120 |
| cgccttcagt ttgggctact tggttctggg cgaaaaattc caagtcgtgg actgggaatg | 180 |
| gatcgccatg gcatcgcac tcttggtgat gattgtttcc accattgcac tgtctcgtac | 240 |
| aagcacaatg ccggccggat cgaaaaggta aactccaaa gttcccccc cgagacatga | 300 |
| cagcactgga actgggcgtc gaaaagcttt tttaaaagaa actcccccc gagttgctac | 360 |
| ccacaccaca aagttgttgt atgcttcacc acatgacttc gcgtgcgaat ctacttcttc | 420 |
| ttcgccgcgg cgggtcccag aggtcttaac acgaccggca tcccgtcgcg gagtttggtg | 480 |
| ttgccggtcg tggacccacc caaaactttt taagaaggtt ctagacaatg tcttctaacg | 540 |
| atgc | 544 |

<210> SEQ ID NO 34
<211> LENGTH: 500
<212> TYPE: DNA
<213> ORGANISM: Corynebacterium glutamicum

<400> SEQUENCE: 34

| | | |
|---|---|---|
| gaaccaatca ctggtacctc ggacaaccga tcgatcagtg cttgctgctc ttcgctgatt | 60 |
| tcatcgtcat catcgctggt gtctttgccg gaggagctca agctcggggc cgcaggaatg | 120 |
| tcgccactgc tgagcattga gctgccttca gagctgcctg gccaggtttc gtttccatcg | 180 |
| actggttttc catcatcatc aaggatctgt gatgaggtga tgttgtctga gagctgtgtc | 240 |
| agtgcgtcag aggactgagc ctgggcaact ggagtgaaca cggacaatgc cacagcgctt | 300 |
| gctgtaacaa gggtcaaagt acttcgacgc aaagacaaaa ctttctcct ggcaataaat | 360 |
| atgcggattt actatggaaa caagatagaa gattggatag cgaaagctat cctcaactcg | 420 |
| tggaaagtgt aatgccacaa ccacagtatt ggctagaaaa caatctatag cattgttcta | 480 |
| caaagagctc gttggaaata | 500 |

<210> SEQ ID NO 35
<211> LENGTH: 500
<212> TYPE: DNA
<213> ORGANISM: Corynebacterium glutamicum

<400> SEQUENCE: 35

| | | |
|---|---|---|
| ctacatcaaa accggtaccg acaatccaat tccacaatga atagagcaaa tattgaatgg | 60 |
| gtacgcctaa aatcatgagc caagattagc gctgaaaagt agcgggagcc tgcctgaact | 120 |
| ttgtgagaat cctgattcct taaccgaagt gggggagttt tgggggtggg aattttcgtg | 180 |
| cgttgtggaa ttggaaactc gatgtgtgta gcatgacaca ccatgaccat tattcgactt | 240 |
| gtagtagtaa ccgcgcggcg cctgccgtaa cggccttcca agtcgtctcg tcaagcgccc | 300 |
| tcgacaacac tcaccacagt gttggaacga gggctttctt gttggttatg acccaagtag | 360 |
| ccaactttgc aacagacatc tgtcgcactg cgtgcacacg catccgcgtc ggaacaattt | 420 |
| taaatgaggg ctttgtcttt aggctgagtt gaaatcggct tggcttggac gggtcctgtg | 480 |
| aaaatcctta tttagtaaag | 500 |